United States Patent
Lee et al.

(10) Patent No.: US 9,175,087 B2
(45) Date of Patent: Nov. 3, 2015

(54) HUMANIZED ANTI-CXCR5 ANTIBODIES, DERIVATIVES THEREOF AND THEIR USE

(71) Applicant: SANOFI, Paris (FR)

(72) Inventors: Renata Lee, Edison, NJ (US); Vincent Mikol, Charenton-le-Pont (FR); Elizabeth Allen, Stewartsville, NJ (US); Norman Ruetsch, Moorestown, NJ (US); Beatrice Cameron, Paris (FR); Thomas Oligino, Forks Township, PA (US); Nicholas Baurin, St Germain les Arpajon (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/794,281

(22) Filed: Mar. 11, 2013

(65) Prior Publication Data

US 2013/0246035 A1 Sep. 19, 2013

Related U.S. Application Data

(62) Division of application No. 12/675,799, filed as application No. PCT/US2008/074381 on Aug. 27, 2008, now Pat. No. 8,647,622.

(60) Provisional application No. 60/968,792, filed on Aug. 29, 2007.

(51) Int. Cl.
*A61K 39/395* (2006.01)
*C07K 16/28* (2006.01)
*G06F 19/12* (2011.01)
*A61K 39/00* (2006.01)

(52) U.S. Cl.
CPC ............. *C07K 16/2896* (2013.01); *C07K 16/28* (2013.01); *C07K 16/2866* (2013.01); *G06F 19/12* (2013.01); *A61K 2039/505* (2013.01); *C07K 2317/24* (2013.01); *C07K 2317/33* (2013.01); *C07K 2317/565* (2013.01); *C07K 2317/567* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 3,773,919 A | 11/1973 | Boswell et al. | |
| 4,179,337 A | 12/1979 | Davis et al. | |
| 4,256,746 A | 3/1981 | Miyashita et al. | |
| 4,275,149 A | 6/1981 | Litman et al. | |
| 4,294,757 A | 10/1981 | Asai | |
| 4,301,144 A | 11/1981 | Iwashita et al. | |
| 4,307,016 A | 12/1981 | Asai et al. | |
| 4,313,946 A | 2/1982 | Powell et al. | |
| 4,315,929 A | 2/1982 | Freedman et al. | |
| 4,318,980 A | 3/1982 | Boguslaski et al. | |
| 4,322,348 A | 3/1982 | Asai et al. | |
| 4,331,598 A | 5/1982 | Hasegawa et al. | |
| 4,361,650 A | 11/1982 | Asai et al. | |
| 4,362,663 A | 12/1982 | Kida et al. | |
| 4,364,866 A | 12/1982 | Asai et al. | |
| 4,371,533 A | 2/1983 | Akimoto et al. | |
| 4,376,110 A | 3/1983 | David et al. | |
| 4,424,219 A | 1/1984 | Hashimoto et al. | |
| 4,444,887 A | 4/1984 | Hoffmann | |
| 4,450,254 A | 5/1984 | Isley et al. | |
| 4,496,689 A | 1/1985 | Mitra | |
| 4,560,655 A | 12/1985 | Baker | |
| 4,640,835 A | 2/1987 | Shimizu et al. | |
| 4,657,866 A | 4/1987 | Kumar | |
| 4,670,417 A | 6/1987 | Iwasaki et al. | |
| 4,676,980 A | 6/1987 | Segal et al. | |
| 4,716,111 A | 12/1987 | Osband et al. | |
| 4,737,456 A | 4/1988 | Weng et al. | |
| 4,767,704 A | 8/1988 | Cleveland et al. | |
| 4,791,192 A | 12/1988 | Nakagawa et al. | |
| 4,816,397 A | 3/1989 | Boss et al. | |
| 4,946,778 A | 8/1990 | Ladner et al. | |
| 4,980,286 A | 12/1990 | Morgan et al. | |
| 5,122,464 A | 6/1992 | Wilson et al. | |
| 5,122,469 A | 6/1992 | Mather et al. | |
| 5,223,409 A | 6/1993 | Ladner et al. | |
| 5,225,539 A | 7/1993 | Winter | |
| 5,314,995 A | 5/1994 | Fell, Jr. et al. | |
| 5,413,923 A | 5/1995 | Kucherlapati et al. | |
| 5,436,146 A | 7/1995 | Shenk et al. | |

(Continued)

FOREIGN PATENT DOCUMENTS

| | | |
|---|---|---|
| EP | 0 239 400 A2 | 9/1987 |
| EP | 0 332 424 A1 | 9/1989 |

(Continued)

OTHER PUBLICATIONS

Ishikawa et at., "Aberrant high expression of B lymphocyte chemokine (BLC/CXCL13) by C11b+CD11c+ dendritic cells in murine lupus and preferential chemotaxis of B1 cells towards BLC," 193(12) J Exp Med 1393-1402 (2001).

Jakobovits et al., "Analysis of homozygous mutant chimeric mice: deletion of the immunoglobulin heavy-chain joining region blocks B-cell development and antibody production," 90(6) Proc Nat'l Acad Sci USA 2551-5 (1993).

Jakobovits et al., "Germ-line transmission and expression of a human-derived yeast artificial chromosome," 362 (6417) Nature 255-8 (1993).

James et al., "Antibody multispecificity mediated by conformational diversity," 299(5611) Science 1362-7 (2003).

(Continued)

*Primary Examiner* — Laura B Goddard
*Assistant Examiner* — Meera Natarajan
(74) *Attorney, Agent, or Firm* — McDonnell Boehnen Hulbert & Berghoff LLP; Ann Marie Szczepanik

(57) ABSTRACT

The present invention relates to humanized antibodies that specifically bind to CXCR5 and can, for example, inhibit CXCR5 function. The invention also includes uses of the antibodies to treat or prevent CXCR5 related diseases or disorders.

11 Claims, No Drawings

(56) References Cited

U.S. PATENT DOCUMENTS

| | | | |
|---|---|---|---|
| 5,474,981 A | 12/1995 | Leder et al. | |
| 5,475,092 A | 12/1995 | Chari et al. | |
| 5,530,101 A | 6/1996 | Queen et al. | |
| 5,534,617 A | 7/1996 | Cunningham et al. | |
| 5,545,806 A | 8/1996 | Lonberg et al. | |
| 5,565,332 A | 10/1996 | Hoogenboom et al. | |
| 5,569,825 A | 10/1996 | Lonberg et al. | |
| 5,585,089 A | 12/1996 | Queen et al. | |
| 5,585,499 A | 12/1996 | Chari et al. | |
| 5,625,126 A | 4/1997 | Lonberg et al. | |
| 5,633,425 A | 5/1997 | Lonberg et al. | |
| 5,639,641 A | 6/1997 | Pedersen et al. | |
| 5,661,016 A | 8/1997 | Lonberg et al. | |
| 5,698,417 A | 12/1997 | Robinson et al. | |
| 5,698,435 A | 12/1997 | Robinson et al. | |
| 5,712,163 A | 1/1998 | Parenteau et al. | |
| 5,807,715 A | 9/1998 | Morrison et al. | |
| 5,814,318 A | 9/1998 | Lonberg et al. | |
| 5,821,337 A | 10/1998 | Carter et al. | |
| 5,846,545 A | 12/1998 | Chari et al. | |
| 5,869,619 A | 2/1999 | Studnicka | |
| 5,885,793 A | 3/1999 | Griffiths et al. | |
| 5,916,771 A | 6/1999 | Hori et al. | |
| 5,939,598 A | 8/1999 | Kucherlapati et al. | |
| 6,048,728 A | 4/2000 | Inlow et al. | |
| 6,204,023 B1 | 3/2001 | Robinson et al. | |
| 6,277,375 B1 | 8/2001 | Ward | |
| 6,333,410 B1 | 12/2001 | Chari et al. | |
| 6,514,496 B1 | 2/2003 | Platz et al. | |
| 6,632,670 B1 | 10/2003 | Wadsworth et al. | |
| 6,642,051 B1 | 11/2003 | Lynch et al. | |
| 7,288,249 B2 * | 10/2007 | Carter et al. | 424/130.1 |
| 2003/0130496 A1 | 7/2003 | Winter et al. | |
| 2005/0276812 A1 * | 12/2005 | Ebens et al. | 424/178.1 |

FOREIGN PATENT DOCUMENTS

| | | |
|---|---|---|
| EP | 0 338 745 A1 | 10/1989 |
| EP | 0 396 387 A2 | 11/1990 |
| EP | 0 413 622 A1 | 2/1991 |
| EP | 0 439 095 A2 | 7/1991 |
| EP | 0 519 596 A1 | 12/1992 |
| EP | 0 592 106 A1 | 4/1994 |
| RU | 2252786 C2 | 5/2005 |
| WO | 86/05807 A1 | 10/1986 |
| WO | 87/05330 A1 | 9/1987 |
| WO | 89/01036 A1 | 2/1989 |
| WO | 89/09622 A1 | 10/1989 |
| WO | 89/12624 A2 | 12/1989 |
| WO | 91/09967 A1 | 7/1991 |
| WO | 91/10741 A1 | 7/1991 |
| WO | 91/14438 A1 | 10/1991 |
| WO | 92/01047 A1 | 1/1992 |
| WO | 92/06180 A1 | 4/1992 |
| WO | 92/08495 A1 | 5/1992 |
| WO | 92/20316 A2 | 11/1992 |
| WO | 92/22635 A1 | 12/1992 |
| WO | 92/22653 A1 | 12/1992 |
| WO | 93/08829 A1 | 5/1993 |
| WO | 93/14188 A1 | 7/1993 |
| WO | 93/15199 A1 | 8/1993 |
| WO | 93/15200 A1 | 8/1993 |
| WO | 93/16185 A2 | 8/1993 |
| WO | 93/20221 A1 | 10/1993 |
| WO | 93/21232 A1 | 10/1993 |
| WO | 93/21319 A1 | 10/1993 |
| WO | 94/08598 A1 | 4/1994 |
| WO | 94/12649 A2 | 6/1994 |
| WO | 94/25591 A1 | 11/1994 |
| WO | 96/33735 A1 | 10/1996 |
| WO | 96/34096 A1 | 10/1996 |
| WO | 97/33899 A1 | 9/1997 |
| WO | 97/34631 A1 | 9/1997 |
| WO | 97/34911 A1 | 9/1997 |
| WO | 98/16654 A1 | 4/1998 |
| WO | 98/23289 A1 | 6/1998 |
| WO | 98/24893 A2 | 6/1998 |
| WO | 98/46645 A2 | 10/1998 |
| WO | 98/50433 A2 | 11/1998 |
| WO | 99/23105 A1 | 5/1999 |
| WO | 01/77137 A1 | 10/2001 |
| WO | 03/002607 A1 | 1/2003 |
| WO | WO 2004/015426 | 2/2004 |
| WO | 2005/117986 A2 | 12/2005 |
| WO | 2006/042333 A2 | 4/2006 |
| WO | 2007/122402 A1 | 11/2007 |
| WO | 2007/131676 A1 | 11/2007 |
| WO | 2009/032661 A1 | 3/2009 |

OTHER PUBLICATIONS

Jespers et al., "Guiding the selection of human antibodies from phage display repertoires to a single epitope of an antigen," 12(9) Biotechnology 899-903 (1994).

Jones et al., "Replacing the complementarity-determining regions in a human antibody with those from a mouse," 321 (6069) Nature 522-5 (1986).

Kiem et al., "Retrovirus-mediated gene transduction into canine peripheral blood repopulating cells," 83(6) Blood 1467-73 (1994).

Kirschmann et al., "Naturally processed peptides from rheumatoid arthritis associated and non-associated HLA-DR alleles," 155(12) J Immunol 5655-62 (1995).

Köhler, "Immunoglobulin chain loss in hybridoma lines," 77(4) Proc Nat'l Acad Sci USA 2197-9 (1980).

Köhler & Milstein, "Continuous cultures of fused cells secreting antibody of predefined specificity." 256(5517) Nature 495-7 (1975).

Koller & Smithies, "Inactivating the beta 2-microglobulin locus in mouse embryonic stem cells by homologous recombination," 86(22) Proc Nat'l Acad Sci USA 8932-5 (1989).

Kozarsky & Wilson, "Gene therapy: adenovirus vectors," 3(3) Curr Opin Gen Dev 499-503 (1993).

Kozbor & Roder, "The production of monoclonal antibodies from human lymphocytes," 4(3) Immunology Today 72-9 (1983).

Kozbor et al., "A human hybrid myeloma for production of human monoclonal antibodies," 133(6) J Immunol 3001-5 (1984).

Krumbholz et al., "Chemokines in multiple sclerosis: CXCL12 and CXCL13 up-regulation is differentially linked to CNS immune cell recruitment," 129(1) Brain 200-11 (2006).

Kufer et al., "A revival of bispecific antibodies," 22(5) Trends Biotech 238-44 (2004).

Kundu et al., "Dynamics of proteins in crystals: comparison of experiment with simple models," 83(2) Biophys J 723-32 (2002).

Kunkel, "Rapid and efficient site-specific mutagenesis without phenotypic selection," 82(2) Proc Nat'l Acad Sci USA 488-92 (1985).

Kutemeier et al., "Assembly of humanized antibody genes from synthetic oligonucleotides using a single-round PCR," 17(2) BioTechniques 242-6 (1994).

Langer, "New methods in drug delivery," 249(4976) Science 1527-33 (1990).

Langer & Peppas, "Chemical and Physical Structure of Polymers as Carriers for Controlled Release of Bioactive Agents: A Review," 23(1) J Macromol Sci Rev Macromol Chem 61-126 (1983).

Lazar et al., "A molecular immunology approach to antibody humanization and functional optimization," 44(8) Mol Immunol 1986-1988 (2007).

Lefranc et al., "IMGT, the international ImMunoGeneTics information system®," 33(Suppl 1, Database issue) Nucleic Acids Research D593-D597 (2005).

Lefranc, "IMGT-ONTOLOGY and IMGT databases, tools and Web resources for immunogenetics and immunoinformatics," 40(10) Molec Immunol 647-59 (2004).

Lerner, "How to make a hybridoma," 54(5) Yale J Biology and Medicine 387-402 (1981).

Levy et al., "Inhibition of calcification of bioprosthetic heart valves by local controlled-release diphosphonate," 228 (4696) Science 190-2 (1985).

Li et al., "Structural basis for inhibition of the epidermal growth factor receptor by cetuximab," 7(4) Cancer Cell 301-11 (2005).

(56) References Cited

OTHER PUBLICATIONS

Lindmark et al., "Binding of immunoglobulins to protein A and immunoglobulin levels in mammalian sera," 62(1) J Immunol Methods 1-13 (1983).
Liu et al., "Characterization of the stability of a fully human monoclonal IgG after prolonged incubation at elevated temperature," 837(1-2) J Chromatog B 35-43 (2006).
Loeffler & Behr, "Gene transfer into primary and established mammalian cell lines with lipopolyamine-coated DNA," 217 Meth Enzymol 599-618 (1993).
Lonberg & Huszar, "Human antibodies from transgenic mice," 13(1) Int Rev Immunol 65-93 (1995).
Lowman & Wells, "Affinity maturation of human growth hormone by monovalent phage display," 234(3) J Mol Biol 564-78 (1993).
Lowman et al., "Selecting high-affinity binding proteins by monovalent phage display," 30(45) Biochemistry 10832-8 (1991).
Lowy et al., "Isolation of transforming DNA: cloning the hamster aprt gene," 22(3) Cell 817-23 (1980).
Luckow & Summers, "Trends in the development of baculorvirus expression vectors," 6 Nature Biotechnology 47-55 (1988).
Ma et al., "Multiple diverse ligands binding at a single protein site: A matter of pre-existing populations," 11(2) Protein Science 184-7 (2002).
Mackerell et al., "The Encyclopedia of Computational Chemistry," vol. 1:271-77 (Schleyer et al., eds. 1998).
Maeda et al., "Production of human alpha-interferon in silkworm using a baculovirus vector," 315(6020) Nature 592-4 (1985).
Mader & Keystone, "Optimizing treatment with biologics," 80 J Rheumatol Suppl 16-24 (2007).
Marks et al., "X-Ray Structures of D1.3 Fv Mutants," PDB ID; 1A7P, (to be published), retrieved on Feb. 21, 2012.
Marks et al., "By-passing immunization. Human antibodies from V-gene libraries displayed on phage," 222(3) J Mol Biol 581-97 (1991).
Marks et al., "By-passing immunization: building high affinity human antibodies by chain shuffling," 10(7) Biotechnology 779-83 (1992).
Mastrangeli et al., "Diversity of airway epithelial cell targets for in vivo recombinant adenovirus-mediated gene transfer," 91(1) J Clin Invest 225-34 (1993).
Mazzucchelli et al., "BCA-1 is highly expressed in Helicobacter pylori-induced mucosa-associated lymphoid tissue and gastric lymphoma," 104(10) J Clin Invest R49-R54 (1999).
McCafferty et al., "Phage antibodies: filamentous phage displaying antibody variable domains," 348(6301) Nature 552-4 (1990).
Meijer et al., "The CXCR5 chemokine receptor is expressed by carcinoma cells and promotes growth of colon carcinoma in the liver," 66(19) Canc Res 9576-82 (2006).
Miller et al., "An Insect Baculovirus Host-vector System for High-level Expression of Foreign Genes," Genetic Engineering: Principles and Methods, vol. 8:277-98 (Setlow and Hollaender, eds., 1986).
Milstein & Cuello, "Hybrid hybridomas and their use in immunohistochemistry," 305(5934) Nature 537-40 (1983).
Modis et al., "Variable Surface Epitopes in the Crystal Structure of Dengue Virus Type 3 Envelope Glycoprotein," 79 (2) J Virol 1223-31 (2005).
Order, "Analysis, Results, and Future Prospective of the Therapeutic Use of Radiolabeled Antibody in Cancer Therapy," in Monoclonal Antibodies for Cancer Detection and Therapy 303-16 (Baldwin and Byers, eds., 1985).
Morgan & Anderson, "Human gene therapy," 62 Ann Rev Biochem 191-217 (1993).
Morimoto & Inouye, "Single-step purification of F(ab')2 fragments of mouse monoclonal antibodies (immunoglobulins G1) by hydrophobic interaction high performance liquid chromatography using TSKgel Phenyl-5PW ," 24(1-2) J Biochem Biophys Methods 107-17 (1992).
Morrison, "Transfectomas provide novel chimeric antibodies," 229(4719) Science 1202-7 (1985).
Morrison et al., "Chimeric human antibody molecules: mouse antigen-binding domains with human constant region domains," 81(21) Proc Nat'l Acad Sci USA 6851-5 (1984).
Mulligan & Berg, "Selection for animal cells that express the *Escherichia coli* gene coding for xanthine-guanine phosphoribosyltransferase," 78(4) Proc Nat'l Acad Sci USA 2072-6 (1981).
Mulligan, "The basic science of gene therapy," 260(5110) Science 926-32 (1993).
Munson & Rodbard, "Ligand: a versatile computerized approach for characterization of ligand-binding systems," 107(1) Anal Biochem 220-39 (1980).
Naramura et al., "Mechanisms of cellular cytotoxicity mediated by a recombinant antibody-IL2 fusion protein against human melanoma cells," 39(1) Immunol Lett 91-9 (1994).
Newman et al., "Modification of the Fc Region of a Primatized IgG Antibody to Human CD4 Retains Its Ability to Modulate CD4 Receptors but Does Not Deplete CD4+ T Cells in Chimpanzees," 98(2) Clin Immunol 164-74 (2001).
Nilsson & Karplus, "Empirical energy functions for energy minimization and dynamics of nucleic acids," 7(5) J Comput Chem 591-616 (1986).
Nisonoff, "Idiotypes: concepts and applications," 147(8) J Immunol 2429-38 (1991).
Nisonoff et al., "Separation of univalent fragments from the bivalent rabbit antibody molecule by reduction of disulfide bonds," 89 Arch Biochem Biophys 230-44 (1960).
Noorchashm et al., "B cell-mediated antigen presentation is required for the pathogenesis of acute cardiac allograft rejection," 177(11) J Immunol 7715-22 (2006).
Oi & Morrison, "Chimeric antibodies," 4 BioTechniques 214-221 (1986).
O'Hare et al., "Transformation of mouse fibroblasts to methotrexate resistance by a recombinant plasmid expressing a prokaryotic dihydrofolate reductase," 78(3) Proc Nat'l Acad Sci USA 1527-31 (1981).
Oligino & Dalrymple, "Targeting B cells for the treatment of rheumatoid arthritis," 5(Suppl 4) Arthritis Res Ther S7-S11 (2003).
Padlan, "A possible procedure for reducing the immunogenicity of antibody variable domains while preserving their ligand-binding properties," 28(4-5) Molecular Immunology 489-98 (1991).
Parham, "On the fragmentation of monoclonal IgG1, IgG2a, and IgG2b from BALB/c mice," 131(6) J Immunol 2895-2902 (1983).
Pearson & Lipman "Improved tools for biological sequence comparison," 85(8) Proc Nat'l Acad Sci USA 2444-8 (1988).
Peters et al., "The Immune Epitope Database and Analysis Resource: from vision to blueprint," 3(3) PLoS Biol e91 (2005).
Pittelkow & Scott, "New techniques for the in vitro culture of human skin keratinocytes and perspectives on their use for grafting of patients with extensive burns," 61(10) Mayo Clinic Proc 771-7 (1986).
Pozharski et al., "Carving a Binding Site: Structural Study of an Anti-Cocaine Antibody" in "Complex with Three Cocaine Analogs," (to be published), electronic ref retrieved Feb. 21, 2012.
Presta et al., "Humanization of an antibody directed against IgE," 151(5) J Immunol 2623-32 (1993).
Proudfoot, "Transcriptional interference and termination between duplicated alpha-globin gene constructs suggests a novel mechanism for gene regulation," 322(6079) Nature 562-5 (1986).
Qiuping et al., "Selectively frequent expression of CXCR5 enhances resistance to apoptosis in CD8+CD34+ T cells from patients with T-cell-lineage acute lymphocytic leukemia," 24(4) Oncogene 573-84 (2005).
Rader et al., "A phage display approach for rapid antibody humanization: designed combinatorial V gene libraries," 95(15) Proc Nat'l Acad Sci USA 8910-5 (1998).
Reddy et al., "Elimination of Fc Receptor-Dependent Effector Functions of a Modified IgG4 Monoclonal Antibody to Human CD4," 164(4) J Immunol 1925-33 (2000).
Rheinwald, "Serial cultivation of normal human epidermal keratinocytes," 21(A) Meth Cell Bio 229-54 (1980).
Riechmann et al., "Reshaping human antibodies for therapy," 332(6162) Nature 323-7 (1988).

(56) References Cited

OTHER PUBLICATIONS

Rizzo et al., "Validation of a model for the complex of HIV-1 reverse transcriptase with Sustiva through computation of resistance profiles," 122(51) J Am Chem Soc 12898-12900 (2000).
Robinson et al., 11(5) Trends in Biotechnology 155-215 (May 1993).
Roguska et al., "Humanization of murine monoclonal antibodies through variable domain resurfacing," 91(3) Proc Nat'l Acad Sci USA 969-73 (1994).
Romijn et al., "Identification of the Collagen-binding Site of the von Willebrand Factor A3-domain," 276(13) J Biol Chem 9985-91 (2001).
Rosenberg et al., "Vectors for selective expression of cloned DNAs by T7 RNA polymerase," 56(1) Gene 125-35 (1987).
Rosenfeld et al., "Adenovirus-mediated transfer of a recombinant alpha 1-antitrypsin gene to the lung epithelium in vivo," 252(5004) Science 431-4 (1991).
Rosenfeld et al., "In vivo transfer of the human cystic fibrosis transmembrane conductance regulator gene to the airway epithelium," 68(1) Cell 143-55 (1992).
Ruzheinikov et al., "High-resolution Crystal Structure of the Fab-fragments of a Family of Mouse Catalytic Antibodies with Esterase Activity," 332(2) J Mol Biol 423-35 (2003).
Salmons & Günzburg, "Targeting of retroviral vectors for gene therapy," 4(2) Human Gene Therapy 129-41 (1993).
Salomonsson et al., "Expression of the B cell-attracting chemokine CXCL13 in the target organ and autoantibody production in ectopic lymphoid tissue in the chronic inflammatory disease Sjögren's syndrome," 55(4) Scand J Immunol 336-342 (2002).
Saito et al., "Altered expression of chemokine receptor CXCR5 on T cells of myasthenia gravis patients," 170(1-2) J Neuroimmunol 172-8 (2005).
Sanger et al., "DNA sequencing with chain-terminating inhibitors," 74(12) Proc Nat'l Acad Sci USA 5463-7 (1977).
Santerre et al., "Expression of prokaryotic genes for hygromycin B and G418 resistance as dominant-selection markers in mouse L cells," 30(1-3) Gene 147-56 (1984).
Saudek et al., "A preliminary trial of the programmable implantable medication system for insulin delivery," 321(9) N Engl J Med 574-9 (1989).
Schmutz et al., "Chemokine receptors in the rheumatoid synovium: upregulation of CXCR5," 7(2) Arth Res Ther R217-R229 (2005).
Schoepfer, "The pRSET family of T7 promoter expression vectors for *Escherichia coli*," 124(1) Gene 83-5 (1993).
Scott & Smith, "Searching for peptide ligands with an epitope library," 249(4967) Science 386-90 (1990).
Sefton, "Implantable pumps," 14(3) Crit Rev Biomed Eng 201-40 (1987).
Shopes, "A genetically engineered human IgG mutant with enhanced cytolytic activity," 148(9) J Immunol 2918-22 (1992).
Short et al., "Complementary combining site contact residue mutations of the anti-digoxin Fab 26-10 permit high affinity wild-type binding," 277(19) J Biol Chem 16365-70 (2002).
Sims et al., "A humanized CD18 antibody can block function without cell destruction," 151(4) J Immunol 2296-308 (1993).
Sims et al., "Somatic hypermutation and selection of B cells in thymic germinal centers responding to acetylcholine receptor in myasthenia gravis," 167(4) J Immunol 1935-44 (2001).
Skerra & Plückthun, "Assembly of a functional immunoglobulin Fv fragment in *Escherichia coli*," 240(4855) Science 1038-41 (1988).
Smith, "Filamentous fusion phage: novel expression vectors that display cloned antigens on the virion surface," 228 (4705) Science 1315-7 (1985).
Spring & Nisonoff et al., "Allotypic markers on Fab fragments of mouse immunoglobulins," 113(2) J Immunol 470-8 (1974).
Stanfield et al., "Recurring conformation of the human immunodeficiency virus type 1 gp120 V3 loop," 315(1) Virology 159-73 (2003).
Stemple & Anderson, "Isolation of a stem cell for neurons and glia from the mammalian neural crest," 71(6) Cell 973-85 (1992).
Stevenson et al., "A chimeric antibody with dual Fc regions (bisFabFc) prepared by manipulations at the IgG hinge," 3(4) Anti-cancer Drug Des 219-30 (1989).
Strong et al., "Three-dimensional structure of murine anti-p-azophenylarsonate Fab 36-71. 1. X-ray crystallography, site-directed mutagenesis, and modeling of the complex with hapten," 30(15) Biochem 3739-45 (1991).
Studier, "Use of bacteriophage T7 lysozyme to improve an inducible T7 expression system," 219(1) J Mol Biol 37-44 (1991).
Studnicka et al., "Human-engineered monoclonal antibodies retain full specific binding activity by preserving non-CDR complementarity-modulating residues," 7(6) Protein Engineering 805-14 (1994).
Sundberg & Mariuzza, "Luxury accommodations: the expanding role of structural plasticity in protein-protein interactions," 8(7) Structure R137-R142 (2000).
Suresh et al., "Bispecific monoclonal antibodies from hybrid hybridomas," 121 Meth Enzym 210-28 (1986).
Szybalska & Szybalski, "Genetics of human cell lines IV. DNA-mediated heritable transformation of a biochemical trait," 48(12) Proc Nat'l Acad Sci USA 2026-34 (1962).
Tackenberg et al., "Clonal expansions of CD4+ B helper T cells in autoimmune myasthenia gravis," 37(3) Eur J Immunol 849-63 (2007).
Takahashi et al., "Human Fas ligand: gene structure, chromosomal location and species specificity," 6(10) Int Immunol 1567-74 (1994).
Thompson et al., "Affinity maturation of a high-affinity human monoclonal antibody against the third hypervariable loop of human immunodeficiency virus: use of phage display to improve affinity and broaden strain reactivity," 256(1) J Mol Biol 77-88 (1996).
Thornton et al., "Protein structure. Prediction of progress at last," 354 (6349) Nature 105-6 (1991).
Thorpe & Ross, "The preparation and cytotoxic properties of antibody-toxin conjugates," 62 Immunol Rev 119-58 (1982).
Thorpe, "Antibody Carriers of Cytotoxic Agents in Cancer Therapy: A Review," in Monoclonal Antibodies '84: Biological and Clinical Applications, 475-506 (Pinchera et al. eds., 1985).
Thotakura & Bahl, "Enzymatic deglycosylation of glycoproteins," 138 Meth Enzymol 350-9 (1987).
Tolstoshev, "Gene therapy, concepts, current trials and future directions," 33 Annu Rev Pharmacol Toxicol 573-96 (1993).
Traunecker et al., "Bispecific single chain molecules (Janusins) target cytotoxic lymphocytes on HIV infected cells," 10(12) EMBO J 3655-9 (1991).
Treat et al., "Liposomes in the Therapy of Infectious Disease and Cancer," 353-65 (Lopez-Berestein et al., eds., 1989).
Urlaub & Chasin, "Isolation of Chinese hamster cell mutants deficient in dihydrofolate reductase activity," 77(7) Proc Nat'l Acad Sci USA 4216-20 (1980).
Vaughan et al., "Human antibodies by design," 16(6) Nature Biotechnology 535-9 (1998).
Verhoeyen et al., "Reshaping human antibodies: grafting an antilysozyme activity," 239(4847) Science 1534-6 (1988).
Walsh et al., "Gene therapy for human hemoglobinopathies," 204(3) Proc Soc Exp Biol Med 289-300 (1993).
Wang et al., "A packaging cell line for propagation of recombinant adenovirus vectors containing two lethal gene-region deletions," 2(10) Gene Therapy 775-83 (1995).
Wang et al. "Universal PCR amplification of mouse immunoglobulin gene variable regions: the design of degenerate primers and an assessment of the effect of DNA polymerase 3' to 5' exonuclease activity," 233(1-2) J Immunol Methods 167-77 (2000).
Ward et al., "Binding activities of a repertoire of single immunoglobulin variable domains secreted from *Escherichia coli*," 341(6242) Nature 544-6 (1989).
Waterhouse et al., "Combinatorial infection and in vivo recombination: a strategy for making large phage antibody repertoires," 21(9) Nucl Acids Res 2265-6 (1993).
Webb et al., "Prevention and amelioration of collagen-induced arthritis by blockade of the CD28 co-stimulatory pathway: requirement for both B7-1 and B7-2," 26(10) Eur J Immunol 2320-28 (1996).
Wells & Lowman, "Rapid evolution of peptide and protein binding properties in vitro," 2 Curr Opin Struct Biol 597-604 (1992).

(56) References Cited

OTHER PUBLICATIONS

Wien et al., "Structure of the complex between the Fab fragment of a neutralizing antibody for type 1 poliovirus and its viral epitope," 2(3) Nat Struct Biol 232-43 (1995).

Wigler et al., "Transfer of purified herpes virus thymidine kinase gene to cultured mouse cells" 11(1) Cell 223-32 (1977).

Wigler et al., "Transformation of mammalian cells with an amplifiable dominant-acting gene," 77(6) Proc Nat'l Acad Sci USA 3567-70 (1980).

Williams et al., "Anti-tumor necrosis factor ameliorates joint disease in murine collagen-induced arthritis," 89(20) Proc Nat'l Acad Sci USA 97848 (1992).

Wilson et al., "The structure of an antigenic determinant in a protein," 37(3) Cell 767-78 (1984).

Winter & Milstein, "Man-made antibodies," 349(6307) Nature 293-9 (1991).

Wooley et al., "Influence of a recombinant human soluble tumor necrosis factor receptor FC fusion protein on type II collagen-induced arthritis in mice," 151(11) J Immunol 6602-7 (1993).

Wu & Wu, "Delivery systems for gene therapy," 3(1) Biotherapy 87-95 (1991).

Wu & Wu, "Receptor-mediated in-vitro gene transformation by a soluble DNA carrier system," 262(10) J Biol Chem 4429-32 (1987).

Yang et al., "CDR walking mutagenesis for the affinity maturation of a potent human anti-HIV-1 antibody into the picomolar range," 254(3) J Mol Biol 392-403 (1995).

Zhu et al., "Probing the antibody-catalyzed water-oxidation pathway at atomic resolution," 101(8) Proc Nat'l Acad Sci USA 2247-52 (2004).

Zhu et al., "The Origin of Enantioselectivity in Aldolase Antibodies: Crystal Structure, Site-directed Mutagenesis, and Computational Analysis," 343(5) J Mol Biol 1269-80 (2004).

Zijlstra et al., "Germ-line transmission of a disrupted beta 2-microglobulin gene produced by homologous recombination in embryonic stem cells," 342(6248) Nature 435-8 (1989).

Lopez-Berestein, "Treatment of Systemic Fungal Infections with Liposomal-Amphotericin B," in Liposomes in the Therapy of Infectious Disease and Cancer, 317-27 (Lopez-Berestein et al., eds., 1989).

Colbére-Garapin et al., "A new dominant hybrid selective marker for higher eukaryotic cells," 150(1) J Mol Biol 1-14 (1981).

Cole et al., "The EBV-Hybridoma Technique and its Application to Human Lung Cancer," in Monoclonal Antibodies and Cancer Therapy: Proceedings of the Roche-UCLA Symposium, 77-96 (Reisfeld and Sell eds., 1985).

Cote et al., "Generation of human monoclonal antibodies reactive with cellular antigens," 80(7) Proc Nat'l Acad Sci USA 2026-39 (1983).

Creighton, Proteins: Structure and Molecular Properties, W.H. Freeman &Co., San Francisco, pp. 79-86 (1st Edition, 1983).

Crouse et al., "Expression and amplification of engineered mouse dihydrofolate reductase minigenes," 3(2) Mol Cell Biol 257-66 (1983).

Cunningham & Wells, "High-resolution epitope mapping of hGH-receptor interactions by alanine-scanning mutagenesis," 244(4908) Science 1081-5 (1989).

Cunningham & Wells, "Rational design of receptor-specific variants of human growth hormone," 88(8) Proc Nat'l Acad Sci USA 3407-11 (1991).

Cwirla et al., "Peptides on phage: a vast library of peptides for identifying ligands," 87(16) Proc Nat'l Acad Sci USA 6378-82 (1990).

Davies & Riechmann, "Affinity improvement of single antibody VH domains: residues in all three hypervariable regions affect antigen binding," 2(3) Immunotechnology 169-79 (1996).

Devlin et al., "No excess of homozygosity at loci used for DNA fingerprinting," 249(4975) Science 1416-20 (1990).

Di Carlo et al., "Quilty Effect Has the Features of Lymphoid Neogenesis and Shares CXCL13—CXCR5 Pathway With Recurrent Acute Cardiac Rejections," 7(1) Am J Trans 201-10 (2007).

Duchosal et al., "Immunization of hu-PBL-SCID mice and the rescue of human monoclonal Fab fragments through combinatorial libraries," 355(6357) Nature 258-62 (1992).

During et al., "Controlled release of dopamine from a polymeric brain implant: in vivo characterization," 25(4) Ann Neurol 351-6 (1989).

Edge et al., "Deglycosylation of glycoproteins by trifluoromethanesulfonic acid," 118(1) Anal Biochem 131-7 (1981).

Fell et al., "Genetic construction and characterization of a fusion protein consisting of a chimeric F(ab') with specificity for carcinomas and human IL-2," 146(7) J Immunol 2446-52 (1991).

Fleer et al., "High-level secretion of correctly processed recombinant human interleukin-1 beta in Kluyveromyces lactis," 107(2) Gene 285-95 (1991).

Fleury et al., "A complex of influenza hemagglutinin with a neutralizing antibody that binds outside the virus receptor binding site," 6(6) Nat Struct Biol 530-34 (1999).

Foecking et al., "Powerful and versatile enhancer-promoter unit for mammalian expression vectors," 45(1) Gene 101-5 (1986).

Freedberg et al., "Flexibility and Function in HIV Protease: Dynamics of the HIV-1 Protease Bound to the Asymmetric Inhibitor Kynostatin 272 (KNI-272)," 120(31) J Am Chem Soc 7916-23 (1998).

Furukawa et al., "A role of the third complementarity-determining region in the affinity maturation of an antibody," 276(29) J Biol Chem 27622-8 (2001).

Gaffo et al., "Treatment of rheumatoid arthritis," 63(24) Am J Health Syst Pharm 2451-65 (2006).

Gallicchio & Levy, "AGBNP: an analytic implicit solvent model suitable for molecular dynamics simulations and high-resolution modeling," 25(4) J Comput Chem 479-99 (2004).

Garrard et al., "Fab assembly and enrichment in a monovalent phage display system," 9(12) Biotechnology 1373-7 (1991).

Gefter et al. "A simple method for polyethylene glycol-promoted hybridization of mouse myeloma cells," 3(2) Somatic Cell Genet 231-36 (1977).

Gentz et al., "Bioassay for trans-activation using purified human immunodeficiency virus tat-encoded protein: trans-activation requires mRNA synthesis," 86(3) Proc Nat'l Acad Sci USA 821-4 (1989).

Gillies et al., "Antibody-targeted interleukin 2 stimulates T-cell killing of autologous tumor cells," 89(4) Proc Nat'l Acad Sci USA 1428-32 (1992).

Gillies et al., "High-level expression of chimeric antibodies using adapted cDNA variable region cassettes," 125(1-2) J Immunol Methods 191-202 (1989).

Goding, "Production of Monoclonal Antibodies," in Monoclonal Antibodies: Principles and Practice, Chapter 3:59-103 (2nd Ed., 1986).

Goeddel et al., "Direct expression in *Escherichia coli* of a DNA sequence coding for human growth hormone," 281 (5732) Nature 544-8 (1979).

Goeddel et al., "Synthesis of human fibroblast interferon by *E. coli*," 8(18) Nucl Acids Res 4057-74 (1980).

Goldspiel et al., "Human gene therapy," 12(7) Clinical Pharm 488-505 (1993).

Gram et al., "In vitro selection and affinity maturation of antibodies from a naive combinatorial immunoglobulin library," 89(8) Proc Nat'l Acad Sci USA 3576-80 (1992).

Greenspan & Bona, "Idiotypes: structure and immunogenicity," 7(5) FASEB J 437-444 (1993).

Grossman & Wilson, "Retroviruses: delivery vehicle to the liver," 3(1) Curr Opin Genet Dev 110-4 (1993).

Grünberg et al., "Flexibility and conformational entropy in protein-protein binding," 14(12) Structure 683-93 (2006).

Guddat et al., "Local and Transmitted Conformational Changes on Complexation of an Anti-sweetener Fab," 236(1) J Mol Biol 247-74 (1994).

Guss et al., "Structure of the IgG-binding regions of streptococcal protein G," 5(7) EMBO J 1567-75 (1986).

Hakimuddin et al., "A chemical method for deglycosylation of proteins," 259(1) Arch Biochem Biophys 52-7 (1987).

(56) References Cited

OTHER PUBLICATIONS

Ham & McKeehan, "Media and growth requirements," 58 Meth Enzymol 44-93 (1979).
Harris et al., "Commercial manufacturing scale formulation and analytical characterization of therapeutic recombinant antibodies," 61(3) Drug Dev Res 137-54 (2004).
Hawkins et al., "Selection of phage antibodies by binding affinity: Mimicking affinity maturation," 226(3) J Mol Biol 889-96 (1992).
Hellström et al., "Antibodies for Drug Delivery," in Controlled Drug Delivery: Fundamentals and Applications, Chapter 15:623-53 (Robinson & Lee eds., 2nd ed. 1987).
Hinnen et al., "Transformation of yeast," 75(4) Proc Nat'l Acad Sci USA 1929-33 (1978).
Hitzeman et al., "Isolation and characterization of the yeast 3-phosphoglycerokinase gene (PGK) by an immunological screening technique," 255(24) J Biol Chem 12073-80 (1980).
Ho et al., "Site-directed mutagenesis by overlap extension using the polymerase chain reaction," 77(1) Gene 51-9 (1989).
Holland & Holland, "Isolation and identification of yeast messenger ribonucleic acids coding for enolase, glyceraldehyde-3-phosphate dehydrogenase, and phosphoglycerate kinase," 17(23) Biochemistry 4900-7 (1978).
Horton et al., "Gene splicing by overlap extension: tailor-made genes using the polymerase chain reaction," 8(5) BioTechniques 528-35 (1990).
Howard et al., "Intracerebral drug delivery in rats with lesion-induced memory deficits," 71(1) J Neurosurg 105-12 (1989).
Hudson, "Recombinant antibody constructs in cancer therapy," 11(5) Current Opinion in Immunology 548-57 (1999).
Huston et al., "Protein engineering of antibody binding sites: recovery of specific activity in an anti-digoxin single-chain Fv analogue produced in *Escherichia coli*," 85(16) Proc Nat'l Acad Sci USA 5879-83 (1988).
International Search Report in International Application No. PCT/US2008/74381, mailed Nov. 19, 2008.
International Preliminary Report on Patentability in International Application No. PCT/US2008/074381, report issued Mar. 2, 2010.
Adey et al., Chapter 16, "Preparation of Second-Generation Phage Libraries", pp. 277-291, Phage Display of Peptides and Proteins, A Laboratory Manual, eds. Kay et al., Academic Press (1996).
Aloisi & Pujol-Borrell, "Lymphoid neogenesis in chronic inflammatory diseases," 6(3) Nat Rev Immunol 205-17 (2006).
Amit et al., "Three-dimensional structure of an antigen-antibody complex at 2.8 A resolution," 233(4765) Science 747-53 (1986).
Arnon et al., "Monoclonal Antibodies for Immunotargeting of Drugs in Cancer Therapy" in Monoclonal Antibodies and Cancer Therapy: Proceedings of the Roche-UCLA Symposium, 243-56 (Reisfeld and Sell eds.,1985).
Angal et al., "A single amino acid substitution abolishes the heterogeneity of chimeric mouse/human (IgG4) antibody," 30(1) Mol Imm 105-8 (1993).
Aplin & Wriston, "Preparation, properties, and applications of carbohydrate conjugates of proteins and lipids," 10 (4) CRC Crit Rev Biochem 259-306 (1981).
Baddoura et al., "Lymphoid neogenesis in murine cardiac allografts undergoing chronic rejection," 5(3) Am J Trans 510-6 (2005).
Banfield et al., "VL:VH domain rotations in engineered antibodies: Crystal structures of the Fab fragments from two murine antitumor antibodies and their engineered human constructs," 29(2) Proteins 161-71 (1997).
Barbas et al., "In vitro evolution of a neutralizing human antibody to human immunodeficiency virus type 1 to enhance affinity and broaden strain cross-reactivity," 91(9) Proc Nat'l Acad Sci USA 3809-13 (1994).
Barbas et al., "Assembly of combinatorial antibody libraries on phage surfaces: the gene III site," 88(18) Proc Nat'l Acad Sci USA 7978-82 (1991).
Barone et al., "Association of CXCL13 and CCL21 expression with the progressive organization of lymphoid-like structures in Sjögren's syndrome," 52(6) Arth Rheum 1773-84 (2005).

Barth et al., "Algorithms for constrained molecular dynamics," 16(10) J Comp Chem 1192-1209 (1995).
Barnes & Sato et al., "Methods for growth of cultured cells in serum-free medium," 102(2) Anal Biochem 255-70 (1980).
Bentley et al., "Three-dimensional structure of an idiotope—anti-idiotope complex," 348(6298) Nature 254-7 (1990).
Berman et al., "The Protein Data Bank," 28(1) Nucleic Acids Research 235-42 (2000).
Beuscher IV et al., "Structure and Dynamics of Blue Fluorescent Antibody 19G2 at Blue and Violet Fluorescent Temperatures," (To be published).
Birch & Racher, "Antibody production," 58(5-6) Adv Drug Del Rev 671-685 (2006).
Bird et al, "Single-chain antigen-binding proteins," 242(4877) Science 423-6 (1988).
Bizebard et al., "Refined three-dimensional structure of the Fab fragment of a murine IgGI,lambda antibody," D50 (Part5) Acta Crystallogr D Biol Crystallogr 768-77 (1994).
Bhat et al., "Bound water molecules and conformational stabilization help mediate an antigen-antibody association," 91(3) Proc Nat'l Acad Sci USA 1089-93 (1994).
Blythe & Flower, "Benchmarking B cell epitope prediction: Underperformance of existing methods," 14(1) Protein Science 246-8 (2005).
Boder et al., "Directed evolution of antibody fragments with monovalent femtomolar antigen-binding affinity," 97(20) Proc Nat'l Acad Sci USA 10701-5 (2000).
Boerner et al., "Production of antigen-specific human monoclonal antibodies from in vitro-primed human splenocytes," 147(1) J Immunol 86-95 (1991).
Bout et al., "Lung gene therapy: in vivo adenovirus-mediated gene transfer to rhesus monkey airway epithelium," 5(1) Human Gene Therapy 3-10 (1994).
Brennan et al., "Preparation of bispecific antibodies by chemical recombination of monoclonal immunoglobulin G1 fragments," 229(4708) Science 813 (1985).
Brodeur et al., "Mouse-Human Myeloma Partners for the Production of Heterohybridomas," in Monoclonal Antibody Production Techniques and Applications, Chapter4:51-63 (LB Schook ed. 1st ed. 1987).
Brooks et al., "CHARMM: A program for macromolecular energy, minimization, and dynamics calculations," 4(2) J Computational Chemistry 187-217 (1983).
Brown et al., "The Structural Basis of Repertoire Shift in an Immune Response to Phosphocholine," 191(12) J Exp Med 2101-12 (2000).
Brüggemann et al., "Designer mice: the production of human antibody repertoires in transgenic animals," 7 The Year in Immunol 33-40 (1993).
Buchwald et al., "Long-term, continuous intravenous heparin administration by an implantable infusion pump in ambulatory patients with recurrent venous thrombosis," 88(4) Surgery 507-16 (1980).
Bürkle et al., "Overexpression of the CXCR5 chemokine receptor, and its ligand, CXCL13 in B-cell chronic lymphocytic leukemia," 110(9) Blood 3316-3325 (2007).
Cañete et al., "Ectopic lymphoid neogenesis in psoriatic arthritis," 66(6) Ann Rheum Dis 720-6 (2007).
Carlsen et al., "B cell attracting chemokine 1 (CXCL13) and its receptor CXCR5 are expressed in normal and aberrant gut associated lymphoid tissue," 51(3) Gut 364-71 (2002).
Caron et al., "Engineered humanized dimeric forms of IgG are more effective antibodies," 176(4) J Exp Med 1191-5 (1992).
Carter et al., "Humanization of an anti-p185HER2 antibody for human cancer therapy," 89(10) Proc Nat'l Acad Sci USA 4285-9 (1992).
Carter et al., "High level *Escherichia coli* expression and production of a bivalent humanized antibody fragment," 10 (2) Biotechnology 163-7 (1992).
Case et al., "The Amber biomolecular simulation programs," 26(16) J Computational Chemistry 1668-88 (2005).
Celikel et al., "von Willebrand factor conformation and adhesive function is modulated by an internalized water molecule," 7(10) Nat Struct Biol 881-4 (2000).

(56) References Cited

OTHER PUBLICATIONS

Celikel et al., "Crystal structure of the von Willebrand factor A1 domain in complex with the function blocking NMC-4 Fab," 5(3) Nat Struct Biol 189-94 (1998).
Chang et al., "Phenotypic expression in *E. coli* of a DNA sequence coding for mouse dihydrofolate reductase," 275 (5681) Nature 615-24 (1978).
Chardés et al., "Efficient amplification and direct sequencing of mouse variable regions from any immunoglobulin gene family," 452(3) FEBS Letters 386-394 (1999).
Chothia et al., "Canonical structures for the hypervariable regions of immunoglobulins," 196(4) J Mol Biol 901-17 (1987).
Cieplak et al., "Molecular mechanical models for organic and biological systems going beyond the atom centered two body additive approximation: aqueous solution free energies of methanol and N-methyl acetamide, nucleic acid base, and amide hydrogen bonding and chloroform/water partition coefficients of the nucleic acid bases," 22(10) J Comp Chem 1048-57 (2001).
Clackson et al., "Making antibody fragments using phage display libraries," 352(6336) Nature 624-28 (1991).
Cline, "Perspectives for gene therapy: inserting new genetic information into mammalian cells by physical techniques and viral vectors," 29(1) Pharmacol Ther 69-92 (1985).
Clowes et al., "Long-term biological response of injured rat carotid artery seeded with smooth muscle cells expressing retrovirally introduced human genes," 98(2) J Clin Invest 644-51 (1994).
Cockett et al., "High level expression of tissue inhibitor of metalloproteinases in Chinese hamster ovary cells using glutamine synthetase gene amplification," 8(7) Biotechnology 662-7 (1990).
Cotten et al., "Receptor-mediated transport of DNA into eukaryotic cells," 217 Meth Enzymol 618-644 (1993).
Search report and written opinion of the Hungarian Intellectual Property Office for Singapore Patent Application No. 201001145-0, search completed Jul. 5, 2012.
Emrich et al., "Transmembrane topology of the lymphocyte-specific G-protein-coupled receptor BLR1: analysis by flow cytometry and immunocytochemistry," Cell. Mol. Biol. 40(3):413-19 (1994).
Forster et al., "A general method for screening mAbs specific for G-protein coupled receptors as exemplified by using epitope tagged BLR1-transfected 293 cells and solid-phase cell ELISA," Biochemical Biophysical Research Communications 196(3):1496-1503 (1993).
Clark "Antibody humanization: a case of the 'Emperor's new clothes'?" Immunol Today 21(8):397-402 (2000).
Legler et al., "B cell-attracting chemokine 1, a human CXC chemokine expressed in lymphoid tissues, selectively attracts B lymphocytes via BLR1/CXCR5," J Exp Med. 187(4): 655-60 (1998).
Lisignoli et al., "Human osteoblasts express functional CXC chemokine receptors 3 and 5: activation by their ligands, CXCL10 and CXCL13, significantly induces alkaline phosphatase and beta-N-acetylhexosaminidase release," J Cell Physiol. 194(1):71-79 (2003).
Roitt A. et al. "Immunology", Moscow, Mir, pp. 110-111 (2000).

Spinetti et al., "The chemokine CXCL13 (BCA-1) inhibits FGF-2 effects on endothelial cells," Biochem Biophys Res Commun. 289(1):19-24 (2001).
Casset et al. "A peptide mimetic of an anti-CD4 monoclonal antibody by rational design." Biochem Biophys Res Commun. 307(1):198-205 (2003).
Chen et al., "Selection and analysis of an optimized anti-VEGF antibody: crystal structure of an affinity-matured Fab in complex with antigen." J. Mol. Biol. 293(4):865-81 (1999).
DePascalis et al., "Grafting of "abbreviated" complementarity-determining regions containing specificity-determining residues essential for ligand contact to engineer a less immunogenic humanized monoclonal antibody." J Immunol.169(6):3076-84 (2002).
Lamminmaki & Kankare, "Crystal structure of a recombinant anti-estradiol Fab fragment in complex with 17beta-estradiol." J Biol Chem. 276(39):36687-94 (2001).
MacCallum et al., "Antibody-antigen interactions: contact analysis and binding site topography." J. Mol. Biol. 262(5):732-45 (1996).
Padlan et al., "Structure of an antibody-antigen complex: crystal structure of the HyHEL-10 Fab-lysozyme complex." Proc Natl Acad Sci U.S.A. 86(15):5938-42 (1989).
Rudikoff et al., "Single amino acid substitution altering antigen-binding specificity." Proc Natl Acad Sci U.S.A. 79(6):1979-83 (1982).
Vajdos et al., "Comprehensive functional maps of the antigen-binding site of an anti-ErbB2 antibody obtained with shotgun scanning mutagenesis." J. Mol. Biol. 320(2):415-28 (2002).
Wu et al., "Humanization of a murine monoclonal antibody by simultaneous optimization of framework and CDR residues." J. Mol. Biol. 294(1):151-62 (1999).
Beuscher IV et al., "Structure and Dynamics of Blue Fluorescent Antibody 19G2 at Blue and Violet Fluorescent Temperatures," (reference cited on PDBj.org retrieved Feb. 21, 2012; pp. 1-2).
Marks et al., "X-Ray Structures of D1.3 Fv Mutants," PDB ID; 1A7P (reference cited on PDBj.org retrieved Feb. 21, 2012; pp. 1-2).
Pozharski et al., "Carving a Binding Site: Structural Study of an Anti-Cocaine Antibody" in "Complex with Three Cocaine Analogs," (reference cited on PDBj.org retrieved Feb. 21, 2012; pp. 1-2).
Ito et al., "Defective B1 cell homing to the peritoneal cavity and preferential recruitment of B1 cells in the target organs in a murine model for systemic lupus erythematosus," J. Immunol. 172(6):3628-34 (2004).
Padlan et al., "Identification of specificity-determining residues in antibodies." FASEB J. 9(1):133-39 (1995).
Phumyen et al., "Improved binding activity of antibodies against major histocompatibility complex class I chain-related gene A by phage display technology for cancer-targeted therapy." J Biomed Biotechnol. 2012:597647 (Epub Nov. 21, 2012; pp. 1-8).
Tamura et al., "Structural correlates of an anticarcinoma antibody: identification of specificity-determining residues (SDRs) and development of a minimally immunogenic antibody variant by retention of SDRs only." J Immunol. 164(3):1432-41 (2000).
Holt et al., "Domain antibodies: proteins for therapy," TRENDS in Biotechnology, 21(11):484-90 (2003).
Little et al., "Of mice and men: hybridoma and recombinant antibodies" Immunology Today, 21(8):364-70 (2000).

\* cited by examiner

HUMANIZED ANTI-CXCR5 ANTIBODIES, DERIVATIVES THEREOF AND THEIR USE

This application is a division of U.S. application Ser. No. 12/675,799, filed Oct. 25, 2010, which was a national stage application under 35 U.S.C. § 371 of International Application No. PCT/US2008/074381, filed Aug. 27, 2008, which claims the benefit of U.S. Provisional Application No. 60/968,792, filed Aug. 29, 2007, the disclosures of each of which are explicitly incorporated by reference herein.

FIELD OF THE INVENTION

The present invention relates to anti-CXCR5 antibodies and their use in the amelioration, treatment or prevention of diseases or disorders in mammals, including humans, resulting from improper CXCR5 activity or metabolism, or the inappropriate or adventitious use thereof, for example, by a pathogen. An antibody of interest may block engagement of a ligand, such as CXCL13, with it receptor, such as, CXCR5. Prophylactic, immunotherapeutic and diagnostic compositions comprising the antibodies and derivatives thereof of interest and their use in methods for preventing or treating diseases in mammals, including humans, caused by inappropriate metabolism and/or activity of CXCR5$^+$ cells, such as B lymphocytes, also are disclosed. Such diseases include autoimmune deficiencies and diseases caused by or characterized by inflammation, such as rheumatoid arthritis (RA), where CXCR5 is up-regulated.

BACKGROUND

CXCR5, also known as Burkitt lymphoma receptor (BLR1), CD185, MDR15 and MGC117347, is a G protein-coupled receptor which is a member of the CXC chemokine receptor family. A ligand is BLC, also known as CXCL13, which is a B cell chemoattractant.

The unprocessed CXCR5 precursor is 372 amino acids in length with a molecular weight of 42 $K_D$.

CXCR5 has a role in B cell migration and localization within particular anatomic compartments. Knockout mice lack peripheral lymph nodes, have fewer Peyer's patches and have decreased B cell levels.

SUMMARY

The present invention provides novel humanized and human antibodies, and fragments and derivatives thereof, that specifically bind to CXCR5. Some of the antibodies, and CXCR5-binding fragments thereof, can be altered to prevent intrachain disulfide bond formation resulting in a molecule that is stable through manufacturing and use in vivo. Other antibodies of interest can be altered to minimize binding to $F_c R$. Some CXCR5 antibodies of interest compete with CXCL13 for binding to CXCR5. Other antibodies diminish CXCR5 activity.

The invention includes the amino acid sequences of the variable heavy and light chain of the antibodies and their corresponding nucleic acid sequences.

Another embodiment of the invention includes the complementarity determining regions (CDR) sequences of the antibodies to obtain binding molecules that comprise one or more CDR regions, or CDR-derived regions, that retain CXCR5-binding capacity of the parent molecule from which the CDR was(were) obtained.

An antibody of interest can be one that prevents CXCL13, or other ligand, binding to CXCR5$^+$ cells, such as B cells.

Another embodiment of the present invention includes the cell lines and vectors harboring the antibody sequences of the present invention.

Another embodiment of the present invention is the use of the antibodies for the preparation of a medicament or composition for the treatment of diseases and disorders associated with CXCR5 function and metabolism.

Another embodiment of the present invention is the use of these antibodies in the treatment of disorders associated with atypical or abnormal CXCR5 biology and function.

Additional features and advantages are described herein, and will be apparent from, the following Detailed Description.

DETAILED DESCRIPTION

This invention is not limited to the particular methodology, protocols, cell lines, vectors, or reagents described herein because they may vary without departing from the spirit and scope of the invention. Further, the terminology used herein is for the purpose of exemplifying particular embodiments only and is not intended to limit the scope of the present invention. Unless defined otherwise, all technical and scientific terms and any acronyms used herein have the same meanings as commonly understood by one of ordinary skill in the art in the field of the invention. Any method and material similar or equivalent to those described herein can be used in the practice of the present invention and only exemplary methods, devices, and materials are described herein.

All patents and publications mentioned herein are incorporated herein in entirety by reference for the purpose of describing and disclosing the proteins, enzymes, vectors, host cells and methodologies reported therein that might be used with and in the present invention. However, nothing herein is to be construed as an admission that the invention is not entitled to antedate such disclosure by virtue of prior invention.

Prior to teaching the making and using of the CXCR5-related methods and products of interest, the following non-limiting definitions of some terms and phrases are provided to guide the artisan.

"CXCR5" relates to the naturally occurring, known molecule found on lymphocytes, particularly B cells, and particularly naïve B cells; to such a molecule isolated from such cells; to such a molecule manufactured recombinantly using known materials and means, and using a nucleic acid encoding a CXCR5; as well as to portions of CXCR5, such as the extracellular (EC) domain, which retains the characteristics and properties relevant to the practice of the instant invention, such as CXCL13 binding. A soluble CXCR5 molecule can consist essentially of the EC domain of CXCR5, which includes, generally, about the first sixty amino acids of the molecule, that is, the amino terminal portion of CXCR5.

CXCR5 is a non-promiscuous receptor. CXCL13 is a ligand of CXCR5 and is expressed constitutively on stromal cells, such as follicular dendritic cells, and in lymphoid tissues. CXCL13 specifically attracts B cells and a small subset of T cells called B helper follicular T cells, TFH. That may not be unexpected given the many interactions between T cell and B cell populations in the immune system. Moreover, activated T cell induces or upregulate CXCR5 expression. Infiltration of lymphocytes into tertiary, ectopic germinal centers (GCs) has been found to correlate well with increased disease severity and tolerance breakdown in certain disorders which preset with such atypical lymph node-like structures. Using in vivo murine models, such as CXCR5−/− and CXCL13−/− mice, the absence of either the receptor or the ligand results in an altered GC fine architecture due to altered T and B cell localization, and possibly interaction. These mice are also protected against developing severe collagen-induced arthritis (CIA). As CXCR5 is selectively expressed on mature B cells, which are linked to the pathogenesis of RA, blocking this receptor will modulate the arthritogenic response in affected individuals. Rheumatoid arthritis treatment with biologics (i.e., anti-TNFα and anti-CD20 antibodies, Rituximab) has shown to be clinically effective; in particular, patients on B cell-directed therapy have shown long-lasting improvements in clinical signs and symptoms. Selective targeting of CXCR5, which is only expressed on mature B cells and B helper T cells, will not affect B cell development or immunocompromise the patient. Unlike Rituximab, an instant antibody is a neutralizing antibody that does not mediate cell cytotoxicity.

A "CXCR5 disease" is a malady, disorder, disease, condition, abnormality and so on, which is characterized by or caused by overexpression or increased levels of CXCL13 or other CXCR5 ligand, increased levels of B cells, increased levels of B cell activity, increased levels of CXCR5 or improper metabolism and activity of CXCR5.

By "B cell activity" is meant higher than normal B cell levels, which can be local, or evidence of a biological manifestation or function of a B cell, such as antibody expression, Bruton's tyrosine kinase presence or activity, expression or presence of CD19, expression or presence of B cell activating factor and so on.

The phrase "substantially identical" with respect to an antibody chain polypeptide sequence may be construed as an antibody chain exhibiting at least 70%, 80%, 90%, 95% or more sequence identity to the reference polypeptide sequence. The term with respect to a nucleic acid sequence may be construed as a sequence of nucleotides exhibiting at least about 85%, 90%, 95%, 97% or more sequence identity to the reference nucleic acid sequence.

The terms, "identity" or "homology" may mean the percentage of nucleotide bases or amino acid residues in the candidate sequence that are identical with the residue of a corresponding sequence to which it is compared, after aligning the sequences and introducing gaps, if necessary, to achieve the maximum percent identity for the entire sequence, and not considering any conservative substitutions as part of the sequence identity. Neither N-terminal or C-terminal extensions nor insertions shall be construed as reducing identity or homology. Methods and computer programs for the alignment are available and well known in the art. Sequence identity may be measured using sequence analysis software.

The phrases and terms "functional fragment, variant, derivative or analog" and the like, as well as forms thereof, of an antibody or antigen is a compound or molecule having qualitative biological activity in common with a full-length antibody or antigen of interest. For example, a functional fragment or analog of an anti-CXCR5 antibody is one which can bind to a CXCR5 molecule or one which can prevent or substantially reduce the ability of a ligand, such as CXCL13, or an agonistic or antagonistic antibody, to bind to CXCR5. An example is an scF$_V$ molecule. As to CXCR5, a variant or derivative thereof is a molecule that is not identical to a naturally occurring CXCR5 and yet can be used for a purpose of the instant invention, such as, while not identical to the wild type CXCR5 nevertheless can be used as immunogen to raise antibodies that selectively bind to wild type CXCR5.

"Substitutional" variants are those that have at least one amino acid residue in a native sequence removed and replaced with a different amino acid inserted in its place at the same position. The substitutions may be single, where only one amino acid in the molecule is substituted, or may be multiple, where two or more amino acids are substituted in the same molecule. The plural substitutions may be at consecutive sites. Also, one amino acid can be replaced with plural residues, in which case such a variant comprises both a substitution and an insertion. "Insertional" variants are those with one or more amino acids inserted immediately adjacent to an amino acid at a particular position in a native sequence. Immediately adjacent to an amino acid means connected to either the α-carboxyl or α-amino functional group of the amino acid. "Deletional" variants are those with one or more amino acids in the native amino acid sequence removed. Ordinarily, deletional variants will have one or two amino acids deleted in a particular region of the molecule.

The term "antibody" is used in the broadest sense, and specifically covers monoclonal antibodies (including full length monoclonal antibodies), polyclonal antibodies, multispecific antibodies (e.g., bispecific antibodies), antibody fragments or synthetic polypeptides carrying one or more CDR or CDR-derived sequences so long as the polypeptides exhibit the desired biological activity. Antibodies (Abs) and immunoglobulins (Igs) are glycoproteins having the same structural characteristics. Generally, antibodies are considered Igs with a defined or recognized specificity. Thus, while antibodies exhibit binding specificity to a specific target, immunoglobulins include both antibodies and other antibody-like molecules which lack target specificity. The antibodies of the invention can be of any class (e.g., IgG, IgE, IgM, IgD, IgA and so on), or subclass (e.g., IgG$_1$, IgG$_2$, IgG$_{2a}$, IgG$_3$, IgG$_4$, IgA$_1$, IgA$_2$ and so on) ("type" and "class", and "subtype" and "subclass", are used interchangeably herein). Native or wildtype, that is, obtained from a non-artificially manipulated member of a population, antibodies and immunoglobulins are usually heterotetrameric glycoproteins of about 150,000 daltons, composed of two identical light (L) chains and two identical heavy (H) chains. Each heavy chain has at one end a variable domain (V$_H$) followed by a number of constant domains. Each light chain has a variable domain at one end (V$_L$) and a constant domain at the other end. By "non-artificially manipulated" is meant not treated to contain or express a foreign antigen binding molecule. Wildtype can refer to the most prevalent allele or species found in a population or to the antibody obtained from a non-manipulated animal, as compared to an allele or polymorphism, or a variant or derivative obtained by a form of manipulation, such as mutagenesis, use of recombinant methods and so on to change an amino acid of the antigen-binding molecule.

As used herein, "anti-CXCR5 antibody" means an antibody or polypeptide derived therefrom (a derivative) which binds specifically to human CXCR5 as defined herein, including, but not limited to, molecules which inhibit or substantially reduce the binding of CXCR5 to its ligands or inhibit CXCR5 activity.

The term "variable" in the context of a variable domain of antibodies, refers to certain portions of the pertinent molecule which differ extensively in sequence between and among antibodies and are used in the specific recognition and binding of a particular antibody for its particular target. However, the variability is not evenly distributed through the variable domains of antibodies. The variability is concentrated in three segments called complementarity determining regions (CDRs; i.e., CDR1, CDR2, and CDR3) also known as hypervariable regions, both in the light chain and the heavy chain variable domains. The more highly conserved portions of variable domains are called the framework (FR) regions or sequences. The variable domains of native heavy and light chains each comprise four FR regions, largely adopting a β-sheet configuration, connected by three CDRs, which form loops connecting, and in some cases forming part of, the β-sheet structure. The CDRs in each chain are held together often in proximity by the FR regions and, with the CDRs from the other chain, contribute to the formation of the target (epitope or determinant) binding site of antibodies (see Kabat et al. Sequences of Proteins of Immunological Interest, National Institute of Health, Bethesda, Md. (1987)). As used herein, numbering of immunoglobulin amino acid residues is done according to the immunoglobulin amino acid residue numbering system of Kabat et al., unless otherwise indicated. One CDR can carry the ability to bind specifically to the cognate epitope.

The term "antibody fragment" refers to a portion of an intact or a full-length chain or an antibody, generally the target binding or variable region. Examples of antibody fragments include, but are not limited to, $F_{ab}$, $F_{ab'}$, $F_{(ab')2}$ and $F_v$ fragments. A "functional fragment" or "analog of an anti-CXCR5 antibody" is one which can prevent or substantially reduce the ability of the receptor to bind to a ligand or to initiate signaling. As used herein, functional fragment generally is synonymous with, "antibody fragment" and with respect to antibodies, can refer to fragments, such as $F_v$, $F_{ab}$, $F_{(ab')2}$ and so on which can prevent or substantially reduce the ability of the receptor to bind to a ligand or to initiate signaling. An "$F_v$" fragment consists of a dimer of one heavy and one light chain variable domain in a non-covalent association ($V_H$-$V_L$ dimer). In that configuration, the three CDRs of each variable domain interact to define a target binding site on the surface of the $V_H$-$V_L$ dimer, as in an intact antibody. Collectively, the six CDRs confer target binding specificity on the intact antibody. However, even a single variable domain (or half of an $F_v$ comprising only three CDRs specific for a target) can have the ability to recognize and to bind target.

"Single-chain $F_v$," "s$F_v$," or "scAb" antibody fragments comprise the $V_H$ and $V_L$ domains of an antibody, wherein these domains are present in a single polypeptide chain. Generally, the $F_v$ polypeptide further comprises a polypeptide linker, often a flexible molecule, between the $V_H$ and $V_L$ domains, which enables the sFv to form the desired structure for target binding.

The term "diabodies" refers to antibody fragments with two antigen-binding sites, which fragments can comprise a heavy chain variable domain ($V_H$) connected to a light chain variable domain ($V_L$) in the same polypeptide chain. By using a linker that is too short to allow pairing between the two variable domains on the same chain, the diabody domains are forced to pair with the binding domains of another chain to create two antigen-binding sites.

The $F_{ab}$ fragment contains the variable and constant domains of the light chain and the variable and first constant domain ($C_{H1}$) of the heavy chain. $F_{ab'}$ fragments differ from $F_{ab}$ fragments by the addition of a few residues at the carboxyl terminus of the $C_{H1}$ domain to include one or more cysteines from the antibody hinge region. $F_{ab'}$ fragments can be produced by cleavage of the disulfide bond at the hinge cysteines of the $F_{(ab')2}$ pepsin digestion product. Additional enzymatic and chemical treatments of antibodies can yield other functional fragments of interest.

The term "monoclonal antibody" as used herein refers to an antibody obtained from a population of substantially homogeneous antibodies, i.e., the individual antibodies comprising the population are identical except for possible naturally occurring mutations that may be present in minor amounts.

Monoclonal antibodies herein specifically include "chimeric" antibodies in which a portion of the heavy and/or light chain is identical with or homologous to corresponding sequences in antibodies derived from a particular species or belonging to a particular antibody class or subclass (type or subtype), with the remainder of the chain(s) identical with or homologous to corresponding sequences in antibodies derived from another species or belonging to another antibody class or subclass, as well as fragments of such antibodies, so long as they exhibit the desired biological activity of binding to CXCR5 or impacting CXCR5 activity or metabolism (U.S. Pat. No. 4,816,567; and Morrison et al., Proc Natl Acad Sci USA 81:6851 (1984)). Thus, CDRs from one class of antibody can be grafted into the FR of an antibody of different class or subclass.

Monoclonal antibodies are highly specific, being directed against a single target site, epitope or determinant. Furthermore, in contrast to conventional (polyclonal) antibody preparations which typically include different antibodies directed against different determinants (epitopes) of an antigen, each monoclonal antibody is directed against a single determinant on the target. In addition to their specificity, monoclonal antibodies are advantageous being synthesized by a host cell, uncontaminated by other immunoglobulins, and provides for cloning the relevant gene and mRNA encoding the antibody of chains thereof. The modifier "monoclonal" indicates the character of the antibody as being obtained from a substantially homogeneous population of antibodies, and is not to be construed as requiring production of the antibody by any particular method. For example, the monoclonal antibodies for use with the present invention may be isolated from phage antibody libraries using well known techniques or can be purified from a polyclonal prep. The parent monoclonal antibodies to be used in accordance with the present invention may be made by the hybridoma method described by Kohler et al., Nature 256:495 (1975), or may be made by recombinant methods well known in the art.

"Humanized" forms of non-human (e.g., murine) antibodies are chimeric immunoglobulins, immunoglobulin chains or fragments thereof (such as $F_v$, $F_{ab}$, $F_{ab'}$, $F_{(ab')2}$ or other target-binding subsequences of antibodies) which contain sequences derived from non-human immunoglobulin, as compared to a human antibody. In general, the humanized antibody will comprise substantially all of one, and typically two, variable domains, in which all or substantially all of the CDR regions correspond to those of a non-human immunoglobulin and all or substantially all of the FR regions are those of a human immunoglobulin template sequence. The humanized antibody may also comprise at least a portion of an immunoglobulin constant region ($F_c$), typically that of the human immunoglobulin template chosen. In general, the goal is to have an antibody molecule that is minimally immunogenic in a human. Thus, it is possible that one or more amino acids in one or more CDRs also can be changed to one that is less immunogenic to a human host, without substantially minimizing the specific binding function of the one or more CDRs to CXCR5 or to CXCL13. Alternatively, the FR can be non-human but those amino acids most immunogenic are replaced with ones less immunogenic. Nevertheless, CDR grafting, as discussed above, is not the only way to obtain a humanized antibody. For example, modifying just the CDR regions may be insufficient as it is not uncommon for framework residues to have a role in determining the three-dimensional structure of the CDR loops and the overall affinity of the antibody for its ligand. Hence, any means can be practiced so that the non-human parent antibody molecule is modified to be one that is less immunogenic to a human, and global sequence identity with a human antibody is not always a necessity. So, humanization also can be achieved, for example, by the mere substitution of just a few residues, particularly those which are exposed on the antibody molecule and not buried within the molecule, and hence, not readily accessible to the host immune system. Such a method is taught herein with respect to substituting "mobile" or "flexible" residues on the antibody molecule, the goal being to reduce or dampen the immunogenicity of the resultant molecule without comprising the specificity of the antibody for its epitope or determinant. See, for example, Studnicka et al., Prot Eng 7(6)805-814, 1994; Mol Imm 44:1986-1988, 2007; Sims et al., J Immunol 151:2296 (1993); Chothia et al., J Mol Biol 196:901 (1987); Carter et al., Proc Natl Acad Sci USA 89:4285 (1992); Presta et al., J Immunol 151:2623 (1993), WO 2006/042333 and U.S. Pat. No. 5,869,619.

The adaptive immune response has two major arms: the cellular immune response of T lymphocytes and the humoral immune response of antibody secreting B lymphocytes. B cell epitopes can be linear, contiguous amino acids, or can be conformational (Protein Science (2005) 14, 246). In contrast, T-cell epitopes are short linear peptides that are cleaved from antigenic proteins that are presented in the context of major histocompatibility complex (MHC) proteins, or, in case of humans, human leukocyte antigen (HLA) class I or class II molecules. Epitope presentation depends on both MHC-peptide binding and T cell receptor (TCR) interactions. MHC proteins are highly polymorphic, and each binds to a limited set of peptides. Thus, the particular combination of MHC alleles present in a host limits the range of potential epitopes recognized during an infection.

Two fundamental types of T cells are distinguished by expression of CD8 and CD4 proteins, which dictate whether a T cell will recognize epitopes presented by class I or class II molecules, respectively. CD4$^+$ T epitopes are processed after encapsulation by antigen presenting cells in membrane bound vesicles, where the antigen is degraded by proteases into peptide fragments that bind to MHC class II proteins. In contrast, CD8$^+$ T cells generally recognize viral or self-antigens expressed from within a cell, proteins that are cleaved into short peptides in the cytosol by the immunoproteasome. After cleavage, peptides are translocated by the transporter associated with antigen processing (TAP) into the endoplasmic reticulum for loading onto HLA I antigens. CD4$^+$ T (helper) cell epitopes are critical in driving T cell-dependent immune responses to protein antigens.

A humanization method of interest is based on the impact of the molecular flexibility of the antibody during and at immune recognition. Protein flexibility is related to the molecular motion of the protein molecule. Protein flexibility is the ability of a whole protein, a part of a protein or a single amino acid residue to adopt an ensemble of conformations which differ significantly from each other. Information about protein flexibility can be obtained by performing protein X-ray crystallography experiments (see, for example, Kundu et al. 2002, Biophys J 83:723-732.), nuclear magnetic resonance experiments (see, for example, Freedberg et al., J Am Chem Soc 1998, 120(31):7916-7923) or by running molecular dynamics (MD) simulations. An MD simulation of a protein is done on a computer and allows one to determine the motion of all protein atoms over a period of time by calculating the physical interactions of the atoms with each other. The output of a MD simulation is the trajectory of the studied protein over the period of time of the simulation. The trajectory is an ensemble of protein conformations, also called snapshots, which are periodically sampled over the period of the simulation, e.g. every 1 picosecond (ps). It is by analyzing the ensemble of snapshots that one can quantify the flexibility of the protein amino acid residues. Thus, a flexible residue is one which adopts an ensemble of different conformations in the context of the polypeptide within which that residue resides. MD methods are known in the art, see, e.g., Brooks et al. "Proteins: A Theoretical Perspective of Dynamics, Structure and Thermodynamics" (Wiley, New York, 1988). Several software enable MD simulations, such as Amber (see Case et al. (2005) J Comp Chem 26:1668-1688), Charmm (sec Brooks et al. (1983) J Comp Chem 4:187-217; and MacKerell et al. (1998) in "The Encyclopedia of Computational Chemistry" vol. 1:271-177, Schleyer et al., eds. Chichester: John Wiley & Sons) or Impact (see Rizzo et al. J Am Chem Soc; 2000; 122(51):12898-12900.)

Most protein complexes share a relatively large and planar buried surface and it has been shown that flexibility of binding partners provides the origin for their plasticity, enabling them to conformationally adapt to each other (Structure (2000) 8, R137-R142). As such, examples of "induced fit" have been shown to play a dominant role in protein-protein interfaces. In addition, there is a steadily increasing body of data showing that proteins actually bind ligands of diverse shapes sizes and composition (Protein Science (2002) 11:184-187) and that the conformational diversity appears to be an essential component of the ability to recognize different partners (Science (2003) 299, 1362-1367). Flexible residues are involved in the binding of protein-protein partners (Structure (2006) 14, 683-693).

The flexible residues can adopt a variety of conformations that provide an ensemble of interaction areas that are likely to be recognized by memory B cells and to trigger an immunogenic response. Thus, antibody can be humanized by modifying a number of residues from the framework so that the ensemble of conformations and of recognition areas displayed by the modified antibody resemble as much as possible those adopted by a human antibody.

That can be achieved by modifying a limited number of residues by: (1) building a homology model of the parent mAb and running an MD simulation; (2) analyzing the flexible residues and identification of the most flexible residues of a non-human antibody molecule, as well as identifying residues or motifs likely to be a source of heterogeneity or of degradation reaction; (3) identifying a human antibody which displays the most similar ensemble of recognition areas as the parent antibody; (4) determining the flexible residues to be mutated, residues or motifs likely to be a source of heterogeneity and degradation are also mutated; and (5) checking for the presence of known T cell or B cell epitopes. The flexible residues can be found using an MD calculation as taught herein using an implicit solvent model, which accounts for the interaction of the water solvent with the protein atoms over the period of time of the simulation.

Once the set of flexible residues has been identified within the variable light and heavy chains, a set of human heavy and light chain variable region frameworks that closely resemble that of the antibody of interest are identified. That can be done, for example, using a blast search on the set of flexible residues against a database of antibody human germ line sequence. It can also be done by comparing the dynamics of the parent mAb with the dynamics of a library of germ line canonical structures. The CDR residues and neighboring residues are excluded from the search to ensure high affinity for the antigen is preserved.

Thus, a comparison the molecular dynamic trajectory of the antibody of interest with the trajectories of a library of germ line antibody structures was conducted. 16D7 was compared to a library of 49 germ line structures. The molecular dynamic trajectory retained of each antibody is an ensemble of molecular dynamic calculations during the molecular dynamics computer simulation where, for example, about 10 diverse conformations are used as diverse starting points, and for each starting point, about 10 molecular dynamic simulations are run. The 49 3D homology models of the human antibody germ lines were built by systematically combining the 7 most frequent human light chain (vκ1, vκ2, vκ3, vκ4, vλ1, v1λ2 and vλ3) and the 7 most frequent heavy chains (vh1a, vh1b, vh2, vh3, vh4, vh5 and vh6) (Nucleic Acids Research, 2005, Vol. 33, Database issue D593-D597). The flexible residues of 16D7 are then changed to the corresponding residues of the germ line structure with a trajectory closest to that of the antibody of interest.

Flexible residues then are replaced. When several human residues show similar homologies, the selection is driven also by the nature of the residues that are likely to affect the solution behavior of the humanized antibody. For instance, polar residues will be preferred in exposed flexible loops over hydrophobic residues. Residues which are a potential source of instability and heterogeneity are also mutated even if there are found in the CDRs. That will include exposed methionines as sulfoxide formation can result from oxygen radicals, proteolytic cleavage of acid labile bonds such as those of the Asp-Pro dipeptide (Drug Dev Res (2004) 61:137-154), deamidation sites found with an exposed asparagine residue followed by a small amino acid, such as Gly, Ser, Ala, His, Asn or Cys Chromatog (2006) 837:35-43) and N-glycosylation sites, such as the Asn-X-Ser/Thr site. Typically, exposed methionines will be substituted by a Leu, exposed asparagines will be replaced by a glutamine or by an aspartate, or the subsequent residue will be changed. For the glycosylation site (Asn-X-Ser/Thr), either the Asn or the Ser/Thr residue will be changed.

The resulting composite sequence is checked for the presence of known B cell or linear T-cell epitopes. A search is performed, for example, with the publicly available Immune Epitope Data Base (IEDB) (PLos Biol (2005) 3(3)e91). If a known epitope is found within the composite sequence, another set of human sequences is retrieved and substituted Unlike the resurfacing method of U.S. Pat. No. 5,639,641, both B-cell-mediated and T-cell-mediated immunogenic responses are addressed by the method. The method also avoids the issue of loss of activity that is sometimes observed with CDR grafting (U.S. Pat. No. 5,530,101). In addition, stability and solubility issues also are considered in the engineering and selection process, resulting in an antibody that is optimized for low immunogenicity, high antigen affinity and improved biophysical properties.

Strategies and methods for resurfacing antibodies, and other methods for reducing immunogenicity of antibodies within a different host, are disclosed, for example, in U.S. Pat. No. 5,639,641. Briefly, in a preferred method, (1) position alignments of a pool of antibody heavy and light chain variable regions are generated to yield heavy and light chain variable region framework surface exposed positions, wherein the alignment positions for all variable regions are at least about 98% identical; (2) a set of heavy and light chain variable region framework surface exposed amino acid residues is defined for a non-human, such as a rodent antibody (or fragment thereof); (3) a set of heavy and light chain variable region framework surface exposed amino acid residues that is most closely identical to the set of rodent surface exposed amino acid residues is identified; and (4) the set of heavy and light chain variable region framework surface exposed amino acid residues defined in step (2) is substituted with the set of heavy and light chain variable region framework surface exposed amino acid residues identified in step (3), except for those amino acid residues that are within 5 Å of any atom of any residue of a CDR of the rodent antibody, to yield a humanized, such as a rodent antibody retaining binding specificity.

Antibodies can be humanized by a variety of other techniques including CDR grafting (EPO 0 239 400; WO 91/09967; and U.S. Pat. Nos. 5,530,101 and 5,585,089), veneering or resurfacing (EPO 0 592 106; EPO 0 519 596; Padlan, 1991, Molec Imm 28(4/5):489-498; Studnicka et al., 1994, Prot Eng 7(6):805-814; and Roguska et al., 1994, PNAS 91:969-973) and chain shuffling (U.S. Pat. No. 5,565,332). Human antibodies can be made by a variety of methods known in the art including, but not limited to, phage display methods, see U.S. Pat. Nos. 4,444,887, 4,716,111, 5,545,806 and 5,814,318; and WO 98/46645, WO 98/50433, WO 98/24893, WO 98/16654, WO 96/34096, WO 96/33735 and WO 91/10741, using transgenic animals, such as rodents, using chimeric cells and so on.

"Antibody homolog" or "homolog" refers to any molecule which specifically binds CXCR5 as taught herein. Thus, an antibody homolog includes native or recombinant antibody, whether modified or not, portions of antibodies that retain the biological properties of interest, such as binding CXCR5, such as an $F_{ab}$ or $F_v$ molecule, a single chain antibody, a polypeptide carrying one or more CDR regions and so on. The amino acid sequence of the homolog need not be identical to that of the naturally occurring antibody but can be altered or modified to carry substitute amino acids, inserted amino acids, deleted amino acids, amino acids other than the twenty normally found in proteins and so on to obtain a polypeptide with enhanced or other beneficial properties.

Antibodies with homologous sequences are those antibodies with amino acid sequences that have sequence homology with the amino acid sequence of a CXCR5 antibody of the present invention. Preferably, homology is with the amino acid sequence of the variable regions of an antibody of the present invention. "Sequence homology" as applied to an amino acid sequence herein is defined as a sequence with at least about 90%, 91%, 92%, 93%, 94% or more sequence homology, and more preferably at least about 95%, 96%, 97%, 98% or 99% sequence homology to another amino acid sequence, as determined, for example, by the FASTA search method in accordance with Pearson & Lipman, Proc Natl Acad Sci USA 85, 2444-2448 (1988).

A chimeric antibody is one with different portions of an antibody derived from different sources, such as different antibodies, different classes of antibody, different animal species, for example, an antibody having a variable region derived from a murine monoclonal antibody paired with a human immunoglobulin constant region and so on. Thus, a humanized antibody is a species of chimeric antibody. Methods for producing chimeric antibodies are known in the art, see, e.g., Morrison, 1985, Science 229:1202; Oi et al., 1986, BioTechniques 4:214; Gillies et al., 1989, J Immunol Methods 125:191-202; and U.S. Pat. Nos. 5,807,715, 4,816,567, and 4,816,397.

Artificial antibodies include single chain antibodies, scFv fragments, chimeric antibodies, diabodies, triabodies, tetrabodies and mru (see reviews by Winter & Milstein, 1991, Nature 349:293-299; and Hudson, 1999, Curr Opin Imm 11:548-557), each with antigen-binding or epitope-binding ability. In the single chain $F_v$ fragment (scF$_v$), the $V_H$ and $V_L$ domains of an antibody are linked by a flexible peptide. Typically, the linker is a peptide of about 15 amino acids. If the linker is much smaller, for example, 5 amino acids, diabodies are formed, which are bivalent scFv dimers. If the linker is reduced to less than three amino acid residues, trimeric and tetrameric structures are formed that are called triabodies and tetrabodies, respectively. The smallest binding unit of an antibody can be a single CDR, typically the CDR2 or 3 of the heavy chain which has sufficient specific recognition and binding capacity, but can be any combination of CDR sequences as can be determined practicing the methods taught herein. Such a fragment is called a molecular recognition unit or mru. Several such mrus can be linked together with short linker peptides, therefore forming an artificial binding protein with higher avidity than a single mru.

Also included within the scope of the invention are functional equivalents of an antibody of interest. The term "functional equivalents" includes antibodies with homologous sequences, antibody homologs, chimeric antibodies, artificial antibodies and modified antibodies, for example, wherein each functional equivalent is defined by the ability to bind to CXCR5, inhibiting CXCR5 signaling ability or function, or inhibiting binding of CXCL13 and other ligands to CXCR5. The skilled artisan will understand that there is an overlap in the group of molecules termed "antibody fragments" and the group termed "functional equivalents." Methods of producing functional equivalents which retain CXCR5 binding ability are known to the person skilled in the art and are disclosed, for example, in WO 93/21319, EPO Ser. No. 239,400, WO 89/09622, EPO Ser. No. 338,745 and EPO Ser. No. 332,424.

The functional equivalents of the present application also include modified antibodies, e.g., antibodies modified by the covalent attachment of any type of molecule to the antibody. For example, modified antibodies include antibodies that have been modified, e.g., by glycosylation, acetylation, pegylation, deamidation, phosphorylation, amidation, derivatization by known protecting/blocking groups, proteolytic cleavage, linkage to a cellular ligand, linkage to a toxin or cytotoxic moiety or other protein etc. The covalent attachment need not yield an antibody that is immune from generating an anti-idiotypic response. The modifications may be achieved by known techniques, including, but not limited to, specific chemical cleavage, acetylation, formylation, metabolic synthesis etc. Additionally, the modified antibodies may contain one or more non-classical amino acids.

Many techniques are available to one of ordinary skill in the art which permit the optimization of binding affinity. Typically, the techniques involve substitution of various amino acid residues at the site of interest, followed by a screening analysis of binding affinity of the mutant polypeptide for the cognate antigen or epitope.

Once the antibody is identified and isolated, it is often useful to generate a variant antibody or mutant, or mutein, wherein one or more amino acid residues are altered, for example, in one or more of the hypervariable regions of the antibody. Alternatively, or in addition, one or more alterations (e.g., substitutions) of framework residues may be introduced in the antibody where these result in an improvement in the binding affinity of the antibody mutant for CXCR5. Examples of framework region residues that can be modified include those which non-covalently bind antigen directly (Amit et al., Science 233:747-753 (1986)); interact with/affect the conformation of a CDR (Chothia et al., J Mol Biol 196:901-917 (1987)); and/or participate in the $V_L$-$V_H$ interface (EP 239 400). In certain embodiments, modification of one or more of such framework region residues results in an enhancement of the binding affinity of the antibody for the cognate antigen. For example, from about one to about five framework residues may be altered in this embodiment of the invention. Sometimes, this may be sufficient to yield an antibody mutant suitable for use in preclinical trials, even where none of the hypervariable region residues have been altered. Normally, however, the antibody mutant can comprise one or more hypervariable region alteration(s). The constant regions also can be altered to obtain desirable or more desirable effector properties.

The hypervariable region residues which are altered may be changed randomly, especially where the starting binding affinity of the parent antibody is such that randomly-produced antibody mutants can be readily screened for altered binding in an assay as taught herein.

One procedure for obtaining antibody mutants, such as CDR mutants, is "alanine scanning mutagenesis" (Cunningham & Wells, Science 244:1081-1085 (1989); and Cunningham & Wells, Proc Nat Acad Sci USA 84:6434-6437 (1991)). One or more of the hypervariable region residue(s) are replaced by alanine or polyalanine residue(s). Those hypervariable region residue(s) demonstrating functional sensitivity to the substitutions then are refined by introducing further or other mutations at or for the sites of substitution. Thus, while the site for introducing an amino acid sequence variation is predetermined, the nature of the mutation per se need not be predetermined. Similar substitutions can be attempted with other amino acids, depending on the desired property of the scanned residues.

A more systematic method for identifying amino acid residues to modify comprises identifying hypervariable region residues involved in binding CXCR5 and those hypervariable region residues with little or no involvement with CXCR5 binding. An alanine scan of the non-binding hypervariable region residues is performed, with each ala mutant tested for enhancing binding to CXCR5. In another embodiment, those residue(s) significantly involved in binding CXCR5 are selected to be modified. Modification can involve deletion of a residue or insertion of one or more residues adjacent to a residue of interest. However, normally the modification involves substitution of the residue by another amino acid. A conservative substitution can be a first substitution. If such a substitution results in a change in biological activity (e.g., binding affinity), then another conservative substitution can be made to determine if more substantial changes are obtained.

Even more substantial modification in an antibody range and presentation of biological properties can be accomplished by selecting an amino acid that differs more substantially in properties from that normally resident at a site. Thus, such a substitution can be made while maintaining: (a) the structure of the polypeptide backbone in the area of the substitution, for example, as a sheet or helical conformation; (b) the charge or hydrophobicity of the molecule at the target site, or (c) the bulk of the side chain.

For example, the naturally occurring amino acids can be divided into groups based on common side chain properties:

(1) hydrophobic: methionine (M or met), alanine (A or ala), valine (V or val), leucine (L or leu) and isoleucine (I or ile);

(2) neutral, hydrophilic: cysteine (C or cys), serine (S or ser), threonine (T or thr), asparagine (N or asn) and glutamine (Q or gln);

(3) acidic: aspartic acid (D or asp) and glutamic acid (E or glu);

(4) basic: histidine (H or his), lysine (K or lys) and arginine (R or arg);

(5) residues that influence chain orientation: glycine (G or gly) and proline (P or pro), and (6) aromatic: tryptophan (W or trp), tyrosine (Y or tyr) and phenylalanine (F or phe).

Non-conservative substitutions can entail exchanging an amino acid with an amino acid from an other group. Conservative substitutions can entail exchange of one amino acid for another within a group.

Preferred amino acid substitutions include those which: (1) reduce susceptibility to proteolysis, (2) reduce susceptibility to oxidation, (3) alter binding affinity and (4) confer or modify other physico-chemical or functional properties of such analogs. Analogs can include various muteins of a sequence other than the naturally occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence) unless of a change in the bulk or conformation of the R group or side chain, Proteins, Structures and Molecular Principles (Creighton, ed., W.H. Freeman and Company, New York (1984)); Introduction to Protein Structure (Branden & Tooze, eds., Garland Publishing, New York, N.Y. (1991)); and Thornton et al. Nature 354:105 (1991).

Ordinarily, the antibody mutant with improved biological properties will have an amino acid sequence having at least 75% amino acid sequence identity or similarity with the amino acid sequence of either the heavy or light chain variable domain of the parent anti-human CXCR5 antibody, at least 80%, at least 85%, at least 90% and often at least 95% identity. Identity or similarity with respect to parent antibody sequence is defined herein as the percentage of amino acid residues in the candidate sequence that are identical (i.e., same residue) or similar (i.e., amino acid residue from the same group based on common side-chain properties, supra) with the parent antibody residues, after aligning the sequences and introducing gaps, if necessary, to achieve the maximum percent sequence identity.

Alternatively, antibody mutants can be generated by systematic mutation of the FR and CDR regions of the heavy and light chains, or the $F_c$ region of the anti-CXCR5 antibody. Another procedure for generating antibody mutants involves the use of affinity maturation using phage display (Hawkins et al., J Mol Biol 254:889-896 (1992) and Lowman et al., Biochemistry 30(45):10832-10838 (1991)). Bacteriophage coat-protein fusions (Smith, Science 228:1315 (1985); Scott & Smith, Science 249:386 (1990); Cwirla et al. Proc Natl Acad Sci USA 8:309 (1990); Devlin et al. Science 249:404 (1990); Wells & Lowman, Curr Opin Struct Biol 2:597 (1992); and U.S. Pat. No. 5,223,409) are known to be useful for linking the phenotype of displayed proteins or peptides to the genotype of bacteriophage particles which encode them. The $F_{ab}$ domains of antibodies have also been displayed on phage (McCafferty et al., Nature 348: 552 (1990); Barbas et al. Proc Natl Acad Sci USA 88:7978 (1991); and Garrard et al. Biotechnol 9:1373 (1991)).

Monovalent phage display consists of displaying a set of protein variants as fusions of a bacteriophage coat protein on phage particles (Bass et al., Proteins 8:309 (1990). Affinity maturation, or improvement of equilibrium binding affinities of various proteins, has previously been achieved through successive application of mutagenesis, monovalent phage display and functional analysis (Lowman & Wells, J Mol Biol 234:564 578 (1993); and U.S. Pat. No. 5,534,617), for example, by focusing on the CDR regions of antibodies (Barbas et al., Proc Natl Acad Sci USA 91:3809 (1994); and Yang et al., J Mol Biol 254:392 (1995)).

Libraries of many (for example, $10^6$ or more) protein variants, differing at defined positions in the sequence, can be constructed on bacteriophage particles, each of which contains DNA encoding the particular protein variant. After cycles of affinity purification, using an immobilized antigen, individual bacteriophage clones are isolated, and the amino acid sequence of the displayed protein is deduced from the DNA.

Following production of the antibody mutant, the biological activity of that molecule relative to the parent antibody can be determined as taught herein. As noted above, that may involve determining the binding affinity and/or other biological activities or physical properties of the antibody. In a preferred embodiment of the invention, a panel of antibody mutants are prepared and are screened for binding affinity for the antigen. One or more of the antibody mutants selected from the screen are optionally subjected to one or more further biological activity assays to confirm that the antibody mutant(s) have new or improved properties. In preferred embodiments, the antibody mutant retains the ability to bind CXCR5 with a binding affinity similar to or better/higher than that of the parent antibody.

The antibody mutant(s) so selected may be subjected to further modifications, often depending on the intended use of the antibody. Such modifications may involve further alteration of the amino acid sequence, fusion to heterologous polypeptide(s) and/or covalent modifications. For example, a cysteine residue not involved in maintaining the proper conformation of the antibody mutant may be substituted, generally with serine, to improve the oxidative stability of the molecule and to prevent aberrant cross-linking. Conversely, a cysteine may be added to the antibody to improve stability (particularly where the antibody is an antibody fragment such as an $F_v$ fragment).

Another type of antibody mutant has an altered glycosylation pattern. That may be achieved by deleting one or more carbohydrate moieties found in the antibody and/or by adding one or more glycosylation sites that are not present in the antibody. Glycosylation of antibodies is typically either N-linked to Asn or O-linked to Ser or Thr. The tripeptide sequences, asparagine-X-serine and asparagine-X-threonine, where X is any amino acid except proline, are common recognition sequences for enzymatic attachment of a carbohydrate moiety to the asparagine side chain. N-acetylgalactosamine, galactose, fucose or xylose, for example, are bonded to a hydroxyamino acid, most commonly serine or threonine, although 5-hydroxyproline or 5-hydroxylysine also may be used. Addition or substitution of one or more serine or threonine residues to the sequence of the original antibody can enhance the likelihood of O-linked glycosylation.

It may be desirable to modify the antibody of the invention with respect to effector function, so as to enhance the effectiveness of the antibody. For example, cysteine residue(s) may be introduced in the $F_c$ region, thereby allowing interchain disulfide bond formation in that region. The homodimeric antibody thus generated may have improved internalization capability and/or increased complement-mediated cell killing and antibody-dependent cellular cytotoxicity (ADCC), see Caron et al., J Exp Med 176:1191-1195 (1992) and Shopes, Immunol 148:2918-2922 (1993). Alternatively, an antibody can be engineered which has dual $F_c$ regions and may thereby have enhanced complement lysis and ADCC capabilities, see Stevenson et al., Anti-Cancer Drug Design 3: 219 230 (1989).

Covalent modifications of the antibody are included within the scope of the invention. Such may be made by chemical synthesis or by enzymatic or chemical cleavage of the antibody, if applicable. Other types of covalent modifications of the antibody are introduced into the molecule by reacting targeted amino acid residues of the antibody with an organic derivatizing agent that is capable of reacting with selected side chains or with the N-terminal or C-terminal residue.

Cysteinyl residues can be reacted with α-haloacetates (and corresponding amines), such as chloroacetic acid or chloroacetamide, to yield carboxylmethyl or carboxyamidomethyl derivatives. Cysteinyl residues also can be derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercura-4-nitrophenol or chloro-7-nitrobenzo-2-oxa-1,3-diazole, for example.

Histidyl residues can be derivatized by reaction with diethylpyrocarbonate at pH 5.5-7.0. p-bromophenacyl bromide also can be used, the reaction is preferably performed in 0.1 M sodium cacodylate at pH 6.0.

Lysinyl and α terminal residues can be reacted with succinic or other carboxylic acid anhydrides to reverse the charge of the residues. Other suitable reagents for derivatizing α-amino-containing residues include imidoesters, such as methyl picolinimidate, pyridoxal phosphate, pyridoxal, chloroborohydride, trinitrobenzenesulfonic acid, O-methylisourea and 2,4-pentanedione, and the amino acid can be transaminase-catalyzed with glyoxylate.

Arginyl residues can be modified by reaction with one or several conventional reagents, such as phenylglyoxal, 2,3-butanedione, 1,2-cyclohexanedione and ninhydrin. Derivatization of arginine residues often requires alkaline reaction conditions. Furthermore, the reagents may react with lysine as well as the arginine ε-amino group.

The specific modification of tyrosyl residues can be made with aromatic diazonium compounds or tetranitromethane. For example, N-acetylimidizole and tetranitromethane are used to form O-acetyl tyrosyl species and 3-nitro derivatives, respectively. Tyrosyl residues can be iodinated using $^{125}$I or $^{131}$I to prepare labeled proteins for use in a radioimmunoassay.

Carboxyl side groups (aspartyl or glutamyl) can be modified by reaction with carbodiimides (R—N=C=C—R'), where R and R' can be different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues can be converted to asparaginyl and glutaminyl residues by reaction with ammonium ions.

Glutaminyl and asparaginyl residues are frequently deamidated to the corresponding glutamyl and aspartyl residues, respectively, under neutral or basic conditions. The deamidated form of those residues falls within the scope of this invention.

Other modifications include hydroxylation of proline and lysine, phosphorylation of hydroxyl groups of serinyl or threonyl residues, methylation of the α-amino groups of lysine, arginine, and histidine side chains (Creighton, Proteins: Structure and Molecular Properties, W.H. Freeman & Co., San Francisco, pp. 79-86 (1983)), acetylation of the N-terminal amine and amidation of any C-terminal carboxyl group.

Another type of covalent modification involves chemically or enzymatically coupling glycosides to the antibody. Those procedures do not require production of the antibody in a host cell that has glycosylation capabilities for N-linked or O-linked glycosylation. Depending on the coupling mode used, the sugar(s) may be attached to: (a) arginine and histidine; (b) free carboxyl groups; (c) free sulfhydryl groups, such as those of cysteine; (d) free hydroxyl groups, such as those of serine, threonine or hydroxyproline; (e) aromatic residues such as those of phenylalanine, tyrosine or tryptophan; or (f) the amide group of glutamine. Such methods are described in WO 87/05330 and in Aplin & Wriston, CRC Crit. Rev Biochem, pp. 259-306 (1981).

Removal of any carbohydrate moieties present on the antibody may be accomplished chemically or enzymatically. Chemical deglycosylation, for example, can require exposure of the antibody to the compound, trifluoromethanesulfonic acid, or an equivalent compound, resulting in cleavage of most or all sugars except the linking sugar (N-acetylglucosamine or N-acetylgalactosamine), while leaving the antibody intact. Chemical deglycosylation is described, for example, in Hakimuddin et al. Arch Biochem Biophys 259:52 (1987) and in Edge et al., Anal Biochem 118:131 (1981). Enzymatic cleavage of carbohydrate moieties on antibodies can be achieved by any of a variety of endoglycosidases and exoglycosidases as described, for example, in Thotakura et al., Meth Enzymol 138:350 (1987).

Another type of covalent modification of the antibody comprises linking the antibody to one of a variety of nonproteinaceous polymers, e.g., polyethylene glycol, polypropylene glycol or polyoxylalkylenes, in the manner set forth in U.S. Pat. No. 4,640,835; 4,496,689; 4,301,144; 4,670,417; 4,791,192 or 4,179,337.

Another technique preferred for obtaining mutants or muteins is affinity maturation by phage display (Hawkins et al., J Mol Biol 254:889-896 (1992); and Lowman et al., Biochemistry 30(45):10832-10838 (1991)). Briefly, several hypervariable region sites (e.g., 6-7 sites) are mutated to generate all possible amino acid substitutions at each site. The antibody mutants thus generated are displayed in monovalent fashion on phage particles as fusions to a protein found on the particles. The phage expressing the various mutants can be cycled through rounds of binding selection, followed by isolation and sequencing of those mutants which display high affinity.

The method of selecting novel binding polypeptides can utilize a library of structurally related polypeptides. The library of structurally related polypeptides, for example, fused to a phage coat protein, is produced by mutagenesis, and is displayed on the surface of the particle. The particles then are contacted with a target molecule and those particles having the highest affinity for the target are separated from those of lower affinity. The high affinity binders then are amplified by infection of a suitable bacterial host and the competitive binding step is repeated. The process is repeated until polypeptides of the desired affinity are obtained.

Alternatively, multivalent phage (McCafferty et al. (1990) Nature 348:552-554; and Clackson et al. (1991) Nature 352:624-628) also can be used to express random point mutations (for example, generated by use of an error-prone DNA polymerase) to generate a library of phage antibody fragments which then could be screened for affinity to CXCR5, Hawkins et al., (1992) J Mol Biol 254:889-896.

Preferably, during the affinity maturation process, the replicable expression vector is under tight control of a transcription regulatory element, and the culturing conditions are adjusted so the amount or number of particles displaying more than one copy of the fusion protein is less than about 1%. Also preferably, the amount of particles displaying more than one copy of the fusion protein is less than 10% of the amount of particles displaying a single copy of the fusion protein. Preferably the amount is less than 20%.

Functional equivalents may be produced by interchanging different CDRs of different antibody chains within a framework or a composite FR derived from plural antibodies. Thus, for example, different classes of antibody are possible for a given set of CDRs by substitution of different heavy chains, for example, $IgG_{1-4}$, IgM, $IgA_{1-2}$ or IgD, to yield differing CXCR5 antibody types and isotypes. Similarly, artificial antibodies within the scope of the invention may be produced by embedding a given set of CDRs within an entirely synthetic framework.

For example, a suitable framework and $F_c$ portion to carry the variable region or one or more CDR's of interest is obtained from an IgG4 molecule, which has reduced effector function.

In other embodiments, to enhance the properties of a CXCR5-binding molecule of interest, certain modifications can be made to the framework portion and/or $F_c$ portion of the molecule carrying the antigen-binding portion of a molecule of interest. For example, amino acid substitutions can be made to enhance or to reduce properties of interest. Thus, in an IgG4 molecule, substitutions at sites known to impact function, for example, in the hinge region, in a region that impacts an effector function or that impacts $F_c$ binding, for example, are suitable for modification. In an IgG4 molecule, substitutions, using Kabat numbering, at amino acid 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255 and so on, or combinations thereof, can be made to obtain desired properties. For example, substituting a proline for serine 241 can stabilize the tertiary and quaternary structures of the molecule (Mol Imm 30(1)105-108, 1993), and substituting glutamic acid for leucine 248 can dampen effector function(s) (J Imm 164(4)1925-1033, 2000; and Clin Imm 98(2)164-174, 2001).

Another beneficial property is obtaining an antibody derivative which binds CXCR5 but, for example, does not deplete B cells. That can be advantageous as antibody production in a patient is not compromised. Treatment with such a reagent also facilitates a combination regimen with a second drug for a particular indication that acts at a level other than at the B cell. That may be at the level of the T cell, for example.

Hence, for example, 16D7-HC1-LC3 was treated to contain two substitutions, S241P and L248E. The proline and glutamic acid residues confer desired properties on a CXCR5-binding molecule of interest carrying an IgG4 framework, such as, stability and reduced effector function.

The antibody fragments and functional equivalents of the present invention encompass those molecules with a detectable degree of specific binding to CXCR5. A detectable degree of binding includes all values in the range of at least 10-100%, preferably at least 50%, 60% or 70%, more preferably at least 75%, 80%, 85%, 90%, 95% or 99% of the binding ability of an antibody of interest. Also included are equivalents with an affinity greater than 100% that of an antibody of interest.

The CDRs generally are of importance for epitope recognition and antibody binding. However, changes may be made to residues that comprise the CDRs without interfering with the ability of the antibody to recognize and to bind the cognate epitope. For example, changes that do not impact epitope recognition, yet increase the binding affinity of the antibody for the epitope, may be made. Several studies have surveyed the effects of introducing one or more amino acid changes at various positions in the sequence of an antibody, based on the knowledge of the primary antibody sequence, on the properties thereof, such as binding and level of expression (Yang et al., 1995, J Mol Biol 254:392-403; Rader et al., 1998, Proc Natl Acad Sci USA 95:8910-8915; and Vaughan et al., 1998, Nature Biotechnology 16, 535-539).

Thus, equivalents of an antibody of interest can be generated by changing the sequences of the heavy and light chain genes in the CDR1, CDR2 or CDR3, or framework regions, using methods such as oligonucleotide-mediated site-directed mutagenesis, cassette mutagenesis, error-prone PCR, DNA shuffling or mutator-strains of *E. coli* (Vaughan et al., 1998, Nat Biotech 16:535-539; and Adey et al., 1996, Chap. 16, pp. 277-291, in Phage Display of Peptides and Proteins, eds. Kay et al., Academic Press). The methods of changing the nucleic acid sequence of the primary antibody can result in antibodies with improved affinity (Gram et al., 1992, Proc Natl Acad Sci USA 89:3576-3580; Boder et al., 2000, Proc Natl Acad Sci USA 97:10701-10705; Davies & Riechmann, 1996, Immunotech 2:169-179; Thompson et al., 1996, J Mol Biol 256:77-88; Short et al., 2002, J Biol Chem 277:16365-16370; and Furukawa et al., 2001, J Biol Chem 276:27622-27628).

Repeated cycles of "polypeptide selection" can be used to select for higher and higher affinity binding by, for example, the selection of multiple amino acid changes which are selected by multiple selection of cycles. Following a first round of selection, involving a first region of selection of amino acids in the ligand or antibody polypeptide, additional rounds of selection in other regions or amino acids of the ligand are conducted. The cycles of selection are repeated until the desired affinity properties are achieved.

Improved antibodies also include those antibodies having improved characteristics that are prepared by the standard techniques of animal immunization, hybridoma formation and selection for antibodies with specific characteristics.

"Antagonist" refers to a molecule capable of inhibiting one or more biological activities of a target molecule, such as signaling by CXCR5. Antagonists may interfere with the binding of a receptor to a ligand and vice versa, by incapacitating or killing cells activated by a ligand, and/or by interfering with receptor or ligand activation (e.g., tyrosine kinase activation) or signal transduction after ligand binding to a receptor. The antagonist may completely block receptor-ligand interactions or may substantially reduce such interactions. All such points of intervention by an antagonist shall be considered equivalent for purposes of the instant invention. Thus, included within the scope of the invention are antagonists (e.g., neutralizing antibodies) that bind to CXCR5, CXCL13 or other ligands of CXCR5, or a complex of CXCR5 and a ligand thereof, such as CXCL13; amino acid sequence variants or derivatives of CXCR5 or CXCL13 which antagonize the interaction between CXCR5 and a ligand, such as CXCL13; soluble CXCR5, optionally fused to a heterologous molecule such as an immunoglobulin region (e.g., an immunoadhesin); a complex comprising CXCR5 in association with another receptor or biological molecule; synthetic or native sequence peptides which bind to CXCR5; and so on.

"Agonist" refers to a compound, including a protein, a polypeptide, a peptide, an antibody, an antibody fragment, a conjugate, a large molecule, a small molecule, which activates one or more biological activities of CXCR5. Agonists may interact with the binding of a receptor to a ligand and vice versa, by acting as a mitogen of cells activated by a ligand, and/or by interfering with cell inactivation or signal transduction inhibition after ligand binding to a receptor. All such points of intervention by an agonist shall be considered equivalent for purposes of the instant invention. Thus, included within the scope of the invention are agonists that bind to CXCR5, CXCL13 or other ligand of CXCR5, or a complex of CXCR5 and a ligand thereof, such as CXCL13; amino acid sequence variants or derivatives of CXCR5 or CXCL13 which facilitate the interaction between CXCR5 and a ligand, such as CXCL13; soluble CXCR5, optionally fused to a heterologous molecule such as an immunoglobulin region (e.g., an immunoadhesin); a complex comprising CXCR5 in association with another receptor or biological molecule; synthetic or native sequence peptides which bind to CXCR5; and so on. The agonist generally is an entity which directly activates CXCR5, for example, to signal.

The terms "cell," "cell line," and "cell culture" include progeny thereof. It is also understood that all progeny may not be precisely identical, such as in DNA content, due to deliberate or inadvertent mutation. Variant progeny that have the same function or biological property of interest, as screened for in the original cell, are included. The "host cells" used in the present invention generally are prokaryotic or eukaryotic hosts, selected as a design choice.

"Transformation" of a cellular organism, cell or cell line with a nucleic acid means introducing a nucleic acid into the target cell so that the nucleic acid is replicable, either as an extrachromosomal element or by chromosomal integration, and, optionally, expressed. "Transfection" of a cell or organism with a nucleic acid refers to the taking up of the nucleic acid, e.g., an expression vector, by the cell or organism whether or not any coding sequences are in fact expressed. The terms "transfected host cell" and "transformed" refer to a cell in which a nucleic acid was introduced. Typical prokaryotic host cells include various strains of *E. coli*. Typical eukaryotic host cells are mammal cells, such as Chinese hamster ovary, or cells of human origin. The introduced nucleic acid sequence may be from the same species as the host cell or of a different species from the host cell, or may be a hybrid nucleic acid sequence, containing some foreign and some homologous nucleic acids. Transformation can also occur by transduction or infection with virus-derived elements.

The term "vector" means a nucleic acid construct, a carrier, containing a nucleic acid, the transgene, the foreign gene or the gene of interest, which can be operably linked to suitable control sequences for expression of the transgene in a suitable host. Such control sequences include, for example, a promoter to effect transcription, an optional operator sequence to control such transcription, a sequence encoding suitable mRNA ribosome binding sites and sequences which control the termination of transcription and translation. The vector may be a plasmid, a phage particle or just a potential genomic insert. Once transformed into a suitable host, the vector may replicate and function independently of the host genome, or may in some instances, integrate into the host cell genome. In the present specification, "plasmid" and "vector" are used interchangeably, as the plasmid is a commonly used form of vector. However, the invention is intended to include such other forms of vectors which serve equivalent carrier function as and which are, or become, known in the art, such as viruses, synthetics molecules that carry nucleic acids, liposomes and the like.

"Mammal" for purposes of treatment refers to any animal classified as a mammal, including human, domestic and farm animals, nonhuman primates, and zoo, sports or pet animals, such as dogs, horses, cats, cows etc.

The antibodies of interest can be screened or can be used in an assay as described herein or as known in the art. Often, such assays require a reagent to be detectable, that is, for example, labeled. The word "label" when used herein refers to a detectable compound or composition which can be conjugated directly or indirectly to a molecule or protein, e.g., an antibody. The label may itself be detectable (e.g., radioisotope labels, particles or fluorescent labels) or, in the case of an enzymatic label, may catalyze chemical alteration of a substrate compound or composition which is detectable.

As used herein, "solid phase" means a non-aqueous matrix to which an entity or molecule, such as the antibody of the instant invention, can adhere. Example of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others can be used in a purification column (e.g., an affinity chromatography column). Thus, the solid phase can be a paper, a bead, a plastic, a chip and so on, can be made from a variety of materials, such as nitrocellulose, agarose, polystyrene, polypropylene, silicon and so on, and can be in a variety of configurations.

Soluble CXCR5 or fragments thereof, such as the extracellular domain (EC) domain, can be used as immunogens for generating antibodies of interest. The immunogen can be obtained or isolated from natural sources or can be made recombinantly. Whole cells, such as $CXCR5^+$ cells, cells derived from a natural source (e.g., B cell, B cell lines or cancer cell lines) or cells transformed (or transfected) by recombinant techniques to express, and perhaps to overexpress CXCR5, may be used as the immunogen for making the antibodies of interest. Also, membrane preparations carrying CXCR5 or synthetic peptides or truncated polypeptides corresponding to the EC regions of CXCR5 can be used, as known in the art.

The EC, which is about 60 amino acids in length, or portions thereof, of CXCR5 can be used as the immunogen. Other forms of the immunogen useful for preparing antibodies, such as a conjugate, will be apparent to those in the art. Thus, CXCR5, or portions thereof, can be attached to a carrier molecule, such as albumin or KLH, to be used as an immunogen. Of course, with cells expressing CXCR5, it is the EC domain which is the preferred immunogen or portion of the immunogen.

The gene or a cDNA encoding CXCR5, as known in the art, may be cloned in a plasmid or other expression vector and expressed in any of a number of expression systems according to methods well known to those of skill in the art, and see below, for example. Because of the degeneracy of the genetic code, a multitude of nucleotide sequences encoding CXCR5 protein or polypeptides may be used in the practice of expressing recombinant CXCR5 or functional products thereof. The nucleotide sequence may vary by selecting combinations based on possible codon choices, such as those preferred by the host cell. The combinations are made in accordance with the standard triplet genetic code as applied to the nucleotide sequence that codes for naturally occurring CXCR5 and all such variations may be considered. Thus, the CXCR5-encoding sequence can be recoded to contain codons expressing the amino acid of interest, however, the triplet codon is one favored by the gene expression machinery of the host cell, such as a human cell. Any one of those polypeptides may be used in the immunization of an animal, such as a camelid, or other system to generate antibodies that bind to CXCR5.

As mentioned above, the CXCR5 immunogen may, when beneficial, be expressed as a fusion protein that has CXCR5 attached to a fusion segment, which generally is a polypeptide with one or more beneficial functions. The fusion segment often aids in protein purification, e.g., by permitting the fusion protein to be isolated and purified by affinity chromatography, but can also be used to increase immunogenicity. Fusion proteins can be produced by culturing a recombinant cell transformed with a fusion nucleic acid sequence that encodes a protein attached to either the carboxyl and/or amino terminal end of the CXCR5 polypeptide. Fusion segments may include, but are not limited to, immunoglobulin $F_c$ regions, glutathione-S-transferase, β-galactosidase, a polyhistidine segment capable of binding to a divalent metal ion and maltose binding protein.

Nucleic acid molecules encoding amino acid sequence mutants can be prepared by a variety of methods known in the art. The methods include, but are not limited to, oligonucleotide-mediated (or site-directed) mutagenesis, PCR mutagenesis and cassette mutagenesis of an earlier prepared mutant or a non-mutant version of the molecule of interest, (see, for example, Kunkel, Proc Natl Acad Sci USA 82:488 (1985)).

Recombinant expression of an antibody of the invention, or fragment, derivative or analog thereof, (e.g., a heavy or light chain of an antibody of the invention, a single chain antibody of the invention or an antibody mutein of the invention) includes construction of an expression vector containing a polynucleotide that encodes the antibody or a fragment of the antibody as described herein. Once a polynucleotide encoding an antibody molecule has been obtained, the vector for the production of the antibody may be produced by recombinant DNA technology as known in the art. An expression vector is constructed containing antibody coding sequences and appropriate transcriptional and translational control signals. The methods include, for example, in vitro recombinant DNA techniques, synthetic techniques and in vivo genetic recombination.

The expression vector is transferred to a host cell by conventional techniques and the transfected cells then are cultured by conventional techniques to produce an antibody or fragment of the invention. In one aspect of the invention, vectors encoding both the heavy and light chains may be co-expressed in the host cell for expression of the entire immunoglobulin molecule, as detailed herein.

A variety of host/expression vector systems may be utilized to express the antibody molecules of the invention. Such expression systems represent vehicles by which the coding sequences of interest may be produced and subsequently purified, but also represent cells which may, when transformed or transfected with the appropriate nucleotide coding sequences, express an antibody molecule of the invention in situ. Bacterial cells, such as *E. coli*, and eukaryotic cells are commonly used for the expression of a recombinant antibody molecule, especially for the expression of whole recombinant antibody molecule. For example, mammal cells such as CHO cells, in conjunction with a vector, such as one carrying the major intermediate early gene promoter element from human cytomegalovirus, are an effective expression system for antibodies (Foecking et al., Gene 45:101 (1986); and Cockett et al., Bio/Technology 8:2 (1990)). Plants and plant cell culture, insect cells and so on also can be used to make the proteins of interest, as known in the art.

In addition, a host cell is chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the expressed antibody of interest. Hence, eukaryotic host cells which possess the cellular machinery for proper processing of the primary transcript, glycosylation and phosphorylation of the gene product may be used. Such mammalian host cells include, but are not limited to, CHO, COS, 293, 3T3 or myeloma cells.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites etc.) and a selectable marker. Following the introduction of the foreign DNA, engineered cells may be allowed to grow for one to two days in an enriched media, and then are moved to a selective media. The selectable marker in the recombinant plasmid confers resistance to the selection and allows cells to stably integrate the plasmid into a chromosome and be expanded into a cell line. Such engineered cell lines not only are useful for antibody production but are useful in screening and evaluation of compounds that interact directly or indirectly with the antibody molecule.

A number of selection systems may be used, including but not limited to the Herpes simplex virus thymidine kinase (Wigler et al., Cell 11:223 (1977)), hypoxanthine-guanine phosphoribosyltransferase (Szybalska et al., Proc Natl Acad Sci USA 48:202 (1992)), glutamate synthase selection in the presence of methionine sulfoximide (Adv Drug Del Rev 58, 671, 2006 and see the website or literature of Lonza Group Ltd.) and adenine phosphoribosyltransferase (Lowy et al., Cell 22:817 (1980)) genes in tk, hgprt or aprt cells, respectively. Also, antimetabolite resistance can be used as the basis of selection for the following genes: dhfr, which confers resistance to methotrexate (Wigler et al., Proc Natl Acad Sci USA 77:357 (1980); O'Hare et al., Proc Natl Acad Sci USA 78:1527 (1981)); gpt, which confers resistance to mycophenolic acid (Mulligan et al., Proc Natl Acad Sci USA 78:2072 (1981)); neo, which confers resistance to the aminoglycoside, G-418 (Wu et al., Biotherapy 3:87 (1991)); and hygro, which confers resistance to hygromycin (Santerre et al., Gene 30:147 (1984)). Methods known in the art of recombinant DNA technology may be routinely applied to select the desired recombinant clone, and such methods are described, for example, in Ausubel et al., eds., Current Protocols in Molecular Biology, John Wiley & Sons (1993); Kriegler, Gene Transfer and Expression, A Laboratory Manual, Stockton Press (1990); Dracopoli et al., eds., Current Protocols in Human Genetics, John Wiley & Sons (1994); and Colberre-Garapin et al., J Mol Biol 150:1 (1981).

The expression levels of an antibody molecule can be increased by vector amplification (for example, see Bebbington et al., in DNA Cloning, Vol. 3. Academic Press (1987)). When a marker in the vector system expressing antibody is amplifiable, an increase in the level of inhibitor present in the culture will increase the number of copies of the marker gene. Since the amplified region is associated with the antibody gene, production of the antibody will also increase (Crouse et al., Mol Cell Biol 3:257 (1983)).

The host cell may be co-transfected with two or more expression vectors of the invention, for example, the first vector encoding a heavy chain-derived polypeptide and the second vector encoding a light chain-derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); and Kohler, Proc Natl Acad Sci USA 77:2197 (1980)). The coding sequences for the heavy and light chains may comprise cDNA or genomic DNA.

Once an antibody molecule of the invention has been produced by an animal, chemically synthesized or recombinantly expressed, it may be purified by any method known in the art for purification of an immunoglobulin molecule, for example, by chromatography (e.g., ion exchange, affinity, particularly by affinity for CXCR5 after Protein A and size-exclusion chromatography and so on), centrifugation, differential solubility or by any other standard technique for the purification of proteins. In addition, the antibodies of the instant invention or fragments thereof can be fused to heterologous polypeptide sequences described herein or otherwise known in the art, to facilitate purification.

Recombinant CXCR5 protein, as exemplified in the examples below, was used to immunize mice to generate the hybridomas that produce monoclonal antibodies of the present invention. The monoclonals obtained were selected for those with beneficial therapeutic potential, for example, preventing binding of CXCR5 ligand thereto. The selected antibodies then were modified to obtain beneficial properties, such as having enhanced stability in vivo.

The antibodies of the present invention may be generated by any suitable method known in the art. The antibodies of the present invention may comprise polyclonal antibodies, although because of the modification of antibodies to optimize use in human, as well as to optimize the use of the antibody per se, monoclonal antibodies are preferred because of ease of production and manipulation of particular proteins. Methods of preparing polyclonal antibodies are known to the skilled artisan (Harlow et al., Antibodies: a Laboratory Manual, Cold Spring Harbor Laboratory Press, 2nd ed. (1988)).

For example, an immunogen, as exemplified herein, may be administered to various host animals including, but not limited to, rabbits, mice, camelids, rats etc., to induce the production of serum containing polyclonal antibodies specific for CXCR5. The administration of the immunogen may entail one or more injections of an immunizing agent and, if desired, an adjuvant. Various adjuvants may be used to increase the immunological response, depending on the host species, and include but are not limited to, Freund's (complete and incomplete), mineral oil, gels, alum (aluminum hydroxide), surface active substances, such as lysolecithin, pluronic polyols, polyanions, peptides, oil emulsions, keyhole limpet hemocyanins (KLH), dinitrophenol and potentially useful human adjuvants, such as BCG (Bacille Calmette-Guerin) and *Corynebacterium parvum*. Additional examples of adjuvants which may be employed include the MPL-TDM adjuvant (monophosphoryl lipid A, synthetic trehalose dicorynomycolate). Immunization protocols are well known in the art and may be performed by any method that elicit an immune response in the animal host chosen. Thus, various administration routes can be used over various time periods as a design choice.

Typically, the immunogen (with or without adjuvant) is injected into the mammal by multiple subcutaneous or intraperitoneal injections, or intramuscularly or intravenously. The immunogen may include a CXCR5 polypeptide, a fusion protein, or variants thereof, which may be produced by a cell that produces or overproduces CXCR5, which may be a naturally occurring cell, a naturally occurring mutant cell or a genetically engineered cell. In certain circumstances, whole cells expressing CXCR5 can be used. Depending on the nature of the polypeptides (i.e., percent hydrophobicity, percent hydrophilicity, stability, net charge, isoelectric point etc.), the CXCR5 or portion thereof may be modified or conjugated to be immunogenic or more immunogenic in the animal, such as a mammal, being immunized. For example, CXCR5 or a portion thereof can be conjugated to a carrier. The conjugation includes either chemical conjugation by derivatizing active chemical functional groups to both the immunogen and the immunogenic protein to be conjugated such that a covalent bond is formed, or through fusion-protein based methodology, or other methods known to the skilled artisan. Examples of such carriers or immunogenic proteins include, but are not limited to, KLH, ovalbumin, serum albumin, bovine thyroglobulin, soybean trypsin inhibitor, and promiscuous T helper peptides. Various adjuvants may be used to increase the immunological response as described above.

Once a suitable preparation is obtained, it is possible to isolate particular antibodies from the plural antibodies by known separation techniques, such as affinity chromatography, panning, absorption and so on. In that way, an individual antibody species can be obtained for further study, for example, sequencing to obtain the amino acid sequences of one or more CDRs.

The antibodies of the present invention preferably comprise monoclonal antibodies. Monoclonal antibodies may be prepared using hybridoma technology, such as described by Kohler et al., Nature 256:495 (1975); U.S. Pat. No. 4,376,110; Harlow et al., Antibodies: A Laboratory Manual, Cold Spring Harbor Laboratory Press, 2nd ed. (1988) and Hammerling et al., Monoclonal Antibodies and T-Cell Hybridomas, Elsevier (1981), recombinant DNA methods, for example, making and using transfectomas, or other methods known to the artisan. Other examples of methods which may be employed for producing monoclonal antibodies include, but are not limited to, the human B-cell hybridoma technique (Kosbor et al., Immunology Today 4:72 (1983); and Cole et al., Proc Natl Acad Sci USA 80:2026 (1983)), and the EBV-hybridoma technique (Cole et al., Monoclonal Antibodies and Cancer Therapy, pp. 77-96, Alan R. Liss (1985)). Such antibodies may be of any immunoglobulin class including IgG, IgM, IgE, IgA and IgD, and any subclass thereof. The hybridoma producing the mAb of the invention may be cultivated in vitro or in vivo.

In the hybridoma model, a host such as a mouse, a humanized mouse, a transgenic mouse with human immune system genes, hamster, rabbit, rat, camel or any other appropriate host animal, is immunized to elicit lymphocytes that produce or are capable of producing antibodies that specifically bind to CXCR5. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, Academic Press, pp. 59-103 (1986)).

Generally, in making antibody-producing hybridomas, either peripheral blood lymphocytes ("PBLs") are used if cells of human origin are desired, or spleen cells or lymph node cells are used if non-human mammalian sources are desired. Immortalized cell lines are usually transformed mammalian cells, particularly myeloma cells of rodent, bovine or human origin. Typically, a rat or mouse myeloma cell line is employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin and thymidine ("HAT medium"), substances that prevent the growth of HGPRT-deficient cells.

Preferred immortalized cell lines are those that fuse efficiently, support stable high level production of antibody by the selected antibody-producing cells, and are sensitive to a medium such as HAT medium. Among these myeloma cell lines are murine myeloma lines, such as those derived from the MOPC-21 and MPC-11 mouse tumors available from the Salk Institute Cell Distribution Center, San Diego, Calif. and SP2/0, FO or X63-Ag8-653 cells available from the American Type Culture Collection, Manassas, Va.

Human myeloma and mouse-human heteromyeloma cell lines also have been described for the production of human monoclonal antibodies (Kozbor, J Immunol 133:3001 (1984); and Brodeur et al., Monoclonal Antibody Production Techniques and Applications, Marcel Dekker, Inc, pp. 51-63 (1987)). The mouse myeloma cell line NSO may also be used (European Collection of Cell Cultures, Salisbury, Wilshire, UK).

Another alternative is to use electrical fusion rather than chemical fusion to form hybridomas. Instead of fusion, a B cell can be immortalized using, for example, Epstein Barr Virus or another transforming gene, see, e.g., Zurawaki et al., in Monoclonal Antibodies, ed., Kennett et al., Plenum Press, pp. 19-33. (1980). Transgenic mice expressing immunoglobulins and severe combined immunodeficient (SCID) mice transplanted with human B lymphocytes also can be used.

The culture medium in which hybridoma cells are grown is assayed for production of monoclonal antibodies directed against CXCR5. The binding specificity of monoclonal antibodies produced by hybridoma cells may be determined by immunoprecipitation or by an in vitro binding assay, such as radioimmunoassay (RIA), fluorocytometric analysis (FACS) or enzyme-linked immunosorbent assay (ELISA). Such techniques are known in the art and are within the skill of the artisan. The binding affinity of the monoclonal antibody to CXCR5 can, for example, be determined by a Scatchard analysis (Munson et al., Anal Biochem 107:220 (1980)).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, Academic Press, pp. 59-103 (1986)). Suitable culture media include, for example, Dulbecco's Modified Eagle's Medium (D-MEM) or RPMI-1640 medium. In addition, the hybridoma cells may be grown in vivo as ascites tumors in an animal.

The monoclonal antibodies secreted by the subclones are suitably separated or isolated from the culture medium, ascites fluid or serum by conventional immunoglobulin purification procedures such as, for example, protein A-Sepharose, protein G-Sepharose, hydroxylapatite chromatography, gel exclusion chromatography, gel electrophoresis, dialysis or affinity chromatography.

A variety of methods exist in the art for the production of monoclonal antibodies and thus, the invention is not limited to their sole production in hybridomas. For example, the monoclonal antibodies may be made by recombinant DNA methods, such as those described in U.S. Pat. No. 4,816,567. In this context, the term "monoclonal antibody" refers to an antibody derived from a single eukaryotic, phage or prokaryotic clone.

DNA encoding the monoclonal antibodies of the invention is readily isolated and sequenced using conventional procedures (e.g., by using oligonucleotide probes that are capable of binding specifically to genes encoding the heavy and light chains of murine antibodies, or such chains from human, humanized or other sources) (Innis et al. in PCR Protocols. A Guide to Methods and Applications, Academic (1990), and Sanger et al., Proc Natl Acad Sci 74:5463 (1977)). The hybridoma cells serve as a source of such DNA. Once isolated, the DNA may be placed into expression vectors, which are then transfected into host cells such as E. coli cells, NS0 cells, COS cells, Chinese hamster ovary (CHO) cells or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567; and Morrison et al., Proc Natl Acad Sci USA 81:6851 (1984)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one CXCR5-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the $F_c$ region so as to prevent heavy chain cross-linking. Alternatively, the relevant cysteine residues are substituted with another amino acid residue or are deleted so as to prevent cross-linking.

Antibody fragments which recognize specific epitopes may be generated by known techniques. Traditionally, these fragments were derived via proteolytic digestion of intact antibodies (see, e.g., Morimoto et al., J Biochem Biophys Methods 24:107 (1992); and Brennan et al., Science 229:81 (1985)). For example, $F_{ab}$ and $F_{(ab')2}$ fragments of the invention may be produced by proteolytic cleavage of immunoglobulin molecules, using enzymes such as papain (to produce $F_{ab}$ fragments) or pepsin (to produce $F_{(ab')2}$ fragments). $F_{(ab')2}$ fragments contain the variable region, the light chain constant region and the constant region $C_{H1}$ domain of the heavy chain. However, those fragments can be produced directly by recombinant host cells. For example, the antibody fragments can be isolated from an antibody phage library. Alternatively, $F_{(ac')2}$-SH fragments can be directly recovered from E. coli and chemically coupled to form F(ab')$_2$ fragments (Carter et al., Bio/Technology 10:163 (1992). According to another approach, $F_{(ab')2}$ fragments can be isolated directly from recombinant host cell culture. Other techniques for the production of antibody fragments will be apparent to the skilled practitioner. In other embodiments, the antibody of choice is a single chain $F_v$ fragment ($F_v$) (WO 93/16185).

For some uses, including in vivo use of antibodies in humans and in vitro detection assays, it may be preferable to use chimeric, humanized or human antibodies. Methods for producing chimeric antibodies are known in the art, see e.g., Morrison, Science 229:1202 (1985); Oi et al., BioTechniques 4:214 (1986); Gillies et al., J Immunol Methods 125:191 (1989); and U.S. Pat. Nos. 5,807,715; 4,816,567; and 4,816,397.

Humanized antibodies are derived from antibody molecules generated in a non-human species that bind CXCR5 wherein one or more CDRs therefrom are inserted into the FR regions from a human immunoglobulin molecule. Antibodies can be humanized using a variety of techniques known in the art including, for example, CDR grafting (EPO 239,400; WO 91/09967; and U.S. Pat. Nos. 5,225,539; 5,530,101; and 5,585,089), veneering or resurfacing (EPO 592,106; EPO 519,596; Padlan, Molecular Immunology 28:489 (1991); Studnicka et al., Protein Engineering 7:805 (1994); and Roguska et al., Proc Natl Acad Sci USA 91:969 (1994)), and chain shuffling (U.S. Pat. No. 5,565,332).

A humanized antibody has one or more amino acid residues from a source that is non-human. The non-human amino acid residues are often referred to as "import" residues, which are typically taken from an "import" variable domain. Humanization can be essentially performed following the methods of Winter and co-workers (Jones et al., Nature 321: 522 (1986); Ricchmann et al., Nature 332:323 (1988); and Verhoeyen et al., Science 239:1534 (1988)), by substituting non-human CDRs or portions of CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possible some FR residues are substituted from analogous sites in rodent antibodies. The heavy chain constant region, which can include one or more heavy chain domains, and hinge region can be from any class or subclass to obtain a desired effect, such as a particular effector function.

Often, framework residues in the human framework regions can be substituted with the corresponding residue from the CDR donor antibody to alter, and possibly improve, antigen binding. The framework substitutions are identified by methods known in the art, e.g., by modeling of the interactions of the CDR and framework residues to identify framework residues important for antigen binding and sequence comparison to identify unusual framework residues at particular positions, see, e.g., U.S. Pat. No. 5,585,089; and Riechmann et al., Nature 332:323 (1988).

It is further preferable that humanized antibodies retain high affinity for CXCR5, and retain or acquire other favorable biological properties. Thus, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of the displays permits analysis of the likely role of certain residues in the functioning of the candidate immunoglobulin sequence, i.e., the analysis of residues that influence the ability of the candidate immunoglobulin to bind CXCR5. In that way, FR residues can be selected and combined from the recipient and import sequences so that the desired antibody characteristic, such as increased affinity for the target antigen, is maximized, although it is the CDR residues that directly and most substantially influence CXCR5 binding. The CDR regions also can be modified to contain one or more amino acids that vary from that obtained from the parent antibody from which the CDR was obtained, to provide enhanced or different properties of interest, such as binding of greater affinity or greater avidity, for example.

Certain portions of the constant regions of antibody can be manipulated and changed to provide antibody homologs, derivatives, fragments and the like with properties different from or better than that observed in the parent antibody. Thus, for example, many IgG4 antibodies form intrachain disulfide bonds near the hinge region. The intrachain bond can destabilize the parent bivalent molecule forming monovalent molecules comprising a heavy chain with the associated light chain. Such molecules can reassociate, but on a random basis.

It was observed that modifying amino acids in the hinge region of IgG4 molecules can reduce the likelihood of intrachain bond formation, thereby stabilizing the IgG4 molecule, which will minimize the likelihood of forming bispecific molecules. That modification can be beneficial if a therapeutic antibody is an IgG4 molecule as the enhanced stability will minimize the likelihood of having the molecule dissociate during production and manufacture, as well as in vivo. A monovalent antibody may not have the same effectiveness as the bivalent parent molecule. For example, when bivalent IgG4 is administered to a patient, the percentage of bivalent IgG4 decays to about 30% over a two-week period. An amino acid substitution at position 228 enhances IgG4 stability. The serine that resides at 228 can be replaced with another amino acid, such as one of the remaining 19 amino acids. Such a change can be made particularly with recombinant antibodies wherein the nucleic acid coding sequence can be mutated to yield a replacement amino acid at position 228. For example, the S can be replaced with a proline.

Another set of amino acids suitable for modification include amino acids in the area of the hinge which impact binding of a molecule containing a heavy chain with binding to the $F_c$ receptor and internalization of bound antibody. Such amino acids include, in IgG1 molecules, residues from about 233 to about 237 (Glu-Leu-Leu-Gly-Gly); (SEQ ID NO:49) from about 252 to about 256 (Met-Ile-Ser-Arg-Thr) (SEQ ID NO:50) and from about 318 (Glu) to about 331 (Pro), including, for example, $Lys_{320}$, $Lys_{322}$ and $Pro_{329}$.

Completely human antibodies are particularly desirable for therapeutic treatment of human patients. Human antibodies can be made by a variety of methods known in the art including phage display methods described above using antibody libraries derived from human immunoglobulin sequences, see, U.S. Pat. Nos. 4,444,887 and 4,716,111; and WO 98/46645, WO 98/50433, WO 98/24893, WO 98/16654, WO 96/34096, WO 96/33735 and WO 91/10741. The techniques of Cole et al. and Boerder et al. are also available for the preparation of human monoclonal antibodies (Cole et al., Monoclonal Antibodies and Cancer Therapy, Alan R. Liss (1985); and Boerner et al., J Immunol 147:86 (1991)).

Human antibodies can also be produced using transgenic mice which are incapable of expressing functional endogenous immunoglobulins, but which also express certain human immunoglobulin genes. For example, the human heavy and light chain immunoglobulin gene complexes may be introduced randomly or by homologous recombination into mouse embryonic stem cells. Alternatively, the human variable region, constant region and diversity region may be introduced into mouse embryonic stem cells, in addition to the human heavy and light chain genes. The mouse heavy and light chain immunoglobulin genes may be rendered nonfunctional separately or simultaneously with the introduction of the human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies, see, e.g., Jakobovitis et al., Proc Natl Acad Sci USA 90:2551 (1993); Jakobovitis et al., Nature 362:255

(1993); Bruggermann et al., Year in Immunol 7:33 (1993); and Duchosal et al., Nature 355:258 (1992)).

The transgenic mice are immunized in the normal fashion with a CXCR5, e.g., all or a portion of CXCR5, such as the EC domain thereof. Monoclonal antibodies directed against CXCR5 can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview, see Lonberg et al., Int Rev Immunol 13:65-93 (1995). For a discussion of producing human antibodies and human monoclonal antibodies and protocols for producing such antibodies, see, e.g., WO 98/24893; WO 92/01047; WO 96/34096; and WO 96/33735; EPO No. 0 598 877; and U.S. Pat. Nos. 5,413,923; 5,625,126; 5,633,425; 5,569,825; 5,661,016; 5,545,806; 5,814,318; 5,885,793; 5,916,771; and 5,939,598. In addition, companies such as Amgen (Fremont, Calif.), Genpharm (San Jose, Calif.) and Medarex, Inc. (Princeton, N.J.) can be engaged to provide human antibodies directed against CXCR5 using technology similar to that described above.

Also, human mAbs could be made by immunizing mice transplanted with human peripheral blood leukocytes, splenocytes or bone marrow (e.g., trioma technique of XTL Biopharmaceuticals, Israel). Completely human antibodies which recognize a selected epitope can be generated using a technique referred to as "guided selection." In that approach, a selected non-human monoclonal antibody, e.g., a mouse antibody, is used to guide the selection of a completely human antibody recognizing the same epitope (Jespers et al., Bio/technology 12:899 (1988)).

When using recombinant techniques, the antibody variant can be produced intracellularly, in the periplasmic space, or directly secreted into the medium. If the antibody variant is produced intracellularly, as a first step, the particulate debris, either host cells or lysed fragments, may be removed, for example, by centrifugation or ultrafiltration. Carter et al., Bio/Technology 10:163 (1992) describe a procedure for isolating antibodies which are secreted to the periplasmic space of *E. coli*. Briefly, cell paste is exposed to sodium acetate (pH 3.5) and EDTA. Cell debris can be removed by centrifugation. Where the antibody variant is secreted into the medium, supernatant from such expression systems are generally first concentrated using a commercially available protein concentration filter, for example, an Amicon or Millipore Pellicon ultrafiltration unit. A protease inhibitor such as PMSF may be included to inhibit proteolysis, and antibiotics may be included to prevent growth of adventitious contaminants.

The antibody composition prepared from the cells can be purified using, for example, hydroxylapatite chromatography, gel electrophoresis, dialysis and affinity chromatography. The suitability of protein A or protein G as an affinity ligand depends on the species and isotype of any immunoglobulin $F_v$ domain that is present in the antibody variant. Protein A can be used to purify antibodies that are based on human IgG1, IgG2 or IgG4 heavy chains (Lindmark et al., J Immunol Meth 62:1 (1983)). Protein G can be used for mouse isotypes and for human IgG3 (Cuss et al., EMBO J. 5:1567 (1986)). The matrix to which the affinity ligand is attached is most often agarose, but other matrices are available. Mechanically stable matrices, such as controlled pore glass or poly(styrenedivinyl)benzene, allow for faster flow rates and shorter processing times than can be achieved with agarose. Where the antibody variant comprises a $C_{H3}$ domain, the Bakerbond ABX™ resin (JT Baker; Phillipsburg, N.J.) is useful for purification. Other techniques for protein purification, such as fractionation on an ion-exchange column, ethanol precipitation, reverse phase HPLC, chromatography on silica, chromatography on heparin agarose chromatography on an anion or cation exchange resin (such as a polyaspartic acid column), chromatofocusing, SDS-PAGE and ammonium sulfate precipitation are also available, depending on the antibody or variant to be recovered.

Following any preliminary purification step(s), the mixture comprising the antibody or variant of interest and contaminants may be subjected to low pH hydrophobic interaction chromatography using an elution buffer at a pH of between about 2.5-4.5, preferably performed at low salt concentrations (e.g., from about 0-0.25 M salt).

Further, antibodies of the invention can, in turn, be utilized to generate anti-idiotype antibodies that "mimic" CXCR5 using techniques well known to those skilled in the art (see, e.g., Greenspan et al., FASEB J 7:437 (1989); and Nissinoff, J Immunol 147:2429 (1991)). For example, antibodies which bind to and competitively inhibit multimerization and/or binding of a ligand to CXCR5 can be used to generate anti-idiotypes that "mimic" CXCR5 and binding domain and, as a consequence, bind to and neutralize CXCR5 and/or its ligand. Such neutralizing anti-idiotypes or $F_{ab}$ fragments of such anti-idiotypes can be used in therapeutic regimens, for example, to neutralize CXCL13.

The antibodies of the present invention may be bispecific antibodies. Bispecific antibodies can be monoclonal, preferably human or humanized, antibodies that have binding specificities for at least two different antigens. In the present invention, one of the binding specificities is directed towards CXCR5, the other may be for any other antigen, such as a cell-surface protein, receptor, receptor subunit, ligand, tissue-specific antigen, virally-derived protein, virally-encoded envelope protein, bacterially-derived protein, bacterial surface protein etc. Thus, the other specificity could be to CXCL13.

Methods for making bispecific antibodies are well known. Traditionally, the recombinant production of bispecific antibodies is based on the co-expression of two immunoglobulin heavy chain/light chain pairs, where the two heavy chains have different specificities (Milstein et al., Nature 305:537 (1983)). Because of the random assortment of immunoglobulin heavy and light chains, the hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829 and in Traunecker et al., EMBO J. 10:3655 (1991). Other methods for making bispecific antibodies are provided in, for example, Kufer et al., Trends Biotech 22:238-244, 2004.

Antibody variable domains with the desired binding specificities can be fused to immunoglobulin constant domain sequences. The fusion preferably is with an immunoglobulin heavy chain constant domain, comprising at least part of the hinge, $C_{H2}$, and $C_{H3}$ regions. It may have the first heavy chain constant region ($C_{H1}$) containing the site necessary for light chain binding present in at least one of the fusions. DNAs encoding the immunoglobulin heavy chain fusions and, if desired, the immunoglobulin light chain, are inserted into separate expression vectors, and are co-transformed into a suitable host organism. For further details of generating bispecific antibodies see, for example Suresh et al., Meth Enzym 121:210 (1986).

Heteroconjugate antibodies are also contemplated by the present invention. Heteroconjugate antibodies are composed of two covalently joined antibodies. Such antibodies have, for example, been proposed to target immune system cells to unwanted cells (U.S. Pat. No. 4,676,980). It is contemplated that the antibodies may be prepared in vitro using known methods in synthetic protein chemistry, including those involving cross-linking agents. For example, immunotoxins may be constructed using a disulfide exchange reaction or by forming a thioester bond. Examples of suitable reagents for that purpose include iminothiolate and methyl-4-mercaptobutyrimidate, and those disclosed, for example, in U.S. Pat. No. 4,676,980.

In addition, one can generate single-domain antibodies to CXCR5. Examples of that technology have been described in WO9425591 for antibodies derived from Camelidae heavy chain Ig, as well as in US20030130496 describing the isolation of single domain fully human antibodies from phage libraries.

Alternatively, techniques described for the production of single chain antibodies (U.S. Pat. No. 4,946,778; Bird, Science 242:423 (1988); Huston et al., Proc Natl Acad Sci USA 85:5879 (1988); and Ward, et al., Nature 334:544 (1989)) can be adapted to produce single chain antibodies. Single chain antibodies are formed by linking the heavy and light chain fragments of the $F_v$ region via an amino acid bridge, resulting in a single chain polypeptide. Techniques for the assembly of functional $F_v$ fragments in *E. coli* may also be used (Skerra et al., Science 242:1038 (1988)).

The instant invention encompasses antibodies recombinantly fused or chemically conjugated (including both covalently and non-covalently conjugations) to a polypeptide. Fused or conjugated antibodies of the present invention may be used for ease in purification, see e.g., WO 93/21232; EP 439,095; Naramura et al., Immunol Lett 39:91 (1994); U.S. Pat. No. 5,474,981; Gillies et al., Proc Natl Acad Sci USA 89:1428 (1992); and Fell et al., J Immunol 146:2446 (1991). The marker amino acid sequence can be a hexa-histidine peptide (SEQ ID NO:51), such as the tag provided in a pQE vector (QIAGEN, Inc., Chatsworth, Calif.), among others, many of which are commercially available, Gentz et al., Proc Natl Acad Sci USA 86:821 (1989). Other peptide tags useful for purification include, but are not limited to, the "HA" tag, which corresponds to an epitope derived from the influenza hemagglutinin protein (Wilson et al., Cell 37:767 (1984)) and the "flag" tag.

One can also create a single peptide chain binding molecules in which the heavy and light chain $F_v$ regions are connected. Single chain antibodies ("scF$_v$") and the method of their construction are described in, for example, U.S. Pat. No. 4,946,778. Alternatively, $F_{ab}$ can be constructed and expressed by similar means. All of the wholly and partially human antibodies can be less immunogenic than wholly murine mAbs, and the fragments and single chain antibodies also can be less immunogenic.

Antibodies or antibody fragments can be isolated from antibody phage libraries generated using the techniques described in McCafferty et al., Nature 348:552 (1990). Clarkson et al., Nature 352:624 (1991) and Marks et al., J Mol Biol 222:581 (1991) describe the isolation of murine and human antibodies, respectively, using phage libraries. Subsequent publications describe the production of high affinity (nM range) human antibodies by chain shuffling (Marks et al., Bio/Technology 10:779 (1992)), as well as combinatorial infection and in vivo recombination as a strategy for constructing very large phage libraries (Waterhouse et al., Nucl Acids Res 21:2265 (1993)). Thus, the techniques are viable alternatives to traditional monoclonal antibody hybridoma techniques for isolation of monoclonal antibodies.

Anti-CXCR5 antibodies are tested by enzyme-linked immunosorbent assay (ELISA), FACS, Western immunoblotting or other immunochemical techniques as known in the art. Thus, B cells or cells expressing CXCR5 can be used to detect antibody binding thereto using a known technique, or recombinantly expressed CXCR5 or portion thereof, such as the EC domain, can be adhered to a solid phase and used as a capture element in an assay, configured as a design choice.

To determine whether a particular antibody homolog binds to human CXCR5, any conventional binding assay may be used. Useful CXCR5 binding assays include FACS analysis, ELISA assays, radioimmunoassays and the like, which detect binding of antibody, and functions resulting therefrom, to human CXCR5. Full-length and soluble forms of human CXCR5 taught herein are useful in such assays. The binding of an antibody or homolog to CXCR5, or to soluble fragments thereof, may conveniently be detected through the use of a second antibody specific for immunoglobulins of the species from which the antibody or homolog is derived.

To determine whether a particular antibody or homolog does or does not significantly block binding of CXCL13 or other ligand to human CXCR5, any suitable competition assay may be used. Useful assays include, for example, ELISA assays, FACS assays, radioimmunoassays and the like that quantify the ability of the antibody or homolog to compete with CXCL13 or other ligand for binding to human CXCR5. Preferably, the ability of ligand to block binding of labeled human CXCR5 to immobilized antibody or homolog is measured.

The ability of an antibody or homolog to bind to human CXCR5 can be evaluated by testing the ability thereof to bind to human CXCR5$^+$ cells. Suitable CXCR5$^+$ cells for use in determining whether a particular antibody or homolog binds to human CXCR5 are mammal tissue culture cells transformed with DNA encoding full-length human CXCR5 and expressing the CXCR5 on the cell surface or B cell lines.

Binding of the antibody or homolog to the CXCR5$^+$ cell can be detected by staining the cells with a fluorescently-labeled second antibody specific for immunoglobulins of the same species from which the antibody homolog being tested is derived. A fluorescence activated cell sorter ("FACS") can be used to detect and to quantify any binding, see generally, Shapiro, Practical Flow Cytometry, Alan R. Liss, Inc., New York, N.Y. (1985).

Also, the ability of an antibody homolog to block binding of a ligand, such as CXCL13, to human CXCR5 can be determined by preincubating excess ligand with CXCR5$^+$ cells and quantifying the degree to which the bound ligand blocks binding of the antibody or homolog to the cells. Binding of the antibody homolog to the CXCR5$^+$ cells can be quantified by FACS analysis, using a fluorescently labeled second antibody specific for immunoglobulins of the same species from which the antibody homolog being tested is derived. Alternatively, a competition assay can be configured using labeled ligand or antibody as known in the art.

Ligand, such as CXCL13, used in the above assays may be provided by cells transformed with the gene for the ligand, or by isolated CXCL13, obtained practicing methods taught herein, or purchased commercially.

To determine whether a particular antibody or homolog causes no significant decrease in the number of circulating CXCR5$^+$ cells in vivo, the number of circulating CXCR5$^+$ cells isolated from a mammal within 24 hours after administration of the antibody or homolog to a mammal having normal immune function is quantified, and compared to the pre-administration number or the number in a control mammal to whom an isotype-matched antibody or homolog of irrelevant specificity has been administered instead of an antibody or homolog of the instant invention. Quantification of CXCR5+ cells in animals dosed with a CXCR5 antibody or functional portion or derivative thereof may be accomplished, for example, by staining obtained cells with fluorescently-labeled antibodies that bind the anti-CXCR5 antibodies, as well as labeled antibodies specific for T cells and B cells, followed by FACS analysis.

Antibodies of the instant invention may be described or specified in terms of the epitope(s) or portion(s) of CXCR5 to which the antibody recognizes or specifically binds. The epitope(s) or polypeptide portion(s) may be specified as described herein, e.g., by N-terminal and C-terminal positions, by size in contiguous amino acid residues, conformational epitopes and so on.

Antibodies of the instant invention may also be described or specified in terms of cross-reactivity. Antibodies that bind CXCR5 polypeptides, which have at least 95%, at least 90%, at least 85%, at least 80%, at least 75%, at least 70%, at least 65%, at least 60%, at least 55%, and at least 50% identity (as calculated using methods known in the art and described herein) to CXCR5 are also included in the instant invention.

Antibodies of the instant invention also may be described or specified in terms of binding affinity to a CXCR5 of interest. Anti-CXCR5 antibodies may bind with a $K_D$ of less than about $10^{-7}$ M, less than about $10^{-6}$ M, or less than about $10^{-5}$ M. Higher binding affinities in an antibody of interest can be beneficial, such as those with an equilibrium dissociation constant or $K_D$ of from about $10^{-8}$ to about $10^{-15}$ M, from about $10^{-8}$ to about $10^{-12}$ M, from about $10^{-9}$ to about $10^{-11}$ M, or from about $10^{-8}$ to about $10^{-10}$ M. The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

The instant invention also includes conjugates comprising an antibody of interest. The conjugates comprise two primary components, an antibody of interest and a second component, which may be a cell-binding agent, a cytotoxic agent and so on.

As used herein, the term "cell-binding agent" refers to an agent that specifically recognizes and binds to a molecule on the cell surface. Thus, the cell-binding agent can be a CD antigen, a pathogen antigen, such as a virus antigen, a differentiation antigen, a cancer antigen, a cell-specific antigen, a tissue-specific antigen, an Ig or Ig-like molecule and so on.

In one embodiment, the cell-binding agent specifically recognizes CXCL13 or the complex of CXCR5 and a ligand thereof, such as CXCL13. The conjugate may be in contact with the target cell for a sufficient period of time to allow an effector function of the conjugate to act on the cell, and/or to allow the conjugate sufficient time in which to be internalized by the cell.

Cell-binding agents may be of any type as presently known, or that become known, and includes peptides, non-peptides, saccharides, nucleic acids, ligands, receptors and so on, or combinations thereof. The cell-binding agent may be any compound that can bind a cell, either in a specific or non-specific manner. Generally, the agent can be an antibody (especially monoclonal antibodies), lymphokines, hormones, growth factors, vitamins, nutrient-transport molecules (such as transferrin), or any other cell-binding molecule or substance.

Other examples of cell-binding agents that can be used include: polyclonal antibodies; monoclonal antibodies; and fragments of antibodies such as $F_{ab}$, $F_{ab'}$, $F_{(ab')2}$ and $F_v$ (Parham, J. Immunol. 131:2895-2902 (1983); Spring et al., J. Immunol. 113:470-478 (1974); and Nisonoff et al., Arch. Biochem. Biophys. 89: 230-244 (1960)).

The second component also can be a cytotoxic agent. The term "cytotoxic agent" as used herein refers to a substance that reduces or blocks the function, or growth, of cells and/or causes destruction of cells. Thus, the cytotoxic agent can be a taxol, a maytansinoid, such as DM1 or DM4, CC-1065 or a CC-1065 analog, a ricin, mitomycin C and so on. In some embodiments, the cytotoxic agent, as with any binding agent of a conjugate of the instant invention is covalently attached, directly or via a cleavable or non-cleavable linker, to an antibody of interest.

Examples of suitable maytansinoids include maytansinol and maytansinol analogs. Maytansinoids inhibit microtubule formation and are highly toxic to mammalian cells.

Examples of suitable maytansinol analogues include those having a modified aromatic ring and those having modifications at other positions. Such suitable maytansinoids are disclosed in U.S. Pat. Nos. 4,424,219; 4,256,746; 4,294,757; 4,307,016; 4,313,946; 4,315,929; 4,331,598; 4,361,650; 4,362,663; 4,364,866; 4,450,254; 4,322,348; 4,371,533; 6,333,410; 5,475,092; 5,585,499; and 5,846,545.

Examples of suitable analogues of maytansinol having a modified aromatic ring include: (1) C-19-dechloro (U.S. Pat. No. 4,256,746) (prepared, for example, by LAH reduction of ansamytocin P2); (2) C-20-hydroxy (or C-20-demethyl)+/− C-19-dechloro (U.S. Pat. Nos. 4,361,650 and 4,307,016) (prepared, for example, by demethylation using *Streptomyces* or *Actinomyces* or dechlorination using lithium aluminum hydride (LAH)); and (3) C-20-demethoxy, C-20-acyloxy (—OCOR), +/−dechloro (U.S. Pat. No. 4,294,757) (prepared by acylation using acyl chlorides).

Examples of suitable analogues of maytansinol having modifications of other positions include: (1) C-9-SH (U.S. Pat. No. 4,424,219) (prepared by the reaction of maytansinol with $H_2S$ or $P_2S_5$); (2) C-14-alkoxymethyl (demethoxy/ $CH_2OR$) (U.S. Pat. No. 4,331,598); (3) C-14-hydroxymethyl or acyloxymethyl ($CH_2OH$ or $CH_2OAc$) (U.S. Pat. No. 4,450,254) (prepared from *Nocardia*); (4) C-15-hydroxy/acyloxy (U.S. Pat. No. 4,364,866) (prepared by the conversion of maytansinol by *Streptomyces*); (5) C-15-methoxy (U.S. Pat. Nos. 4,313,946 and 4,315,929) (isolated from *Trewia nudiflora*); (6) C-18-N-demethyl (U.S. Pat. Nos. 4,362,663 and 4,322,348) (prepared by the demethylation of maytansinol by *Streptomyces*); and (7) 4,5-deoxy (U.S. Pat. No. 4,371,533) (prepared by the titanium trichloride/LAH reduction of maytansinol).

The cytotoxic conjugates may be prepared by in vitro methods. To link a cytotoxic agent, drug or prodrug to the antibody, commonly, a linking group is used. Suitable linking groups are known in the art and include disulfide groups, thioether groups, acid labile groups, photolabile groups, peptidase labile groups and esterase labile groups. For example, conjugates can be constructed using a disulfide exchange reaction or by forming a thioether bond between an antibody of interest and the drug or prodrug.

As discussed above, the instant invention provides isolated nucleic acid sequences encoding an antibody or functional variant thereof as disclosed herein, vector constructs comprising a nucleotide sequence encoding the CXCR5-binding polypeptides of the present invention, host cells comprising such a vector, and recombinant techniques for the production of the polypeptide.

The vector normally contains components known in the art and generally include, but are not limited to, one or more of the following: a signal sequence, an origin of replication, one or more marker or selection genes, sequences facilitating and/or enhancing translation, an enhancer element and so on. Thus, the expression vectors include a nucleotide sequence operably linked to such suitable transcriptional or translational regulatory nucleotide sequences such as those derived from mammalian, microbial, viral or insect genes. Examples of additional regulatory sequences include operators, mRNA ribosomal binding sites, and/or other appropriate sequences which control transcription and translation, such as initiation and termination thereof. Nucleotide sequences are "operably linked" when the regulatory sequence functionally relates to the nucleotide sequence for the appropriate polypeptide. Thus, a promoter nucleotide sequence is operably linked to, e.g., the antibody heavy chain sequence if the promoter nucleotide sequence controls the transcription of that nucleotide sequence.

In addition, sequences encoding appropriate signal peptides that are not naturally associated with antibody heavy and/or light chain sequences can be incorporated into expression vectors. For example, a nucleotide sequence for a signal peptide (secretory leader) may be fused in-frame to the polypeptide sequence so that the antibody is secreted to the periplasmic space or into the medium. A signal peptide that is functional in the intended host cells enhances extracellular secretion of the appropriate antibody or portion thereof. The signal peptide may be cleaved from the polypeptide on secretion of antibody from the cell. Examples of such secretory signals are well known and include, e.g., those described in U.S. Pat. Nos. 5,698,435; 5,698,417; and 6,204,023.

The vector may be a plasmid, a single-stranded or double-stranded viral vector, a single-stranded or double-stranded RNA or DNA phage vector, a phagemid, a cosmid or any other carrier of a transgene of interest. Such vectors may be introduced into cells as polynucleotides by well known techniques for introducing DNA and RNA into cells. The vectors, in the case of phage and viral vectors also may be introduced into cells as packaged or encapsulated virus by well known techniques for infection and transduction. Viral vectors may be replication competent or replication defective. In the latter case, viral propagation generally will occur only in complementing host cells and using plural vectors carrying the various virus components necessary to produce a particle. Cell-free translation systems may also be employed to produce the protein using RNAs derived from the present DNA constructs (see, e.g., WO 86/05807 and WO 89/01036; and U.S. Pat. No. 5,122,464).

The antibodies of the present invention can be expressed from any suitable host cell. Examples of host cells useful in the instant invention include prokaryotic, yeast or higher eukaryotic cells and include but are not limited to microorganisms such as bacteria (e.g., *E. coli, B. subtilis, Enterobacter, Erwinia, Klebsiella, Proteus, Salmonella, Serratia,* and *Shigella,* as well as *Bacilli, Pseudomonas* and *Streptomyces*) transformed with recombinant bacteriophage DNA, plasmid DNA or cosmid DNA expression vectors containing the antibody coding sequences of interest; yeast (e.g., *Saccharomyces, Pichia, Actinomycetes, Kluyveromyces, Schizosaccharomyces, Candida, Trichoderma, Neurospora,* and filamentous fungi, such as *Neurospora, Penicillium, Tolypocladium* and *Aspergillus*) transformed with recombinant yeast expression vectors containing antibody coding sequences; insect cell systems infected with recombinant virus expression vectors (e.g., Baculovirus) containing antibody coding sequences; plant cell systems infected with recombinant virus expression vectors (e.g., cauliflower mosaic virus, CaMV; or tobacco mosaic virus, TMV) or transformed with recombinant plasmid expression vectors (e.g., Ti plasmid) containing antibody coding sequences; or mammalian cell systems (e.g., COS, CHO, BHK, 293 or 3T3 cells) harboring recombinant expression constructs containing promoters derived from the genome of mammalian cells (e.g., metallothionein promoter) or from mammalian viruses (e.g., the adenovirus late promoter; or the vaccinia virus 7.5K promoter).

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids, such as pKK223-3 (Pharmacia Fine Chemicals, Uppsala, Sweden), pGEM1 (Promega Biotec, Madison, Wis.), pET (Novagen, Madison, Wis.) and the pRSET (Tnvitrogen, Carlsbad, Calif.) series of vectors (Studier, J Mol Biol 219:37 (1991); and Schoepfer, Gene 124:83 (1993)). Promoter sequences commonly used for recombinant prokaryotic host cell expression vectors include T7, (Rosenberg et al., Gene 56:125 (1987)), β-lactamase (penicillinase), lactose promoter system (Chang et al., Nature 275:615 (1978); and Goeddel et al., Nature 281:544 (1979)), tryptophan (trp) promoter system (Goeddel et al., Nucl Acids Res 8:4057 (1980)), and tac promoter (Sambrook et al., Molecular Cloning, A Laboratory Manual, 2nd ed., Cold Spring Harbor Laboratory (1990)).

Yeast vectors will often contain an origin of replication sequence, such as from a 2μ yeast plasmid, an autonomously replicating sequence (ARS), a promoter region, sequences for polyadenylation, sequences for transcription termination and a selectable marker gene. Suitable promoter sequences for yeast vectors include, among others, promoters for metallothionein, 3-phosphoglycerate kinase (Hitzeman et al., J Biol Chem 255:2073 (1980)) or other glycolytic enzymes (Holland et al., Biochem 17:4900 (1978)) such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase and glucokinase. Other suitable vectors and promoters for use in yeast expression are further described in Fleer et al., Gene 107:285 (1991). Other suitable promoters and vectors for yeast and yeast transformation protocols are well known in the art. Yeast transformation protocols are well known. One such protocol is described by Hinnen et al., Proc Natl Acad Sci 75:1929 (1978), which selects for Trp$^+$ transformants in a selective medium.

Any eukaryotic cell culture is workable, whether from vertebrate or invertebrate culture. Examples of invertebrate cells include plant and insect cells (Luckow et al., Bio/Technology 6:47 (1988); Miller et al., Genetic Engineering, Setlow et al., eds., vol. 8, pp. 277-9, Plenum Publishing (1986); and Maeda et al., Nature 315:592 (1985)). For example, Baculovirus systems may be used for production of heterologous proteins. In an insect system, *Autographa californica* nuclear polyhedrosis virus (AcNPV) may be used as a vector to express foreign genes. The virus grows in *Spodoptera frugiperda* cells. The antibody coding sequence may be cloned under control of an AcNPV promoter (for example the polyhedrin promoter). Other hosts that have been identified include *Aedes, Drosophila melanogaster* and *Bombyx mori*. A variety of viral strains for transfection are publicly available, e.g., the L-1 variant of AcNPV and the Bm-5 strain of *Bombyx mori* NPV. Moreover, plant cell cultures of cotton, corn, potato, soybean, petunia, tomato, and tobacco and also be utilized as hosts as known in the art.

Vertebrate cells, and propagation of vertebrate cells, in culture (tissue culture) can be a routine procedure, although fastidious cell lines do exist which require, for example, a specialized medium with unique factors, feeder cells and so on, see Tissue Culture, Kruse et al., eds., Academic Press (1973). Examples of useful mammal host cell lines are monkey kidney; human embryonic kidney line; baby hamster kidney cells; Chinese hamster ovary cells/–DHFR (CHO, Urlaub et al., Proc Natl Acad Sci USA 77:4216 (1980)); mouse sertoli cells; human cervical carcinoma cells (for example, HeLa); canine kidney cells; human lung cells; human liver cells; mouse mammary tumor; and NS0 cells.

Host cells are transformed with vectors for antibody production and cultured in conventional nutrient medium containing growth factors, vitamins, minerals and so on, as well as inducers appropriate for the cells and vectors used. Commonly used promoter sequences and enhancer sequences are derived from polyoma virus, Adenovirus 2, Simian virus 40 (SV40) and human cytomegalovirus (CMV). DNA sequences derived from the SV40 viral genome may be used to provide other genetic elements for expression of a structural gene sequence in a mammalian host cell, e.g., SV40 origin, early and late promoter, enhancer, splice and polyadenylation sites. Viral early and late promoters are particularly useful because both are easily obtained from a viral genome as a fragment which may also contain a viral origin of replication. Exemplary expression vectors for use in mammalian host cells are commercially available.

Commercially available medium such as Ham's F10, Minimal Essential Medium (MEM), RPMI-1640 and Dulbecco's Modified Eagle's Medium (DMEM) are suitable for culturing host cells. In addition, any of the media described in Ham et al., Meth Enzymol 58:44 (1979) and Barnes et al., Anal Biochem 102:255 (1980), and in U.S. Pat. Nos. 4,767,704; 4,657,866; 4,560,655; 5,122,469; 5,712,163; or 6,048,728 may be used as a culture medium for the host cells. Any of those media may be supplemented as necessary with hormones and/or other growth factors (such as insulin, transferrin or epidermal growth factor), salts (such as chlorides, such as sodium, calcium or magnesium chloride; and phosphates), buffers (such as HEPES), nucleotides (such as adenosine and thymidine), antibiotics, trace elements (defined as inorganic compounds usually present at final concentrations in the micromolar range) and glucose or an equivalent energy source. Any other necessary supplements may be included at appropriate concentrations, as a design choice. The culture conditions, such as temperature, pH and the like, are as known in the art appropriate for the cell and to enable the desired expression of the transgene.

The polynucleotides of interest may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., Bio/Techniques 17:242 (1994)) and then amplifying the ligated oligonucleotides, for example, by PCR.

Alternatively, a polynucleotide encoding an antibody may be generated from nucleic acid of a cell expressing same. If a clone containing a nucleic acid encoding a particular antibody is not available, but the sequence of the antibody molecule is known, a nucleic acid encoding the immunoglobulin may be obtained from a suitable source, such as a library, which may be one specific for antibody-producing cells, such as hybridoma cells selected to express an antibody of the invention. Suitable primers can be configured for PCR amplification. Amplified nucleic acids generated by PCR may then be cloned into replicable cloning vectors using any method well known in the art.

Once the nucleotide sequence and corresponding amino acid sequence of the antibody are determined, the nucleotide sequence of the antibody may be manipulated to obtain the equivalents of interest described herein using methods known in the art for manipulating nucleotide sequences, e.g., recombinant DNA techniques, site directed mutagenesis, PCR etc. (see, for example, Sambrook et al., Molecular Cloning, A Laboratory Manual, 2nd ed., Cold Spring Harbor Laboratory (1990); and Ausubel et al., eds., Current Protocols in Molecular Biology, John Wiley & Sons (1998) to generate antibodies having a different amino acid sequence, for example, to create amino acid substitutions, deletions and/or insertions.

The amino acid sequence of the heavy and/or light chain variable domain may be inspected to identify the sequences of the CDRs by well known methods, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The polynucleotide of interest generated by the combination of the framework regions and one or more CDRs encodes an antibody that specifically binds CXCR5, or at least the ED domain thereof. For example, such methods may be used to make amino acid substitutions or deletions of one or more variable region cysteine residues participating in an intrachain disulfide bond to generate antibody molecules lacking one or more intrachain disulfide bonds.

The antibodies or antibody fragments of the invention can be used to detect CXCR5, and hence cells expressing CXCR5, in a biological sample in vitro or in vivo. In one embodiment, the anti-CXCR5 antibody of the invention is used to determine the presence and the level of CXCR5 in a tissue or in cells derived from the tissue. The levels of CXCR5 in the tissue or biopsy can be determined, for example, in an immunoassay with the antibodies or antibody fragments of the invention. The tissue or biopsy thereof can be frozen or fixed. The same or other methods can be used to determine other properties of CXCR5, such as the level thereof, cellular localization, mRNA levels, mutations thereof and so on.

The above-described method can be used, for example, to diagnose a cancer in a subject known to be or suspected to have a cancer, wherein the level of CXCR5 measured in said patient is compared with that of a normal reference subject or standard. The assay of interest also can be used to diagnose arthritis or other autoimmune diseases characterized by B cell infiltration and concentration, along with development of differentiated lymphoid tissue.

The instant invention further provides for monoclonal antibodies, humanized antibodies and epitope-binding fragments thereof that are further labeled for use in research or diagnostic applications. In some embodiments, the label is a radiolabel, a fluorophore, a chromophore, an imaging agent or a metal ion.

A method for diagnosis is also provided in which said labeled antibodies or epitope-binding fragments thereof are administered to a subject suspected of having a cancer, arthritis, autoimmune diseases or other CXCR5 disease, and the distribution of the label within the body of the subject is measured or monitored.

The antibody and fragments thereof of the instant invention may be used as affinity purification agents. In that process, the antibodies are immobilized on a solid phase, such as a dextran or agarose resin or filter paper, using methods known in the art. The immobilized antibody is contacted with a sample containing CXCR5 or cells carrying same to be purified, and thereafter the support is washed with a suitable solvent that will remove substantially all the material in the sample except the CXCR5 or cell to be purified, which is bound to the immobilized antibody of interest. Finally, the support is washed with another suitable solvent, such as glycine buffer, pH 5.0, that will release the CXCR5 or cell from the antibody of interest.

For diagnostic applications, the antibody of interest typically will be labeled with a detectable moiety. Numerous labels are available which can be generally grouped into the following categories: (a) radioisotopes, such as $^{36}$S, $^{14}$C, $^{125}$I, $^{3}$H and $^{131}$I (The antibody can be labeled with the radioisotope using a techniques described in Current Protocols in Immunology, vol. 12, Coligen et al., ed., Wiley-Interscience, New York (1991), for example, and radioactivity can be measured using scintillation counting); (b) fluorescent labels, such as rare earth chelates (europium chelates), fluorescein and its derivatives, rhodamine and its derivatives, dansyl, lissamine, phycoerythrin and Texas Red, the fluorescent labels can be conjugated to the antibody using a technique disclosed in Current Protocols in Immunology, supra, for example, where fluorescence can be quantified using a fluorimeter; and (c) various enzyme substrate labels are available (U.S. Pat. No. 4,275,149 provides a review), the enzyme generally catalyzes a chemical alteration of the chromogenic substrate which can be measured using various techniques, for example, the enzyme may catalyze a color change in a substrate, which can be measured spectrophotometrically, or the enzyme may alter the fluorescence or chemiluminescence of the substrate. Techniques for quantifying a change in fluorescence are known, for example, using a luminometer, or the label donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase, such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase and the like. Techniques for conjugating enzymes to antibodies are described in O'Sullivan et al., Meth Enz, ed. Langone & Van Vunakis, Academic Press, New York, 73 (1981).

When such labels are used, suitable substrates are available, such as: (i) for horseradish peroxidase with hydrogen peroxidase as a substrate, wherein the hydrogen peroxidase oxidizes a dye precursor (e.g., orthophenylene diamine (OPD) or 3,3',5,5'-tetramethyl benzidine hydrochloride (TMB)); (ii) for alkaline phosphatase (AP) with p-nitrophenyl phosphate as the chromogenic substrate; and (iii) β-D-galactosidase (β-D-Gal) with a chromogenic substrate (e.g., p-nitrophenyl-β-D-galactosidase) or a fluorogenic substrate such as 4-methylumbelliferyl-β-D-galactosidase.

Other enzyme-substrate combinations are available to those skilled in the art. For a general review, see U.S. Pat. Nos. 4,275,149 and 4,318,980.

Sometimes, the label is indirectly conjugated with the antibody. For example, the antibody can be conjugated with biotin and any of the reporters mentioned above can be conjugated with avidin, or vice versa. Biotin binds selectively to avidin and thus, the label can be conjugated with the antibody in that indirect manner. Alternatively, to achieve indirect conjugation of the label, the antibody is conjugated with a small hapten (e.g., digoxin) and one of the different types of labels or reporters mentioned above is conjugated with an anti-digoxin antibody. Thus, indirect conjugation of the label with the antibody or mutein can be achieved using a second antibody.

In another embodiment of the invention, the antibody need not be labeled, and the presence thereof can be detected using a labeled antibody which binds to the antibody, another form of a second antibody.

The antibodies of the present invention may be employed in any known assay method, such as competitive binding assays, direct and indirect sandwich assays, and immunoprecipitation assays. Zola, Monoclonal Antibodies: A Manual of Techniques (CRC Press, Inc. 1987).

Competitive binding assays rely on the ability of a labeled standard to compete with the test sample for binding with a limited amount of antibody. The amount of antigen in the test sample is inversely proportional to the amount of standard that becomes bound to the antibodies. To facilitate determining the amount of standard that becomes bound, the antibodies generally are insolubilized before or after the competition. As a result, the standard and test sample that are bound to the antibodies may conveniently be separated from the standard and test sample which remain unbound.

Sandwich assays involve the use of two antibodies, each capable of binding to a different immunogenic portion, determinant or epitope, of the target to be detected. In a sandwich assay, the test sample to be analyzed is bound by a first antibody which is immobilized directly or indirectly on a solid support, and thereafter a second antibody directly or indirectly labeled binds to the bound test sample, thus forming an insoluble three-part complex, see e.g., U.S. Pat. No. 4,376,110. The second antibody may itself be labeled with a detectable moiety (direct sandwich assays) or may be measured using an anti-immunoglobulin antibody or other suitable member of the binding pair (antibody/antigen, receptor/ligand, enzyme/substrate, for example) that is labeled with a detectable moiety (indirect sandwich assay). For example, one type of sandwich assay is an ELISA assay, in which case the detectable moiety is an enzyme.

For immunohistochemistry, the cell or tissue sample may be fresh or frozen or may be embedded in paraffin and fixed with a preservative such as formalin, for example.

The antibodies may also be used for in vivo diagnostic assays. Generally, the antibody mutant is labeled with a radionucleotide (such as $^{111}$In, $^{99}$Tc, $^{14}$C, $^{131}$I, $^{3}$H, $^{32}$P or $^{35}$S) so that the sites expressing CXCR5 can be localized using immunoscintography.

The instant invention also includes kits, e.g., comprising an antibody, fragment thereof, homolog, derivative thereof and so on, such as a labeled or cytotoxic conjugate, and instructions for the use of the antibody, conjugate for killing particular cell types and so on. The instructions may include directions for using the antibody, conjugate and so on in vitro, in vivo or ex vivo. The antibody can be in liquid form or as a solid, generally lyophilized. The kit can contain suitable other reagents, such as a buffer, a reconstituting solution and other necessary ingredients for the intended use. A packaged combination of reagents in predetermined amounts with instructions for use thereof, such as for a therapeutic use of for performing a diagnostic assay is contemplated. Where the antibody is labeled, such as with an enzyme, the kit can include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied to provide for concentrates of a solution of a reagent, which provides user flexibility, economy of space, economy of reagents and so on. The reagents may be provided as dry powders, usually lyophilized, including excipients, which on dissolution provide a reagent solution having the appropriate concentration.

The antibodies of the present invention may be used to treat a mammal. In one embodiment, the antibody or equivalent of interest is administered to a nonhuman mammal for the purposes of obtaining preclinical data, for example. Exemplary nonhuman mammals to be treated include nonhuman primates, dogs, cats, rodents and other mammals in which preclinical studies are performed. Such mammals may be established animal models for a disease to be treated with the antibody, or may be used to study toxicity of the antibody of interest. In each of those embodiments, dose escalation studies may be performed in the mammal.

An antibody, with or without a second component, such as a therapeutic moiety conjugated to same, administered alone or in combination with cytotoxic factor(s) can be used as a therapeutic. The present invention is directed to antibody-based therapies which involve administering antibodies of the invention to an animal, a mammal, or a human, for treating a CXCR5-mediated disease, disorder or condition. The animal or subject may be a mammal in need of a particular treatment, such as a mammal having been diagnosed with a particular disorder, e.g., one relating to CXCR5. Antibodies directed against CXCR5 are useful, for example, for prophylaxis or treatment of arthritis, inflammatory diseases, in general, graft rejection, cancer and autoimmune disorders. For example, by administering a therapeutically acceptable dose of an anti-CXCR5 antibody of the instant invention, or a cocktail of a plurality of the instant antibodies or equivalents thereof, or in combination with other antibodies of varying sources, disease symptoms may be ameliorated or prevented in the treated mammal, particularly humans.

Therapeutic compounds of the invention include, but are not limited to, antibodies of the invention (including fragments, analogs, equivalents and derivatives thereof as described herein) and nucleic acids encoding antibodies of the invention as described herein (including fragments, analogs and derivatives thereof) and anti-idiotypic antibodies as described herein. The antibodies of the invention can be used to treat, inhibit or prevent diseases, disorders or conditions associated with aberrant expression and/or activity of CXCR5, including, but not limited to, any one or more of the diseases, disorders, or conditions described herein. The treatment and/or prevention of diseases, disorders or conditions associated with aberrant expression and/or activity of CXCR5 includes, but is not limited to, alleviating at least one symptom associated with those diseases, disorders, or conditions. Antibodies of the invention may be provided in pharmaceutically acceptable compositions as known in the art or as described herein. The term "physiologically acceptable," "pharmacologically acceptable" and so on mean approved by a regulatory agency of the Federal or a state government or listed in the U.S. Pharmacopeia or other generally recognized pharmacopeia for use in animals and more particularly in humans.

The anti-CXCR5 antibody can be administered to a mammal in any acceptable manner. Methods of introduction include, but are not limited to, parenteral, subcutaneous, intraperitoneal, intrapulmonary, intranasal, epidural, inhalation and oral routes, and if desired for immunosuppressive treatment, intralesional administration. Parenteral infusions include intramuscular, intradermal, intravenous, intraarterial or intraperitoneal administration. The antibodies or compositions may be administered by any convenient route, for example, by infusion or bolus injection, by absorption through epithelial or mucocutaneous linings (e.g., oral mucosa, rectal and intestinal mucosa etc.) and may be administered together with other biologically active agents. Administration can be systemic or local. In addition, it may be desirable to introduce the therapeutic antibodies or compositions of the invention into the central nervous system by any suitable route, including intraventricular and intrathecal injection; intraventricular injection may be facilitated by an intraventricular catheter, for example, attached to a reservoir, such as an Ommaya reservoir. In addition, the antibody is suitably administered by pulse infusion, particularly with declining doses of the antibody. Preferably the dosing is given by injection, preferably intravenous or subcutaneous injections, depending, in part, on whether the administration is brief or chronic.

Various other delivery systems are known and can be used to administer an antibody of the present invention, including, e.g., encapsulation in liposomes, microparticles, microcapsules (see Langer, Science 249:1527 (1990); Treat et al., in Liposomes in the Therapy of Infectious Disease and Cancer; Lopez-Berestein et al., eds., p. 353-365 (1989); and Lopez-Berestein, ibid., p. 317-327) and recombinant cells capable of expressing the compound; receptor-mediated endocytosis (see, e.g., Wu et al., J Biol Chem 262:4429 (1987)); construction of a nucleic acid as part of a retroviral or other vector etc.

The active ingredients may also be entrapped in microcapsule prepared, for example, by coascervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nanoparticles and nanocapsules) or in macroemulsions. Such techniques are disclosed in Remington's Pharmaceutical Sciences, 16th edition, A. Osal, Ed. (1980).

Pulmonary administration can also be employed, e.g., by use of an inhaler or nebulizer, and formulation with an aerosolizing agent. The antibody may also be administered into the lungs of a patient in the form of a dry powder composition, see e.g., U.S. Pat. No. 6,514,496.

In a specific embodiment, it may be desirable to administer the therapeutic antibodies or compositions of the invention locally to the area in need of treatment; that may be achieved by, for example, and not by way of limitation, local infusion, topical application, by injection, by means of a catheter, by means of a suppository or by means of an implant, said implant being of a porous, non-porous or gelatinous material, including membranes, such as sialastic membranes or fibers. Preferably, when administering an antibody of the invention, care is taken to use materials to which the protein does not absorb or adsorb.

In yet another embodiment, the antibody can be delivered in a controlled release system. In one embodiment, a pump may be used (see Langer, Science 249:1527 (1990); Sefton, CRC Crit Ref Biomed Eng 14:201 (1987); Buchwald et al., Surgery 88:507 (1980); and Saudek et al., N Engl J Med 321:574 (1989)). In another embodiment, polymeric materials can be used (see Medical Applications of Controlled Release, Langer et al., eds., CRC Press (1974); Controlled Drug Bioavailability, Drug Product Design and Performance, Smolen et al., eds., Wiley (1984); Ranger et al., J Macromol Sci Rev Macromol Chem 23:61 (1983); see also Levy et al., Science 228:190 (1985); During et al., Ann Neurol 25:351 (1989); and Howard et al., J Neurosurg 71:105 (1989)). In yet another embodiment, a controlled release system can be placed in proximity of the therapeutic target.

Therapeutic formulations of the polypeptide or antibody may be prepared for storage as lyophilized formulations or aqueous solutions by mixing the polypeptide having the desired degree of purity with optional "pharmaceutically acceptable" carriers, diluents, excipients or stabilizers typically employed in the art, i.e., buffering agents, stabilizing agents, preservatives, isotonifiers, non-ionic detergents, antioxidants and other miscellaneous additives, see Remington's Pharmaceutical Sciences, 16th ed., Osol, ed. (1980). Such additives are generally nontoxic to the recipients at the dosages and concentrations employed, hence, the excipients, diluents, carriers and so on are pharmaceutically acceptable.

An "isolated" or "purified" antibody is substantially free of cellular material or other contaminating proteins from the cell or tissue source or medium from which the protein is derived, or substantially free of chemical precursors or other chemicals when chemically synthesized. The language "substantially free of cellular material" includes preparations of an antibody in which the polypeptide/protein is separated from cellular components of the cells from which same is isolated or recombinantly produced. Thus, an antibody that is substantially free of cellular material includes preparations of the antibody having less than about 30%, 20%, 10%, 5%, 2.5% or 1%, (by dry weight) of contaminating protein. When the antibody is recombinantly produced, it is also preferably substantially free of culture medium, i.e., culture medium represents less than about 20%, 10%, 5%, 2.5% or 1% of the volume of the protein preparation. When antibody is produced by chemical synthesis, it is preferably substantially free of chemical precursors or other chemicals and reagents, i.e., the antibody of interest is separated from chemical precursors or other chemicals which are involved in the synthesis of the protein. Accordingly, such preparations of the antibody have less than about 30%, 20%, 10%, 5% or 1% (by dry weight) of chemical precursors or compounds other than antibody of interest. In a preferred embodiment of the present invention, antibodies are isolated or purified.

As used herein, the phrase "low to undetectable levels of aggregation" refers to samples containing no more than 5%, no more than 4%, no more than 3%, no more than 2%, no more than 1% and often no more than 0.5% aggregation, by weight protein, as measured by, for example, high performance size exclusion chromatography (HPSEC).

As used herein, the term "low to undetectable levels of fragmentation" refers to samples containing equal to or more than 80%, 85%, 90%, 95%, 98% or 99%, of the total protein, for example, in a single peak, as determined by HPSEC, or in two (2) peaks (heavy chain and light chain) by, for example, reduced capillary gel electrophoresis (rCGE) and containing no other single peaks having more than 5%, more than 4%, more than 3%, more than 2%, more than 1% or more than 0.5% of the total protein, each. The rCGE as used herein refers to capillary gel electrophoresis under reducing conditions sufficient to reduce disulfide bonds in an antibody or antibody-type or derived molecule.

As used herein, the terms "stability" and "stable" in the context of a liquid formulation comprising a CXCR5 antibody or binding fragment thereof refer to the resistance of the antibody or antigen-binding fragment thereof in the formulation to thermal and chemical unfolding, aggregation, degradation or fragmentation under given manufacture, preparation, transportation and storage conditions. The "stable" formulations of the invention retain biological activity equal to or more than 80%, 85%, 90%, 95%, 98%, 99% or 99.5% under given manufacture, preparation, transportation and storage conditions. The stability of said antibody preparation can be assessed by degrees of aggregation, degradation or fragmentation by methods known to those skilled in the art, including, but not limited to, rCGE, sodium dodecyl sulfate polyacrylamide gel electrophoresis (SDS-PAGE) and HPSEC, compared to a reference.

The term, "carrier," refers to a diluent, adjuvant, excipient or vehicle with which the therapeutic is administered. Such physiological carriers can be sterile liquids, such as water and oils, including those of petroleum, animal, vegetable or synthetic origin, such as peanut oil, soybean oil, mineral oil, sesame oil and the like. Water is a suitable carrier when the pharmaceutical composition is administered intravenously. Saline solutions and aqueous dextrose and glycerol solutions also can be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents. The compositions can take the form of solutions, suspensions, emulsion, tablets, pills, capsules, powders, sustained-release formulations, depots and the like. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate etc. Examples of suitable carriers are described in "Remington's Pharmaceutical Sciences," Martin. Such compositions will contain an effective amount of the antibody, preferably in purified form, together with a suitable amount of carrier so as to provide the form for proper administration to the patient. As known in the art, the formulation will be constructed to suit the mode of administration.

Buffering agents help to maintain the pH in the range which approximates physiological conditions. Buffers are preferably present at a concentration ranging from about 2 mM to about 50 mM. Suitable buffering agents for use with the instant invention include both organic and inorganic acids, and salts thereof, such as citrate buffers (e.g., monosodium citrate-disodium citrate mixture, citric acid-trisodium citrate mixture, citric acid-monosodium citrate mixture etc.), succinate buffers (e.g., succinic acid-monosodium succinate mixture, succinic acid-sodium hydroxide mixture, succinic acid-disodium succinate mixture etc.), tartrate buffers (e.g., tartaric acid-sodium tartrate mixture, tartaric acid-potassium tartrate mixture, tartaric acid-sodium hydroxide mixture etc.), fumarate buffers (e.g., fumaric acid-monosodium fumarate mixture, fumaric acid-disodium fumarate mixture, monosodium fumarate-disodium fumarate mixture etc.), gluconate buffers (e.g., gluconic acid-sodium glyconate mixture, gluconic acid-sodium hydroxide mixture, gluconic acid-potassium gluconate mixture etc.), oxalate buffers (e.g., oxalic acid-sodium oxalate mixture, oxalic acid-sodium hydroxide mixture, oxalic acid-potassium oxalate mixture etc.), lactate buffers (e.g., lactic acid-sodium lactate mixture, lactic acid-sodium hydroxide mixture, lactic acid-potassium lactate mixture etc.) and acetate buffers (e.g., acetic acid-sodium acetate mixture, acetic acid-sodium hydroxide mixture etc.). Phosphate buffers, carbonate buffers, histidine buffers, trimethylamine salts such as Tris, HEPES and other such known buffers can be used.

Preservatives may be added to retard microbial growth, and may be added in amounts ranging from 0.2%-1% (w/v). Suitable preservatives for use with the present invention include phenol, benzyl alcohol, m-cresol, methyl paraben, propyl paraben, octadecyldimethylbenzyl ammonium chloride, benzyaconium halides (e.g., chloride, bromide and iodide), hexamethonium chloride, alkyl parabens such as methyl or propyl paraben, catechol, resorcinol, cyclohexanol and 3-pentanol.

Isotonicifiers are present to ensure physiological isotonicity of liquid compositions of the instant invention and include polhydric sugar alcohols, preferably trihydric or higher sugar alcohols, such as glycerin, erythritol, arabitol, xylitol, sorbitol and mannitol. Polyhydric alcohols can be present in an amount of between about 0.1% to about 25%, by weight, preferably 1% to 5% taking into account the relative amounts of the other ingredients.

Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols; amino acids, such as arginine, lysine, glycine, glutamine, asparagine, histidine, alanine, ornithine, L-leucine, 2-phenylalanine, glutamic acid, threonine etc., organic sugars or sugar alcohols, such as lactose, trehalose, stachyose, arabitol, erythritol, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, $\alpha$-monothioglycerol and sodium thiosulfate; low molecular weight polypeptides (i.e., <10 residues); proteins, such as human serum albumin, bovine serum albumin, gelatin or immunoglobulins; hydrophilic polymers, such as polyvinylpyrrolidone, saccharides, monosaccharides, such as xylose, mannose, fructose, glucose; disaccharides, such as lactose, maltose and sucrose; trisaccharides such as raffinose; polysaccharides such as dextran and so on. Stabilizers are present in the range from 0.1 to 10,000 w/w per part of active protein.

Additional miscellaneous excipients include bulking agents, (e.g., starch), chelating agents (e.g., EDTA), antioxidants (e.g., ascorbic acid, methionine or vitamin E) and cosolvents.

The formulation herein also may contain more than one active compound as necessary for the particular indication being treated, preferably those with complementary activities that do not adversely impact each other. For example, it may be desirable to further provide an immunosuppressive agent. Such molecules suitably are present in combination in amounts that are effective for the purpose intended.

As used herein, the term "surfactant" refers to organic substances having amphipathic structures, namely, are composed of groups of opposing solubility tendencies, typically an oil-soluble hydrocarbon chain and a water-soluble ionic group. Surfactants can be classified, depending on the charge of the surface-active moiety, into anionic, cationic and non-ionic surfactants. Surfactants often are used as wetting, emulsifying, solubilizing and dispersing agents for various pharmaceutical compositions and preparations of biological materials.

Non-ionic surfactants or detergents (also known as "wetting agents") may be added to help solubilize the therapeutic agent, as well as to protect the therapeutic protein against agitation-induced aggregation, which also permits the formulation to be exposed to shear surface stresses without causing denaturation of the protein. Suitable non-ionic surfactants include polysorbates (20, 80 etc.), polyoxamers (184, 188 etc.), Pluronic® polyols and polyoxyethylene sorbitan monoethers (TWEEN-20°, TWEEN-80° etc.). Non-ionic surfactants may be present in a range of about 0.05 mg/ml to about 1.0 mg/ml, preferably about 0.07 mg/ml to about 0.2 mg/ml.

As used herein, the term, "inorganic salt," refers to any compound, containing no carbon, that result from replacement of part or all of the acid hydrogen or an acid by a metal or a group acting like a metal, and often are used as a tonicity adjusting compound in pharmaceutical compositions and preparations of biological materials. The most common inorganic salts are NaCl, KCl, $NaH_2PO_4$ etc.

The present invention provides liquid formulations of an anti-CXCR5-binding compound or fragment thereof, having a pH ranging from about 5.0 to about 7.0, or about 5.5 to 6.5, or about 5.8 to about 6.2, or about 6.0.

The instant invention encompasses liquid formulations having stability at temperatures found in a commercial refrigerator and freezer found in the office of a physician or laboratory, such as from about $-20°$ C. to about $5°$ C., said stability assessed, for example, by high performance size exclusion chromatography (HPSEC), for storage purposes, such as for about 60 days, for about 120 days, for about 180 days, for about a year, for about 2 years or more. The liquid formulations of the present invention also exhibit stability, as assessed, for example, by HSPEC, at room temperatures, for at least a few hours, such as one hour, two hours or about three hours prior to use.

The term "small molecule" and analogous terms include, but are not limited to, peptides, peptidomimetics, amino acids, amino acid analogues, polynucleotides, polynucleotide analogues, nucleotides, nucleotide analogues, organic or inorganic compounds (i.e., including heterorganic and/or ganometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Thus, in the case of cancer, for example, the antibodies of the invention may be administered alone or in combination with other types of cancer treatments, including conventional chemotherapeutic agents (paclitaxel, carboplatin, cisplatin and doxorubicin), anti-EGFR agents (gefitinib, erlotinib and cetuximab), anti-angiogenesis agents (bevacizumab and sunitinib), as well as immunomodulating agents, such as interferon $\alpha$ and thalidomide.

In another embodiment, in the case of rheumatic diseases, such as rheumatoid arthritis (RA), a combination therapy can be used comprising a CXCR-binding molecule of interest. For example, a humanized CXCR5 antibody can be dosed with a small molecule, such as a disease modifying antirheumatic drug, including, but not limited to, for example, methotrexate and pyridine synthesis inhibitors, such as, leflunomide (Mader & Keystone, J Rheum 34 Supp (16-24) 2007, Gaffo et al., Am J Health Syst Pharm 63:2451-2465, 2006).

Because various forms of a CXCR5-binding molecule of interest can be non-B cell-depleting, the instant molecule can be combined with other drugs having overlapping mechanisms of action to yield an additive or synergistic endpoint. Hence, for example, a second drug can be one which acts at the level of a cytokine, in the T cell axis and so on.

As used herein, the terms "therapeutic agent" and "therapeutic agents" refer to any agent(s) which can be used in the treatment, management or amelioration of a disease, disorder, malady and the like associated with aberrant CXCR5 and/or CXCL13 metabolism and activity. That can be manifest in abnormal B cell levels or B cell activity. Also included are known compounds with a pharmacologic effect in treating a disorder and so on that is associated with aberrant CXCR5 and/or CXCL13 metabolism and activity.

In addition, the antibodies of the instant invention may be conjugated to various effector molecules such as heterologous polypeptides, drugs, radionucleotides or toxins, see, e.g., WO 92/08495; WO 91/14438; WO 89/12624; U.S. Pat. No. 5,314,995; and EPO 396,387. An antibody or fragment thereof may be conjugated to a therapeutic moiety such as a cytotoxin (e.g., a cytostatic or cytocidal agent), a therapeutic agent or a radioactive metal ion (e.g., a emitters such as, for example, $^{213}$Bi). A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicine, doxorubicin, daunorubicin, dihydroxy anthracindione, mitoxantrone, mithramycin, actinomycin D, 1-dehydrotestosterone, glucocorticoids, procaine, tetracaine, lidocaine, propranolol and puromycin and analogs or homologues thereof. Therapeutic agents include, but are not limited to, antimetabolites (e.g., methotrexate, 6-mercaptopurine, 6-thioguanine, cytarabine, 5-fluorouracil and decarbazine), alkylating agents (e.g., mechlorethamine, chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin, daunomycin and doxorubicin), antibiotics (e.g., dactinomycin, actinomycin, bleomycin, mithramycin and anthramycin (AMC)), and anti-mitotic agents (e.g., vincristine and vinblastine).

Techniques for conjugating such a therapeutic moiety to antibodies are well known, see, e.g., Anion et al., in Monoclonal Antibodies and Cancer Therapy, Reisfeld et al. (eds.), p. 243-56 Alan R. Liss (1985); Hellstrom et al., in Controlled Drug Delivery, 2nd ed., Robinson et al., eds., p. 623-53, Marcel Dekker (1987); Thorpe, in Monoclonal Antibodies '84: Biological And Clinical Applications, Pinchera et al., eds., p. 475-506 (1985); Monoclonal Antibodies For Cancer Detection and Therapy, Baldwin et al., eds., p. 303-16, Academic Press (1985); and Thorpe, et al., Immunol Rev 62:119 (1982). Alternatively, an antibody can be conjugated to a second antibody to form an antibody heteroconjugate, such as a bifunctional antibody, see, e.g., U.S. Pat. No. 4,676,980.

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator, an apoptotic agent, e.g., TNF-α, TNF-β, AIM I (WO 97/33899), AIM II (WO 97/34911), Fas ligand (Takahashi et al., Int Immunol, 6:1567 (1994)), VEGF (WO 99/23105); a thrombotic agent; an anti-angiogenic agent, e.g., angiostatin or endostatin; or biological response modifiers such as, for example, lymphokines, interleukin-1 (IL-1), interleukin-2 (IL-2), interleukin-6 (IL-6), granulocyte macrophage colony stimulating factor (GM-CSF), granulocyte colony stimulating factor (GCSF) or other growth factors.

The formulations to be used for in vivo administration must be sterile. That can be accomplished, for example, by filtration through sterile filtration membranes. For example, the liquid formulations of the present invention may be sterilized by filtration using a 0.2 µm or a 0.22 µm filter.

Sustained-release preparations may be prepared. Suitable examples of sustained-release preparations include semi-permeable matrices of solid hydrophobic polymers containing the antibody, which matrices are in the form of shaped articles, e.g., films or matrices. Examples of sustained-release matrices include polyesters, hydrogels (for example, poly(2-hydroxyethylmethacrylate), poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers (such as injectable microspheres composed of lactic acid-glycolic acid copolymer) and poly-D-(−)-3-hydroxybutyric acid. While polymers such as ethylene-vinyl acetate and lactic acid-glycolic acid enable release of molecules for over 100 days, certain hydrogels release proteins for shorter time periods. Rational strategies can be devised for stabilization depending on the mechanism involved. For example, if the aggregation mechanism is discovered to be intermolecular S-S bond formation through thio-disulfide interchange, stabilization may be achieved by modifying sulthydryl residues, lyophilizing from acidic solutions, controlling moisture content, using appropriate additives, amino acid substitution and developing specific polymer matrix compositions.

The antibody, or variant thereof, composition will be formulated, dosed and administered in a manner consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody or variant to be administered will be governed by such considerations, and can be the minimum amount necessary to prevent, ameliorate or treat a CXCR5 disease, condition or disorder.

The antibody, or variant thereof, optionally is formulated with one or more agents currently used to prevent or treat the disorder in question. The effective amount of such other agents depends on the amount of antibody present in the formulation, the type of disorder or treatment and other factors discussed above. These are generally used in the same dosages and with administration routes as used hereinbefore or about from 1 to 99% of the heretofore employed dosages.

As used herein, the term "effective amount" refers to the amount of a therapy (e.g., a prophylactic or therapeutic agent), which is sufficient to reduce the severity and/or duration of a CXCR5 disease, ameliorate one or more symptoms thereof, prevent the advancement of a CXCR5 disease or cause regression of a CXCR5 disease, or which is sufficient to result in the prevention of the development, recurrence, onset, or progression of a CXCR5 disease or one or more symptoms thereof, or enhance or improve the prophylactic and/or therapeutic effect(s) of another therapy (e.g., another therapeutic agent) useful for treating a CXCR5 disease. For example, a treatment of interest can reduce elevated B cell levels, based on baseline or a normal level, by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. In another embodiment, an effective amount of a therapeutic or a prophylactic agent reduces the symptoms of a CXCR5 disease, such as arthritis or graft rejection by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. Also used herein as an equivalent is the term, "therapeutically effective amount."

The amount of therapeutic polypeptide, antibody or fragment thereof which will be effective in the use or treatment of a particular disorder or condition will depend on the nature of the disorder or condition, and can be determined by standard clinical techniques. Where possible, a dose-response curve and the pharmaceutical compositions of the invention can be first derived in vitro. If a suitable animal model system is available, again a dose-response curve can be obtained and used to extrapolate a suitable human dose practicing methods known in the art. However, based on common knowledge of the art, a pharmaceutical composition effective in promoting a diminution of an inflammatory effect, for example, may provide a local therapeutic agent concentration of between about 5 and 20 ng/ml, and, preferably, between about 10 and 20 ng/ml. In an additional specific embodiment of the invention, a pharmaceutical composition effective in ameliorating the growth and survival of cells responsible for B cell-dependent autoimmune manifestations or graft rejection may provide a local therapeutic agent concentration of between about 10 ng/ml and about 100 ng/ml.

In a preferred embodiment, an aqueous solution of therapeutic polypeptide, antibody or fragment thereof can be administered by subcutaneous injection. Each dose may range from about 0.5 mg to about 50 mg per kilogram of body weight, or more preferably, from about 3 mg to about 30 mg per kilogram body weight. The dosage can be ascertained empirically for the particular disease, patient population, mode of administration and so on, practicing pharmaceutics methods known in the art.

The dosing schedule for subcutaneous administration may vary from once a week to daily depending on a number of clinical factors, including the type of disease, severity of disease and the sensitivity of the subject to the therapeutic agent.

The instant invention provides methods for preparing liquid formulations of the antibody or CXCR5-binding fragment thereof, said methods comprising concentrating a fraction of purified antibody to a final concentration of about 15 mg/ml, about 20 mg/ml, about 30 mg/ml, about 40 mg/ml, about 50 mg/ml, about 60 mg/ml, about 70 mg/ml, about 80 mg/ml, about 90 mg/ml, about 100 mg/ml, about 200 mg/ml, about 250 mg/ml, about 300 mg/ml or more using, for example, a semi-permeable membrane with an appropriate molecular weight (mw) cutoff (e.g., 30 $K_D$ cutoff for $F_{(ab')2}$ fragments thereof; and 10 $K_D$ cutoff for $F_{ab}$ fragments) and, optionally, diafiltering the concentrated antibody fraction into the formulation buffer using the same membrane.

In addition, the present invention also encompasses stable, such as $K_D$ stable, liquid formulations of the products of interest that have improved half-life in vivo. Thus, the antibody of interest has a half-life in a subject, preferably a human, of greater than 3 days, greater than 7 days, greater than 10 days, greater than 15 days, greater than 25 days, greater than 30 days, greater than 35 days, greater than 40 days, greater than 45 days, greater than 2 months, greater than 3 months, greater than 4 months, greater than 5 months or more.

To prolong the serum circulation of an antibody in vivo, various techniques can be used. For example, inert polymer molecules, such as high molecular weight polyethylene glycol (PEG), can be attached to an antibody with or without a multifunctional linker either through site-specific conjugation of the PEG to the N-terminus or to the C-terminus of the antibody or via ε amino groups present on lysine residues. Linear or branched polymer derivatization that results in minimal loss of biological activity can be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or by ion exchange chromatography. PEG-derivatized antibodies can be tested for binding activity as well as for in vivo efficacy using methods known to those of skilled in the art, for example, by immunoassays described herein.

An antibody having an increased half-life in vivo can also be generated by introducing one or more amino acid modifications (i.e., substitutions, insertions or deletions) into an IgG constant domain, or $F_cR$ binding fragment thereof (such as an $F_e$ or hinge $F_e$ domain fragment), see, e.g., WO 98/23289; WO 97/34631; and U.S. Pat. No. 6,277,375.

Further, an antibody can be conjugated to albumin to make an antibody more stable in vivo or have a longer half life in vivo. The techniques are known in the art, see e.g., WO 93/15199, WO 93/15200 and WO 01/77137; and EPO 413, 622. The antibody also can be modified, for example, by glycosylation, acetylation, phosphorylation, amidation, derivatization by known protecting/blocking groups, proteolytic cleavage, linkage to a cellular ligand or other protein and so on.

In one embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine or other "caine" anesthetic to ease pain at the site of the injection. Generally, the ingredients are supplied either separately or mixed together in unit dosage form, for example, as a dry lyophilized powder or water-free concentrate in a sealed container, such as an ampule or sachet indicating the quantity of active agent. Where the composition is to be administered by infusion, it can be dispensed with an infusion bottle containing sterile pharmaceutical grade water or saline. Where the composition is administered by injection, an ampule of sterile water for injection or saline can be provided, for example, in a kit, so that the ingredients may be mixed prior to administration.

The invention also provides that a liquid formulation of the present invention is packaged in a sealed container such as an ampule or sachet indicating the quantity of the product of interest. The liquid formulations of the instant invention can be in a sealed container indicating the quantity and concentration of the antibody or antibody fragment. The liquid formulation of the instant invention can be supplied in a sealed container with at least 15 mg/ml, 20 mg/ml, 30 mg/ml, 40 mg/ml, 50 mg/ml, 60 mg/ml, 70 mg/ml, 80 mg/ml, 90 mg/ml, 100 mg/ml, 150 mg/ml, 200 mg/ml, 250 mg/ml, or 300 mg/ml of CXCR5 antibody in a quantity of 1 ml, 2 ml, 3 ml, 4 ml, 5 ml, 6 ml, 7 ml, 8 ml, 9 ml, 10 ml, 15 ml or 20 ml, for example.

An article of manufacture containing materials useful for the treatment of the disorders described above is provided.

The article of manufacture comprises a container and a label. Suitable containers include, for example, bottles, vials, syringes and test tubes. The containers may be formed from a variety of materials such as glass or plastic. The container holds a composition which is effective for diagnosing, preventing or treating a CXCR5 condition or disease and may have a sterile access port (for example, the container may be an intravenous solution bag or a vial having a stopper pierceable by a hypodermic injection needle). The label on or associated with the container indicates that the composition is used for treating the condition of choice. The article of manufacture may further comprise a second container comprising a pharmaceutically acceptable buffer, such as phosphate-buffered saline, Ringer's solution and dextrose solution. It may further include other materials desirable from a commercial and user standpoint, including buffers, diluents, filters, needles, syringes and package inserts with instructions for use.

In another aspect of the invention, nucleic acids comprising sequences encoding antibodies or functional derivatives thereof, are administered to treat, inhibit or prevent a disease or disorder associated with aberrant expression and/or activity of CXCR5, by way of gene therapy. Gene therapy refers to therapy performed by the administration to a subject of an expressed or expressible nucleic acid of interest. In the embodiment of the invention, the nucleic acids produce the encoded protein in and by target host cells that mediate a therapeutic effect. Any of the methods for gene therapy available can be used according to the instant invention.

For general reviews of the methods of gene therapy, see Goldspiel et al., Clinical Pharmacy 12:488 (1993); Wu et al., Biotherapy 3:87 (1991); Tolstoshev, Ann Rev Pharmacol Toxicol 32:573 (1993); Mulligan, Science 260:926 (1993); Morgan et al., Ann Rev Biochem 62:191 (1993); and May, TIBTECH 11:155 (1993).

In one aspect, the compound comprises nucleic acid sequences encoding an antibody, or functional binding fragments thereof, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific, as well as other regulatory sequences.

In another particular embodiment, nucleic acid molecules are used in which the antibody coding sequences and any other desired sequences are flanked by regions that promote homologous recombination at a desired site in the genome, thus providing for intrachromosomal expression of the antibody-encoding nucleic acids (Koller, et al., Proc Natl Acad Sci USA 86:8932 (1989); Zijlstra et al., Nature 342:435 (1989)). In specific embodiments, the expressed antibody molecule is a single chain antibody; alternatively, the nucleic acid sequences include sequences encoding both the heavy and light chains, or fragments thereof, of the antibody. Alternative methods for integration include using particular transcription factors that recognize specific nucleic acid sequences, zinc fingers and so on.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient.

In one embodiment, the nucleic acid sequences are directly administered in vivo and is expressed to produce the encoded product. That can be accomplished by any of numerous methods known in the art, e.g., by constructing the antibody encoding sequences as part of an appropriate nucleic acid expression vector and administering same so that the vectors become intracellular, e.g., by infection using defective or attenuated retrovirals or other viral vectors (see U.S. Pat. No. 4,980,286), by direct injection of naked DNA, by use of microparticle bombardment (e.g., a gene gun; Biolistic, Dupont), using non-viral vectors, such as synthetic compositions comprising an amphipathic compound that binds the hydrophilic nucleic acid and has the ability to fuse with cells, generally thus containing a hydrophobic portion for combining with membranes, coating with lipids or cell-surface receptors or transfecting agents, encapsulation in liposomes, microparticles, or microcapsules, by administering the vector in linkage to a peptide which is known to enter the nucleus, by administering the vector in linkage to a ligand subject to receptor-mediated endocytosis (see, e.g., Wu et al., J Biol Chem 262:4429 (1987)) (which can be used to target cell types specifically expressing the receptors) etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell-specific uptake and expression, by targeting a specific receptor (see, e.g., WO 92/06180; WO 92/22635; WO92/20316; WO93/14188 and WO 93/20221).

Regarding vectors, for example, a lentiviral vector can be used as known in the art. The lentiviral vectors contain components for packaging the viral genome and integration into the host cell DNA. The nucleic acid sequences encoding the antibody to be used in gene therapy are cloned into one or more vectors, which facilitate the delivery of the gene into a patient. For example, a lentiviral vector can be used to deliver a transgene to hematopoietic stem cells. References illustrating the use of retroviral vectors in gene therapy are: Clowes et al., J Clin Invest 93:644 (1994); Kiem et al., Blood 83:1467 (1994); Salmons et al., Human Gene Therapy 4:129 (1993); and Grossman et al., Curr Opin Gen and Dev 3:110 (1993).

Adenoviruses also may be used in the instant invention. Targets for adenovirus-based delivery systems are liver, the central nervous system, endothelial cells and muscle, for example. Adenoviruses infect non-dividing cells, an advantage over early retroviral vectors. Kozarsky et al., Curr Opin Gen Dev 3:499 (1993) present a review of adenovirus-based gene therapy. Bout et al., Human Gene Therapy 5:3 (1994) demonstrated the use of adenovirus vectors to transfer genes to the respiratory epithelia of rhesus monkeys. Other instances of the use of adenoviruses in gene therapy can be found in Rosenfeld et al., Science 252:431 (1991); Rosenfeld et al., Cell 68:143 (1992); Mastrangeli et al., J Clin Invest 91:225 (1993); WO94/12649; and Wang et al., Gene Therapy 2:775 (1995).

Adeno-associated virus (AAV) also can be used in gene therapy (Walsh et al., Proc Soc Exp Biol Med 204:289 (1993); and U.S. Pat. Nos. 5,436,146; 6,632,670; and 6,642,051).

Another approach to gene therapy involves transferring a gene to cells in tissue culture by such methods as electroporation, lipofection, calcium phosphate-mediated transfection or viral infection. Usually, the method of transfer includes the transfer of a selectable marker to the cells. The cells then are placed under selection to isolate those cells that have taken up and are expressing the transferred gene. Those cells then are delivered to a patient.

Thus, the nucleic acid can be introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion etc. Numerous techniques are known in the art for the introduction of foreign genes into cells (see, e.g., Loeffler et al., Meth Enzymol 217:599 (1993); Cohen et al., Meth Enzymol 217:618 (1993); and Cline Pharm Ther 29:69 (1985)) and may be used in accordance with the present invention, provided that the necessary developmental and physiological functions of the recipient cells are not disrupted. The technique should provide for the stable transfer of the nucleic acid to the cell, so that the nucleic acid is expressed by the cell, heritable and expressed by the cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state etc., and can be determined by one skilled in the art.

Cells into which a nucleic acid can be introduced for purposes of gene therapy encompass any desired, available cell type, and include, but are not limited to, epithelial cells, endothelial cells, keratinocytes, fibroblasts, muscle cells, hepatocytes, blood cells, such as T lymphocytes, B lymphocytes, monocytes, macrophages, neutrophils, eosinophils, megakaryocytes and granulocytes; various stem or progenitor cells, in particular hematopoietic stem or progenitor cells, e.g., as obtained from bone marrow, umbilical cord blood, peripheral blood, fetal liver etc.

In one embodiment, the cell used for gene therapy is autologous to the patient. Nucleic acid sequences encoding an antibody of the instant invention are introduced into the cells such that the transgene is expressed by the cells or their progeny, and the recombinant cells then are administered in vivo for therapeutic effect. In a specific embodiment, stem or progenitor cells are used. Any stem and/or progenitor cells which can be isolated and maintained in vitro can potentially be used in accordance with the embodiment of the instant invention (see e.g., WO 94/08598; Stemple et al., Cell 71:973 (1992); Rheinwald Meth Cell Bio 21A:229 (1980); and Pittelkow et al., Mayo Clinic Proc 61:771 (1986)). Because CXCR5 is expressed on, for example, B cells, blood cells and bone marrow cells are suitable host cells. However, the scope of the instant invention regarding the use of stem cell hosts does not contemplate the making and using of a transgene to make a transgenic organism by administering the transgene of interest to embryos and embryonic stem cells.

The invention provides methods of treatment, prophylaxis and amelioration of CXCR5 diseases or one or more symptoms thereof by administrating to a subject of an effective amount of, for example, a liquid formulation of the invention. The subject is preferably a mammal such as non-primate (e.g., cows, pigs, horses, cats, dogs, rats etc.) and a primate (e.g., monkey, such as a cynomolgus monkey, and a human). In a preferred embodiment, the subject is a human.

CXCR5 also is expressed on certain cancer cells, such as pancreas, colon and bladder, as well as on T cell leukemias (Qinping et al., Oncogene 24:573-584, 2005), and B cell leukemias (Burkel et al., Blood, July 2007; doi:10.1182/blood-2007-05-089409) and stimulation of CXCR5 correlated with proliferation of carcinoma cells, Meijer et al., Canc Res 66:9576-9582, 2006.

Thus, the antibody or derivative thereof of interest can be used to control proliferation of cancer cells expressing CXCR5, which cancers are identified by determining presence of CXCR5 expression by a diagnostic assay taught herein. The antibody of interest can reduce infiltration of malignant cells, reduce resistance to apoptosis and minimize proliferation. Such patients then are administered a cancer cell proliferation inhibiting amount of an antibody, or derivative thereof, of interest as provided herein.

Autoimmune disorders are associated with aberrant and/or high expression of CXCL13, such as lupus (Ishikawa et al., J Exp Med 193:1393-1402, 2001) and Sjoren's Syndrome (Salomonsson et al., Scan J Imm 55:336-342, 2002; and Barone et al., Arth Rheum 52(6)1773-1784, 2005), or high expression of CXCR5, such as in myasthenia gravis (Sims et al., J Imm 167:1935-1944, 2001; Saito et al., J Neuroimm 55:336-342, 2005; and Tackenberg et al., Eur J Imm 37:849-863, 2007). Hence, an antibody of interest is used to minimize the effect of high levels or high activity of CXCL13 or CXCR5 ligand. In autoimmune disorders characterized by high levels of B cells, high levels of CXCR5 or high levels of CXCL13, or other CXCR5 ligand, a B cell activity inhibiting amount of an antibody of interest is administered as taught herein.

Aberrant CXCR5 expression is observed in multiple sclerosis, Brain 129(Pt 1)200-211, 2006.

In colitis, CXCR5 has a role in GALT formation and function (Carlsen et al., Gut, 2002, 51(3)364-367). CXCR5-mediated migration and infiltration of B cells into the gut lamina propria, and mucosal infiltration in general, (Mazzucchelli et al., J Clin Invest, 1999, 104(10)R49-R54) and expression thereof in ulcerative colitis lesions which contain ectopic germinal centers, is inhibited by an antibody of interest.

B cell depletion can be of therapeutic benefit in ameliorating symptoms under certain circumstances and in certain indications, such as, in rheumatoid arthritis (Oligino & Dalrymple, Arth Res Ther 5(Suppl 4)S7-S11, 2003). CXCR5 is expressed at high levels in the synovial tissue of arthritis patients, as compared to tissue from individuals not afflicted with rheumatoid arthritis (Schmutz et al., Arth Res Ther 7:R217-R229, 2005). Thus, certain forms of the instant antibody, and derivatives thereof, can deplete B cell populations, and can prevent infiltration and interaction of B cells in a joint. Accordingly, a treatment can include administering a B cell level reducing amount of an antibody of interest to a patient diagnosed with arthritis. The antibody can be administered locally to the affected joint.

Ectopic lymphoid neogenesis is observed in several conditions, including psoriatic arthritis (Canete et al., Ann Rheum Dis, Jan. 12, 2007, doi:10:1136/ard.2006.062042), chronic inflammatory diseases, in general (Aloisi & Pujol-Borrell, Nat Rev Imm 6:205-217, 2006) and in grafts undergoing rejection, both chronic (Baddoura et al., Am J Trans 5:510-516, 2005) and acute (DiCarlo et al., Am J Trans 7:201-210, 2007). CXCL13 and CXCR5 were present in cardiac grafts (DiCarlo et al., supra); and CXCL13 was present in psoriatic arthritis (Canete et al., supra). Presence of CXCL13 and/or CXCR5 is associated with the development of the ectopic lymphoid follicles with B cell and T cell areas, as found in normal nodes. B cell antigen presentation of alloantigen also was associated with acute cardiac allograft model (Noorchashm et al., J Imm 177:7715-7722, 2006).

Thus, an antibody of interest can be used to dampen inflammation and graft rejection. A patient then is administered a B cell activity inhibiting amount of an antibody to dampen inflammation, to minimize ectopic germinal center development, to minimize B cell recruitment to a graft and to minimize B cell alloantigen presentation before or following a transplantation procedure.

The invention now will be exemplified for the benefit of the artisan by the following non-limiting examples that depict some of the embodiments by and in which the instant invention can be practiced.

EXAMPLES

Example 1

Generation of Immunogen

Anti-CXCR5 monoclonal antibodies can be raised to CHO cells transformed with DNA encoding full-length human CXCR5 and expressed on the cell surface ("r-CXCR5-CHO cells"). The CXCR5 sequence used to transform the cells can be obtained from data bases, such as NM 001716.2, NC000011.8 or NM001716, and synthesized or isolated from a suitable cell source.

The CXCR5 open reading frame was placed into an expression vector, such as pcDNA3.1neo_DEST, and then transfected into 300-19 cells (Immunogen).

Also, the CXCR5 EC domain, with the amino acid sequence, MNYPTLEMDLENLEDLFWELDRLD-NYNTSLVENHLC (SEQ ID NO:1), was conjugated to KLH by the C terminal cysteine, and was used as immunogen. Cells expressing CXCR5 or the CXCR5 EC domain were administered IP ($5\times10^6$ cells in 0.2 ml or 50 μg peptide in 100 μl of buffer, optionally mixed with 100 μl of adjuvant, such as Freund's complete adjuvant). Injections with the antigen were repeated every two weeks until high titer CXCR5 antibody was detected in the serum using any of a variety of known methods, for example, by ELISA or FACS using, for example, CXCR5+ cells, which can be isolated, for example by FACS, and, for example, the commercially available MAB 190 (R & D Systems) as a positive control.

The cells expressing CXCR5 were maintained at 37° C. under 5% $CO_2$ in RPMI (Invitrogen, Carlsbad, Calif.) supplemented with 10% dialyzed fetal bovine serum (FBS) (Invitrogen). Cells were prepared for injection by substituting the above culture medium with phosphate-buffered (Ca/Mg-free) saline (CMF-PBS) supplemented with 5 mM EDTA, and harvesting the cells in that buffer. The harvested cells were pelleted by centrifugation at 500×g for about 5 minutes, washed once by resuspending the pellet in CMF-PBS and centrifuging as before, counted, and adjusted to the appropriate volume (such as $5\times10^6$ cells in 0.2 ml) for injection by resuspending the cell pellet in CMF-PBS.

As mentioned, CXCR5 expression was monitored, for example, by FACS analysis, using commercially available CXCR5 antibodies, such as MAB190 (R & D), clone RF8B2 and 2G8 (2G8 is an rat anti-mouse CXCR5 antibody, while the other purchased antibodies are anti-human CXCR5 antibodies) (BD), and 2C1 (Abnova), as well as various polyclonal antibodies directed to hCXCR5 made practicing methods known in the art.

To facilitate the plasmid construction and to enhance the expression of CXCR5, oligonucleotides corresponding to the leader peptide sequence comprising the first 135 base pairs of the CXCR5 nucleic acid coding sequence were generated. The oligonucleotides contained some changes in the wobble coding positions to lower the GC content. All nucleotide sequence changes were silent, i.e., no amino acid sequence changes resulted. After annealing the oligonucleotides together, the engineered leader peptide coding sequence was linked to the rest of the coding sequence by PCR-SOE (Ho et al., Gene 77:51 (1989); and Horton et al., BioTechniques 8:528 (1990)).

Expression of CXCR5 was verified prior to use as immunogen. Cells are cultured in RPMI (Invitrogen, Carlsbad, Calif.) containing 10% FBS, 0.2 mM of glutamine and 1× non-essential amino acid solution followed by seeding about $3-5\times10^5$ cells per well in a T75 flask and grown for approximately 24-48 hours.

The transformed or transfected cells were cultured for about two weeks until the cells not carrying CXCR5 expression plasmid were eliminated by antibiotic selection. Cells of the stable cell lines can be lysed, proteins obtained and subjected to Western blot analysis.

Stable or transient transfected cells were assayed for expression of CXCR5 using methods for detecting cell surface expression of CXCR5, such as by FACS analysis. Alternatively, cells can be lysed and the proteins studies, for example, by Western blot analysis. Transfected cells harvested from culture dishes were washed once with phosphate-buffered saline (PBS) and resuspended in deionized water, mixed with an equal volume of 2× protein sample loading buffer (BioRad, Hercules, Calif.) and then heated at about 100° C. for 10 minutes. Membrane protein was analyzed using conditioned medium mixed with an equal volume of 2× protein sample loading buffer and heated at 100° C. for 10 minutes. The samples were separated using 4-12% gradient SDS-PAGE. The proteins were transferred from the gel to a nitrocellulose membrane (BioRad, Hercules, Calif.), which was blocked with 5% nonfat dry milk in PBST (PBS with 0.05% TWEEN-20®) for at least one hour prior to transfer of protein.

CXCR5 was detected by incubating the membrane with CXCR5-specific primary antibody in blocking buffer for at least an hour at room temperature, with shaking. The membrane was washed at least three times and a reporter-conjugated secondary antibody in blocking buffer was added to the membrane and incubated for at least one hour at room temperature, with shaking. The membrane was washed three times in PBST and developed with, for example, a chemiluminescent substrate.

Example 2

Generation of Anti-CXCR5 Mabs

A/J or BALB/cJ mice, about 4-6 weeks old (Jackson Labs, Bar Harbor, Me.) were immunized with the CXCR5-transfected cells or an EC peptide. A group of mice were primed intraperitoneally on day 0 with a 1:1 emulsion of KLH-conjugated peptide mixed with adjuvant (CFA), boosted ip on day 20 with the peptides with IFC (incomplete Freund's adjuvant) and/or cells in PBS without adjuvant, and finally boosted intravenously on day 44 with the KLH-peptides mixed in IFC and/or cells in PBS, without adjuvant. Another group of mice were primed ip on day 0, boosted ip on days 15, 39, 53 and 67, and finally boosted intravenously on day 81 (all injections with cells in PBS, without adjuvant). For both groups of mice, each injection contained approximately $3\times10^6$ to $2\times10^7$ cells in a volume of approximately 200 μl. Alternatively, peptide and/or cell immunizations were performed once every two weeks, 3-6 times until a desirable anti-CXCR5 titer was obtained, as ascertained, for example, by FACS analysis or ELISA.

Three days after the last injection, the mice, optionally were tested for anti-CXCR5 antibody titer in serum, were sacrificed and the spleen was removed and placed in approximately 10 ml of serum-free DMEM (Gibco) in a Petri dish. The splenocytes were teased out of the capsule using forceps and washed twice in 10 ml of serum-free IMDM (Cellgro, Herndon, Va.) at 37° C. The spleen cell suspensions were transferred to a 15 ml conical bottom tube and debris allowed to settle for about 2-5 minutes. The supernatant containing the splenocytes was transferred to a fresh 15 ml conical bottom tube and washed three more times with IMDM until the fusion. The spleen cells from mice can be pooled.

Optionally, a 5 ml single cell suspension of control spleen feeder cells was prepared from an unimmunized mouse essentially as described above for the immunized spleen cells and placed in an incubator (37° C., 5% $CO_2$) until needed.

The fusion partner for the immunized spleen cells can be a hypoxanthine/aminopterin/thymidine (HAT)-sensitive, non-secreting myeloma cell line, such as P3×63-AG8.653 or SP2/0 (ATCC, Manassas, Va.) or FO_B lymphoblasts (ATCC, CRL-1646)). Prior to the fusions, the lymphoid cells were maintained in IMDM/10% FBS (37° C., 7% $CO_2$) ensuring that the cells are in logarithmic growth phase on the day of the fusion. An alternative selection mechanism relies on using azaserine, which typically is added one day after fusion.

The fusion protocol used is a hybrid of the protocols set forth in Lerner (Yale J Biol Med, 1981, 54(5)387-402) and Gefter et al. (Somatic Cell Genet, 1977, 3(2)231-236). Before the fusion, the pooled spleen cells were washed three times with serum-free IMDM, and counted. Also, immediately before fusion, the logarithmic phase mycloma cells were washed three times with serum-free IMDM and counted. The lymphoid cells were resuspended to $1 \times 10^7$ cells/ml in serum-free IMDM. For each fusion, $1-1.5 \times 10^8$ spleen cells were mixed with $1-3 \times 10^7$ myeloma cells in a 50 ml conical bottom polypropylene tube, and the cells were washed once with serum-free IMDM. The ratio of spleen cells to myeloma cells was 5:1. The tubes were centrifuged at 500×g for 10 minutes to pellet the cells. After aspiration of the supernatants, the pellets were resuspended gently by tapping the bottom of the tubes. The tubes then were placed in a beaker of 37° C. water. All subsequent fusion steps were carried out in that beaker.

Next, 1 ml of polyethylene glycol 1500 (Roche Applied Science, Indianapolis, Ind.) preheated to 37° C. was added slowly to each cell pellet over the course of about 1 minute, while gently rocking the tube. The cells were incubated in the PEG for about one minute followed by addition of one ml serum-free IMDM added dropwise to each pellet over the course of 30 seconds, and then 9 ml serum-free IMDM were added to each pellet over the next minute. Both tubes were centrifuged at 500×g for 10 minutes at room temperature, and the supernatants were aspirated. The cell pellet was resuspended in 100 ml of filtered complete hybridoma production media (500 ml IMDM (Cellgro) mixed with 10% FBS (Sera-Care, Millford, Mass.), 0.2 mM of L-glutamine, 1× non-essential amino acid solution, 1 mM sodium pyruvate, 0.01% pen-strep (Invitrogen) and 1× HT supplement (Invitrogen)).

Each 100 ml cell suspension was plated in ten 96-well flat-bottom microtiter plates, with a volume of ~100 µl/well. The plates were kept in an incubator at 37° C., 7% $CO_2$. On day 2 post-fusion, the cells were selected by addition of 5.7 µM azaserine in IMDM to the fused cells at 100 µl per well. Supernatants were withdrawn for primary screening, typically on days 10-14 post-fusion, from wells containing clones. The fusion efficiency was 75-99% (720-950 out of 960 possible wells developed clones that were screened).

The primary screen can be a radioimmunoassay (RIA) designed to detect antibodies that bind to human CXCR5. To perform the RIA, affinity-purified goat anti-mouse IgG ($F_c$ fragment-specific) (Cappell, Cochranville, Pa.) in PBS is added to 96-well PVC microtiter plates (50 µl/well) and incubated overnight at 4° C. The goat anti-mouse IgG is removed from the plates and the wells are blocked with 100 µl/well of 5% FCS/PBS for 1 hour at room temperature. After removing the blocking solution, neat hybridoma culture supernatant is added to the wells (50 µl/well) and incubated 1 hour at room temperature. The plates are washed 3 times with PBS/0.05% Tween-20. Next, 50 µl $^{125}$I-CXCR5 (~20,000 cpm) in PBS/ 5% FCS are added to each well, and incubated 1 hour at room temperature. Finally, the wells are washed 3 times with PBS/ 0.05% Tween-20. After flicking out all the wash buffer, the wells are separated by cutting the plates and analyzed in a gamma counter. Wells to which 5% FCS/PBS is added instead of culture supernatant served as background wells.

The purified CXCR5 is labeled with $^{125}$I according to the Bolton-Hunter method, substantially as described by the supplier of the Bolton-Hunter reagent (New England Nuclear, Boston, Mass.). The quality of the $^{125}$I-CXCR5 is monitored by confirming that the labeling procedure did not destroy the epitopes recognized by commercially available CXCR5 antibodies (R & D or Becton Dickinson, Mountain View, Calif.).

Clones are considered to be positive on primary screening if supernatant samples are labeled approximately 10-fold over background in the RIA. Positive clones are pulled, expanded and stored frozen.

A primary hybridoma screen was designed to determine whether the antibodies recognized native CXCR5 epitopes. That was accomplished by FACS analysis of cell surface CXCR5 displayed on CXCR5$^+$ cells stained with the monoclonal antibodies, visualizing binding with fluorescently labeled goat anti-mouse second antibody. Clones were considered to be positive on primary screening if supernatant samples were labeled approximately 10-fold over background in the FACS analysis. Also, to localize the CXCR5 epitopes bound by antibodies, competition assays with CXCR5 antibodies were conducted. Positive clones were selected, expanded and stored frozen.

Example 3

Cell-Based Binding Assays for Anti-CXCR5 mABS

A cell-based binding assay was used to characterize the anti-CXCR5 mAbs. For example, the CXCR5-expressing transfected cells described above, such as hCXCR5/ HEK293, can be used. A full-length human CXCR5 open reading frame was cloned into a vector, for example, pcDNA3.1neo DEST (Invitrogen, Carlsbad, Calif.). The CXCR5-coding region was synthesized by RT-PCR using human brain and liver RNA (Ambion, Inc., Austin, Tex.) as a template. The final plasmid construct, CXCR5/cDNA3.1neo, expressed a full-length CXCR5 protein. A stable cell line expressing CXCR5 was generated by transfection of CXCR5/pcDNA3.1neo plasmid construct into CHO or HEK293 cells (ATCC No. CRL-1573) using a standard and commercially available Lipofectamine 2000 kit. After transfection, the cells were cultured in DMEM overnight, then reseeded in medium with 200 µg/ml neomycin and cultured for 12-14 days. Isolated single colonies were picked and grown in separate wells until enough clonal cells were amplified. Stable clones resistant to neomycin and which expressed high levels of CXCR5 protein were identified by FACS analysis using polyclonal anti-CXCR5 antibodies (R&D Systems, Minneapolis, Minn.) or custom generated polyclonal antibodies.

Human HS Sultan cells (ATCC No. CRL-1484) naturally expressing CXCR5 were also confirmed for CXCR5 expression by FACS analysis. HS Sultan cells were grown in RPMI 1640 containing 10% fetal calf serum, 0.2 mM of glutamine and 0.1% pen/strep solution (100 μg/ml penicillin and 10 μg/ml streptomycin).

Cell-based antibody-binding can be assessed using the FMAT™ (fluorescence macro-confocal high-throughput screening) 8100 HTS or 8200 Cellular Detection System (Applied Biosystems, Foster City, Calif.) following the protocol provided by the manufacturer. Cell lines naturally expressing CXCR5 or stably transfected with CXCR5 expression constructs are seeded in 96-well plates. Alternatively, transiently transfected 293T or CHO cells are seeded in the 96-well plate. The cells are seeded at a density of 5,000-30,000 cells per well. After 20-24 hours, anti-CXCR5 mAbs and FMAT-conjugated goat anti-mouse IgG antibody are added together to the wells and incubated for 1 h, 2 h, 4 hr or overnight at room temperature.

Cell-based antibody-binding was also assessed by FACS using a HEK293/CXCR5 stable cell line expressing CXCR5. Cells were incubated with anti-CXCR5 mAbs in PBS. After three washes, the cells were incubated with fluorescent molecule-conjugated secondary antibody (BD Sciences, Palo Alto, Calif.).

The results indicated that several mAbs bind to CXCR5 expressed from either recombinant plasmid constructs. For example, clones 11D6, 14C9, 19H5, H28, 54G6, G7, 56H6, 79B7 and 16D7, as well as humanized variants of the latter antibody, 16D7, 16D7-HC1-LC3, 16D7-HC1-LC2, 16D7-HC1-LC1 and 16D7-HC2-LC1, a negative control IL13 antibody, CA13, positive controls, MAB190, 2C1 and RF8B2, three mouse isotype controls to IgG1, IgG2a and IgG2b and a rat IgG2b isotype control (matched to RF8B2), were tested for binding to HEK293 cells transfected to express CXCR5. The 2C1 and MAB 190 positive control antibodies bind to the CXCR5 cells. RF8B2 presented with intermediate binding levels. The negative control antibodies exhibited only background binding. All antibodies except for CA13 bound to the hCXCR5/HEK293 cells with similar binding profiles and titration kinetics as the parent antibody 16D7 and with 79B7.

Transiently transfected HEK293 cells containing a CXCR5/neo plasmid are also stained with immunofluorescence as described above and observed by fluorescent microscopy. The cell-based FMAT and FACS analyses confirm that mAbs indeed bind to CXCR5 expressed either from recombinant plasmid constructs or as native protein in cultured cells. A positive binding signal is determined based on the FMAT signal read-out that is significantly higher than background binding and other negative hybridoma clones (p>0.01).

The CXCR5 mAbs generated, such as 16D7, 14C9, 19H5, H28, 54G6, G7, 56H6 and 79B7, bind to the EC domain and block binding of CXCL13 to CXCR5 on the cell.

Example 4

Biacore Affinity Analysis

The N-terminal EC region of CXCR5 (amino acids 1-59) from human and mouse were synthesized with a terminal biotin tag, and used in a forward format Biacore assay where the peptides were immobilized on a Biacore chip and then the kinetics of antibody interaction with the peptides on the chip were determined. The synthetic peptides were immobilized on a Biacore chip for approximately 20 response units (RUs'). Then the mAb's were exposed to the chip for kinetic measurements, following the manufacturer's recommendations (GE Healthcare, Piscataway, N.J.).

Mouse anti-hCXCR5 mAb clone, 16D7, had a calculated $K_D$ of $2.16^{-12}$ M; mouse/human IgG4 chimeric 16D7 (16D7 VH and VL regions grafted onto a human IgG4 Fc, the sequence of which is known in the art, optionally codon optimized, using standard methods, such as cloning, amplification of ends, ascertaining the mass of the regions and cloning the portions) had a $K_D$ of $1.41^{-12}$ M; and for various humanized variants of 16D7, wherein the structure of the variants and the derivation of the heavy and light chains thereof is denoted by the terms, "HC_" for a particular heavy chain and "LC_" for a particular light chain, which are grafted onto an IgG4 backbone, where the composition of the chains is provided hereinbelow, 16D7-HC1-LC1 had a $K_D$ of $3.11^{-12}$ M; 16D7-HC1-LC2 had a $K_D$ of $1.41^{-12}$ M; 16D7-HC2-LC1 had a $K_D$ of $2.40^{-12}$ M; 16D7-HC1-LC3 had a $K_D$ of $1.21^{-12}$ M; 16D7-HC3-LC4 had a $K_D$ of $4.92^{-12}$ M; 16D7-HC3-LC5 had a $K_D$ of $1.84^{-10}$ M; and 16D7-HC1-LC6 had a $K_D$ of $9.17^{-11}$ M.

Humanized SAR113244, a form of the 16D7 humanized variant, 16D7-HC1-LC3 that carries the S241P and L248E substitutions (substitutions introduced practicing known methods and reagents, using Kabat numbering), was captured on a Biacore chip by pre-immobilized mouse anti-human IgG Fc antibody, and then used in a reverse assay format Biacore assay where the kinetics of the un-tagged human CXCR5 N-terminal peptide (amino acids 1-59) interaction with the mAb's on the chip were determined. The $K_D$ for SAR113244 was determined to be $1.13 \pm 0.08^{-11}$ M. The $K_D$ values determined with the forward assay using biotinylated human peptide immobilized on the chip surface and SAR113244 as analyte, were consistent with those obtained using the reverse assay.

Example 5

Western Blot Analysis of Anti-CXCR5 mABS Binding Activity

Western blot was performed to assess the anti-CXCR5 mAb binding activity to CXCR5 under denaturing condition, as well as, expression levels of CXCR5 and other CXCR5-related protein in human cell lines. Protein samples also were prepared from stably transfected cells using M-PER mammalian protein extraction reagent kit (Pierce, Rockland, Ill., Cat #78501) following manufacturer's instructions, and heated at 70° C. for 10 minutes after adding an equal volume of 2× protein sample loading buffer. All samples were separated by electrophoresis in a 4-12% gradient SDS-PAGE gel. The proteins were transferred from the gel to a PVDF membrane and anti-CXCR5 mAbs were applied to the Western blot membrane as the primary detection antibody. An Alexa 680-conjugated secondary antibody was used for detection and the membranes were scanned using the Odyssey Infrared Imaging system (Li-cor, Lincoln, Nebr.) or using electro-chemiluminescence (ECL). Positive control antibodies against human CXCR5 were generated as taught herein.

Example 6

FACS Assay for Monitoring CXCR5 Internalization

Buffy coat cells are obtained from healthy volunteers (Gulf Coast Blood Center, Houston, Tex.). Human peripheral mononuclear cells (PBMCs) are isolated with a standard Ficoll-Hypaque gradient method. PBMCs are cultured (0.5× $10^6$ cells/well) in 96-well plate at 4° C. Each well contains 0.2 ml of RPMI 1640 supplemented with 10% FBS in the presence/absence of monoclonal antibodies (10 µg/ml). After 30 minutes, the medium is replaced with fresh, cold RPMI 1640 supplemented with 10% FBS and no antibodies. The cells are transferred to a 37° C. humidified tissue culture chamber containing 5% $CO_2$. Monoclonal antibody-treated cells are harvested immediately, 2 hr or 24 hr after transferring the cells to 37° C. Cells are washed once with PBS and incubated in cold PBS containing 1% BSA (PBSB) for 30 minutes. Cells then are stained with PE-conjugated anti-human CXCR5 (BD Biosciences). After 30 minutes, cells are washed 3 times with PBSB and fixed in 1% paraformaldehyde solution overnight. The next day, presence of CXCR5 is analyzed with a BD FACSCalibur™ system flow cytometer (BD Biosciences, San Jose, Calif.).

Example 7

FLIPR Assay

Changes in intracellular calcium were measured by plating 9000 cells/well and incubating overnight. The cells were the RBL-2H3 line stably transfected with human CXCR5. Cells then were washed and then loaded with 2 mM fluo-4/AM (Molecular Probes) in a buffer containing 2.5 mM probenicid. Cells were exposed to CXCR5 mAb then washed with assay buffer. The cells were exposed to 10 nM CXCL13 (R & D). Changes in intracellular $Ca^{+2}$ were recorded using the 384-B FLIPR device (Molecular Devices). Commercially available anti-human CXCR5 mAbs, and mouse IgG1 and IgG2b were used as controls.

As discussed herein below, several humanized versions of mAb 16D7 were constructed, such as chimeric 16D7 (the h$IgG_4$ chimera), 16D7-HC1-LC1, 16D7-HC1-LC2, 16D7-HC2-LC1, 16D7-HC1-LC3, 16D7-HC3-LC4, 16D7-HC3-LC5 and 16D7-HC1-LC6, and they were tested for biological activity as evidenced by calcium flux.

The humanized antibodies, aside from a negative control, CA13, demonstrated signal neutralizing activity equal to that of the parent 16D7 antibody on transfected cells stably expressing CXCR5.

Example 8

Chemotaxis Assay

CXCR5$^+$ HS Sultan cells (ATCC CRL1484) were added to the upper chamber of a transwell plate (Millipore) at $0.5 \times 10^6$ cells/well in the presence of 100 nM CXCL13 (R & D) or CTX buffer (RPMI without phenol red, containing 1% FBS, 0.5% BSA and 1 nM Na pyruvate) and migrating cells to the lower chamber were assessed. The two chambers were assembled and incubated for two hours. Cells in the lower chamber were counted after adding colorimetric reagent (Promega) and reading at $OD_{490}$.

CXCR5 specific migration was determined as the difference between the total number of migrated cells and the number of spontaneously migrating cells. If an anti-CXCR5 is tested, the cells are incubated with the antibody for 30 minutes prior to adding to the upper chamber. The degree of antibody inhibition is the ratio of the specific migration in the presence of antibody to the amount of migration in the absence of antibody. That ratio can be multiplied by 100% to yield a percent inhibition metric.

The antibodies of Example 7 were compared to the parent 16D7 antibody for the ability to neutralize chemotaxis. All of the humanized antibodies aside from negative control mAb CA13, neutralized chemotaxis in a profile comparable to that of 16D7 and 79B7, 14C9, 19H5, H28, 54G6, G7, 56H6. R&D MAB190 had intermediate activity while H28 and Abnova antibody 2C1 did not completely neutralize ligand-induced cell migration.

Example 9

Primary Human B Cell Reactivity Assay

Human PBMCs were isolated from whole blood using Accuspin columns (Sigma). PBMCs then were resuspended in BD Stain buffer (Becton Dickinson) at 20 million cells/ml. One µg of mouse anti-human CXCR5 monoclonal antibody was added to 50 µl PBMCs and allowed to bind for 20 minutes at 4° C. Cells were washed two times with BD Stain buffer. Fifty µl of the second antibody, goat-anti-mouse IgG-PE $F_{(ab')_2}$ (Beckman Coulter) diluted 1/100, were added to the PBMC-antibody cocktail and allowed to bind for 20 minutes at 4° C. Cells were washed three times with BD Stain buffer. A cocktail containing mouse anti-human CD20-FITC (BD) and CD4-APC (BD) at 1/50 dilution, each was added to the cells, which then were incubated for 20 minutes at 4° C. to assess B/T cell specificity. Cells were washed 3 times with BD Stain buffer and resuspended in 250 µl BD Stain buffer and subjected to FACS analysis on a FACStar Plus. Mouse anti-human CXCR5 antibody (R&D; mAb190) is used as a positive control. Titration curves were generated for humanized antibodies and Mean Fluorescence Intensity (MFI) plotted against concentration.

The humanized antibodies of Example 7 were tested for binding to human PMBCs.

The antibodies, aside from negative control CA13, bind and have the same titration profile on human B cells. Negative control CA13, demonstrated only background binding. BD clone RF8B2 binds poorly to human PBMCs.

Example 10

Cynomolgus B Cell Reactivity Assay

Cynomolgus (cyno) monkey whole blood was obtained from Bioreclamation, Inc. (Hicksville, N.Y.). The blood was shipped in BD Cell Preparation Tubes (CPT) post-centrifugation. The cyno PBMCs contained in the plasma layer were removed from the CPT tube into a 50 ml tube leaving the gradient gel layer undisturbed. The tube was washed with 5 ml PBS to completely extract all the cells and the wash was added to a fresh 50 ml tube. The cyno PBMCs were centrifuged at 1200 RPM for 10 minutes at 4° C. The pellet was resuspended in 1 ml BD FACS Stain buffer (BD). One million cells were used per assay. One µg of mouse anti-human CXCR5 monoclonal antibody (purified) was added to 50 µl PBMC and allowed to bind for 20 minutes at 4° C. Cells were washed 2 times with BD Stain buffer. Fifty µl of second antibody, goat anti-mouse IgG-PE $F_{(ab')_2}$ (Beckman Coulter) diluted 1/100, was added to the cells and allowed to bind for 20 minutes at 4° C. Cells were washed three times with BD Stain buffer. A cocktail containing mouse anti-human CD20-FITC (BD) and CD4-APC (BD) at 1/20 dilution each was added to cells for a 20 minute incubation at 4° C. for assessment of B/T cell specificity. Cells were washed 3 times with BD Stain buffer, and resuspended in 250 µl BD Stain buffer and subjected to FACS analysis on a FACStarPlus. Commercial mouse anti-human CXCR5 mAb (R&D; MAB 190) was used as a positive control.

Mouse monoclonal 11D6 of the instant invention reactive to human CXCR5, was compared to an IgG isotype control.

The humanized versions of 16D7 and the commercially available MAB190 were tested for reactivity to cynomolgus CXCR5. 79B7 also was tested.

Cells positive for CD20 and CXCR5 were found with MAB190 and 11D6. On the other hand, 16D7 and the humanized variants thereof, as well as G7 and BD RF8B2 and Abnova 2C1 did not bind to cynomolgus B cells. 14C9, 19H5, H28, 54G6, 56H6 and 79B7 also bound cynomolgus B cells.

The instant CXCR5 antibodies were used to study peripheral blood cells. B cells expressed CXCR5 and in at least one experiment, about 10% of peripheral T cells were found to express CXCR5.

Example 11

Sequencing of Anti-CXCR5 mABS

The mouse monoclonal antibodies were isotyped using a commercially available isotyping kit. The variable sequences of 16D7 and other anti-CXCR5 mAb were sequenced. Total RNA was isolated from about 5 million cells of the hybridoma using the Qiagen Qianeasy miniprep kit by following the kit protocol. First strand cDNA was synthesized using the Invitrogen Superscript kit (Cat 11904-018), the kit protocols were followed.

The heavy chain and light chain variable regions were first amplified using the following degenerate PCR primers and Taq polymerase (Roche) based on methods described in Wang et al. J Immunol Methods. 233:167-77, 2000.

```
Heavy chain:
Left primer:
                                       (SEQ ID NO: 2)
1: CTTCCGGAATTCSARGTNMAGCTGSAGSAGTC (SEQ ID NO: 3)
2: CTTCCGGAATTCSARGTNMAGCTGSAGSAGTCWGG Heavy chain:
Right primer:
                                       (SEQ ID NO: 4)
GGAGGATCCATAGACAGATGGGGGTGTCGTTTTGGC Light chain:
Left primer:
                                       (SEQ ID NO: 5)
GGAGCTCGAYATTGTGMTSACMCARWCTMCA Light chain:
Right primer:
                                       (SEQ ID NO: 6)
TATAGAGCTCAAGCTTGGATGGTGGGAAGATGGATACAGTTGGTGC
``` where R is either A or G; N is either A, G, T or C; M is either A or C; W is either A or T; S is G or C; and Y is C or T.

The PCR products were cloned into the pCR4-TOPO® using the Invitrogen TOPO TA Cloning® kit (Cat #: 45-0641) and sequenced using T3 and T7 primers. Sequences then were blasted against the gene bank database to deduce the leader sequences for cloning of full variable regions. Based on the blast results, the following primers (Chardes et al., FEBS Letters 452:386-394, 1999) were chosen for a second round of PCR amplification using Pfx polymerase (Invitrogen).

```
Heavy chain:
Left primer:
                                       (SEQ ID NO: 7)
CCAAGCTGTGTCCTRTCC Right primer:
                                       (SEQ ID NO: 8)
CGACAAGTCGACTAGCCCTTGACCAGGCATCC Light chain:
Left primer:
                                       (SEQ ID NO: 9)
WTCTCTRGAGTCAGTGGG Right primer:
                                       (SEQ ID NO: 10)
CGACTAGTCGACTGGTGGGAAGATGGATACAG
```

The PCR products were cloned into pCR-Blunt II®-TOPO® using the Invitrogen Zero Blunt® TOPO® PCR cloning kit (Cat 45-0245) and sequenced using T7 primers.

Once the light and heavy chains are sequenced, the nucleic acids can be recoded to optimize expression in, for example, human host cells.

Example 12

Transfectomas

NS0-eu cells are grown to a density of $1 \times 10^6$ cells/ml. The cells are maintained in exponential growth phase and medium is changed the day before transfection. The day of transfection, $40 \times 10^6$ cells are washed. Then, 10 μg of linearized nucleic acid, such as light chain DNA, and 10 μg of, for example, linearized heavy chain DNA are added to the cell suspension (the total DNA volume should be less than 50 μl) and the culture incubated on ice for 15 min. The DNA and cell mixture is transferred to a chilled cuvette (0.4 cm) and an electric pulse (750 V and 25 μF) is applied. The cuvette is placed on ice immediately after the electric pulse and kept on ice for 10-15 min. The cells are collected and plated. The cells are incubated in a 5% $CO_2$ incubator for 12-16 days or until colonies appear. The supernatant of the cell colonies or cells grown in suspension culture is tested by ELISA and positive transfectomas are cloned in fresh medium. To further screen the positive transfectomas, either titration ELISA or the Biacore assay is conducted. Expanded transfectomas are maintained in shaker flasks and antibody or derivative thereof collected from the supernatant.

Example 13

In Vivo Assays

Collagen-induced arthritis (CIA), a well-established model for human RA, has been used to demonstrate the efficacy of antibodies to TNFα (Williams et al., PNAS 1992, 89:9784-9788), as well as, fusion proteins of CTLA-4 and TNFα (Webb et al., Eur J. Immunol. 1996, 26:2320-2328; and Wooley et al., J. Immunol. 1993, 151:6602-6607). A rat anti-mouse CXCR5 monoclonal antibody, clone 1038, was profiled in a mouse model of CIA in which DBA/1J mice were immunized and boosted with chick collagen type II. Disease severity (which was visually scored by measuring paw swelling/inflammation) was monitored twice weekly, while joints collected at study termination were evaluated for changes in inflammation, pannus, cartilage destruction and bone erosion. Clone 1038, when administered in a prophylactic dosing regimen, significantly reduced both disease severity and joint pathology compared to isotype-treated CIA mice (repeated measure ANOVA, $p<0.05$).

An acute mouse model for assessing efficacy of 16D7-HC1-LC3 in in vivo chemotaxis was employed. Briefly, C57/

B16 mice (8-16 weeks of age) selectively expressing huCXCR5 on immunocytes, such as B cells, T cells and neutrophils, were generated by traditional transgenic methods using a CD11a promoter. The in vivo chemotaxis model is a neutrophil-driven model. On intraperitoneal administration of 20 µg of huCXCL13 ligand (R&D), mouse neutrophils expressing the huCXCR5 receptor migrated to the peritoneal cavity in response to a huCXCL13 gradient. Peritoneal cavity washes were used to recover cells 80 minutes post-intraperitoneal administration of huCXCL 13 and fluorocytometric analysis was used to quantify the number of huCXCR5-expressing neutrophils in 2 ml samples of peritoneal lavages that specifically migrated into the peritoneal cavity in response to huCXCL13 instillation. Neutrophils were identified by phenotypic markers, such as Ly6G, CD19 and CD11b. Subcutaneous administration of humanized anti-hCXCR5, 16D7-HC1LC3, at two different doses (7.5 µg or 15 µg) 24 hours prior to instillation of huCXCL13 showed efficacy in reducing huCXCR5-expressing neutrophil migration to the peritoneal cavity in response to huCXCL13 when compared to an isotype-treated control, the two CXCR5 antibody treated samples demonstrating essentially no statistically different levels of neutrophils as compared to the isotype negative control level of neutrophils. At 1.5 µg, the humanized CXCR5 antibody showed a low level of neutrophil migration inhibition as compared to the higher doses of CXCR5 antibody tested.

Example 14

Resurfacing

Resurfacing of the murine 16D7 clone followed the steps described in Proc. Natl. Acad. Sci. USA (1994) 91:969 and in U.S. Pat. No. 5,639,641.

The $V_L$ and $V_H$ sequences of 16D7 were blasted against the Protein Data Bank (Nucleic Acids Research, 28:235-242 (2000) or one can access the Protein Data Bank (PDB) on the internet, which contains the 3D coordinates of biological macromolecules, and the ten light and heavy chain amino acid sequences most similar to that of 16D7 were retrieved. The PDB identification codes are used for identifying the sequences.

The ten closest homologues for the variable light chain were 1MJU (J Mol Biol 332:423-435, 2003), 1AE6 (Proteins 29:161-171, 1997), 1QYG (Pozharski et al., "Carving a Binding Site: Structural Study of an Anti-Cocaine Antibody" in "Complex with Three Cocaine Analogs"), 1 UZG (J Virol 79:1223, 2005), 1UB5 (Beuscher et al., "Structure and Dynamics of Blue Fluorescent Antibody 19G2 at Blue and Violet Fluorescent Temperatures"), 1RUR (Proc Natl Acad Sci USA 110:2247-2252, 2004, 1FPT (Nat Struct Biol 2:232-243, 1995), 1QFU (Nat Struct Biol 6:530-534, 1999), 1NAK (Virology 315:159-173, 2003) and 1CGS (J Mol Biol 236:247-274, 1994) (redundant sequences were removed) and the ten closest homologues for the variable heavy chain are 1FNS (Nat Struct Biol 7:881-884, 2000), 1OAK (Nat Struct Biol 5:189-194, 1998), 1VFB (Proc Natl Acad Sci 91:1089-1093, 1994), 1CIC Nature 348:254-257, 1990), 1GIG (Acta Crystallogr D Biol Crystallogr 50:768-777, 1994), 1T4K (J Mol Biol 343:1269-1280, 2004), 1A7P (Marks et al.), 1FE8 (J Biol Chem 276:9985-9991, 2001), 1DL7 (J Exp Med 191: 2101-2112, 2000) and 1YY8 (Cancer Cell 7:301-311, 2005). The closest homologs for the light and heavy chain were 1MJU and 1FNS, respectively. Those two sequences were used to build a homology model of the variable domains which was subsequently energy-minimized by a conjugate gradient minimization of atomic coordinate positions with the CHARMM22 force field (J Comput Chem (1983) 4, 187; J Comput Chem (1986) 7, 591) as implemented in the MOE suite (Chemical Computing Group, Quebec, CA). The model was used to locate the CDR regions and the framework residues. The solvent accessibility for each variable region residue of the ten closest homologs for each antibody variable region was calculated and averaged in an Excel spreadsheet as implemented in a Scitegic protocol (Hill & Lewicki (2006) Statistics: Methods and Applications, Statsoft, Tulsa, Okla.). Positions with greater than a 30% average accessibility were considered surface residues. Positions with average accessibilities of between 25% and 30% were further considered depending on proximity to the CDR loops.

The surface positions of the murine 16D7 variable region were compared to the corresponding positions in the human antibody sequences. Only those residues which displayed an accessible surface area greater than 30%, with a few residues displaying an accessible surface area greater than 25% and which were flanking solvent exposed residues, were retained for the search. Some conserved residues in all immunoglobulin sequences were included to improve convergence of the search. Only germ line sequences were retained for analysis of the hits. The human antibody variable region surface with the most identical surface residues, with special consideration given to positions that come within 5.0 Å of a CDR, was chosen to replace the murine 16D7 antibody variable region surface residues.

None of the sequences contains any known B-cell or T-cell epitope listed in the Immune Epitope database (IEDB, Immune Epitope Database and Analysis Resource web site; PLoS Biol. 2005; 3(3):e91).

The original sequences of murine 16D7 variable domains are:

the light chain (CDRs are underlined):
(SEQ ID NO: 11)
DIVMTQAAPSVAVTPRESVSISCRSSKSLLHSSGKTYLY

WFLQRPGQSPQLLIYRMSNLASGVPDRFSGSGSGTAFTLRISRVEAEDV

GVYYCMQHLEYP YTFGGGTKLE IK;
and the heavy chain (CDRs are underlined)
(SEQ ID NO: 12)
QVQLKESGPGLVAPSQSLSITCTVSGFSLIDYGVNWIRQP

PGKGLEWLGVIWGDGTTYYNSALKSRLSIRKDNSQSQVFL

KMNSLQTDDTAMYYCARIVYWGQGTLVTVSA.

The retained set of surface residues for the search of the light chain included D1, V3, A7, P9, P15, R16, E17, S18, P45, G46, Q47, D65, R79, R82, E86, K108, E110 and K112.

The query for the light chain contains the set of surface residues defined above and the conserved amino acids, C23, W40, Q43, Y91, C93, F103, G104, G106 and T107, which were included for the convergence of the BLAST protocol. All the other amino acids could be any of the 20 naturally amino acids. The BLAST search was done against the human germline antibody sequence database compiled by the IMGT (International Immunogenetics Information Systems website, Molec Immunol, 2004, 40:647-659). The best scoring match was found to be X72482 (protein_id=CAA51150.1) from which was derived the light chain, LC4. LC5 and LC6 are two variants of VL4 (VL means variable light) that are suggested to address potential problematic residues in the light chain: 1 exposed methionine (M51) to be mutated to Leu (LC5 & LC6) and 1 potential deamidation site (LC6) where the asparagine N53 is changed to a serine residue. In total, 3 versions are proposed for the variable light chain which contain between 4 and 6 mutations when compared to the parent murine 16D7 clone. The corresponding mutations are given in the following Table 1. Sequential and Kabat numbering are given.

The retained set of surface residues for the variable heavy chain included Q1, Q3, K5, S7, P9, L11, S15, Q16, S20, P41, G42, K43, S61, A62, K64, S65, R70, S74, Q75, Q86, T87, D88, Q103, L106, A111, A112 and K113 (sequential numbering). The invariant amino acids which were included in the BLAST query for the convergence of the search were: C22, W36, 137, Q39, D89, Y93, C95, W101, G102, G104 and T105. The BLAST search was done against the human germline antibody sequence database compiled by IMGT. One version for the heavy chain (HC3) was retained. The two $V_H$ domains of AF062266 (protein_id=AAC18304.1) and AY393082 (protein_id=AAS86018.1), that showed the best matching score for the set of surface residues, exhibit equivalent similarity score and display identical surface residues. Consequently only a single sequence for the heavy chain was retained with ten mutations. The lower scoring sequences that have different surface residues were not retained as they have less polar residues suggestive of potential reduced solubility.

TABLE 1

| Light Chain (sequential numbering) | Light Chain (Kabat numbering) | Version5 (LC4) | Version6 (LC5) | Version7 (LC6) |
| --- | --- | --- | --- | --- |
| Ala7 | Ala7 | Ser | Ser | Ser |
| Pro9 | Pro9 | Leu | Leu | Leu |
| Arg16 | Arg16 | Gly | Gly | Gly |
| Met56 | Met51 | Met | Leu | Leu |
| Asn58 | Asn53 | Asn | Asn | Ser |
| Arg82 | Arg77 | Lys | Lys | Lys |
| In total for VL | | 4 mutations | 5 mutations | 6 mutations |
| Heavy Chain (sequential numbering) | Heavy Chain (Kabat numbering) | (HC3) | (HC3) | (HC3) |
| Lys5 | Lys5 | Gln | Gln | Gln |
| Gln16 | Gln16 | Glu | Glu | Glu |
| Ser61 | Ser61 | Pro | Pro | Pro |
| Ala62 | Ala62 | Ser | Ser | Ser |
| Arg70 | Arg70 | Ser | Ser | Ser |
| Gln75 | Gln75 | Lys | Lys | Lys |
| Gln86 | Gln83 | Thr | Thr | Thr |
| Thr87 | Thr84 | Ala | Ala | Ala |
| Asp88 | Asp85 | Ala | Ala | Ala |
| Ala111 | Ala113 | Ser | Ser | Ser |
| In total for VH | | 10 mutations | 10 mutations | 10 mutations |

Three versions are proposed for the light chain (LC4, LC5 and LC6). Individual mutations introduced through the resurfacing of the variable chains are noted in lowercase and underlined and CDRs are underlined. Resurfaced sequences of the variable regions are listed below, the constant domain (IgG4) is not included.

```
LC4:
                                     (SEQ ID NO: 13)
DIVMTQsAlS VAVTPqESVS ISCRSSKSLL HSSGKTYLYW
FLQRPGQSPQ LLIYRMSNLASGVPDRFSGS GSGTAFTLkI SRVEAE
DVGVYYCMQHLEYP YTFGGGTKLE IK

LC5:
                                     (SEQ ID NO: 14)
DIVMTQsAlS VAVTPqESVS ISCRSSKSLL HSSGKTYLYW
FLQRPGQSPQ LLIYRlSNLASGVPDRFSGS GSGTAFTLkI SRVEAE
DVGVYYCMQHLEYP YTFGGGTKLE IK

LC6:
                                     (SEQ ID NO: 15)
DIVMTQsAlS VAVTPqESVS ISCRSSKSLLHSSGKTYLYW
FLQRPGQSPQ LLIYRlSsnLASGVPDRFSGS GSGTAFTLkI SRVEA
EDVGVYYCMQHLEYPYTFGGGTKLE IK
```

One version was proposed for the heavy chain (VH3) (VH means variable heavy). Mutations introduced through the resurfacing of the variable chain are in lowercase and underlined, and the CDRs are underlined. The constant domain sequence is not included.

```
HC3:
                                     (SEQ ID NO: 16)
QVQLqESGPG LVAPSeSLSI TCTVSGFSLIDYGVNWIRQP
PGKGLEWLGVIWGDGTTYYN psLKSRLSIs KDNSkSQVFL KMNSL
taaDTAMYYCARIVYWGQGTLVTVS s
```

Nucleotide sequences were generated by OE-PCR and cloned into NheI/HindIII sites of the episomal expression vector pXL4214 (Durocher et al., NAR, 2002, 30(2), E9. Sequences are codon optimized for expression in human cells. $V_L$ was fused to IGKC (AAH93097). $V_H$ was fused to IGHG4 (AAH25985), lacking the C-terminal Lys (IGHG4ΔK). Sequences were validated by double strand sequencing.

```
LC4:
                                     (SEQ ID NO: 17)
MGWSCIILFLVATATGVHSDIVMTQSALSVAVTPGESVSISCRSSKSLL
HSSGKTYLYWFLQRPGQSPQLLIYRMSNLASGVPDRFSGSGSGTAFTLK
ISRVEAEDVGVYYCMQHLEYPYTFGGGTKLEIKRTVAAPSVFIFPPSDE
QLKSGTASVVCLLNNFYPREAKVQWKVDNALQSGNSQESVTEQDSKDST
YSLSSTLTLSKADYEKHKVYACEVTHQGLSSPVTKSFNRGEC (SEQ ID NO: 18)
GCTAGCACCATGGGCTGGAGCTGCATCATCCTGTTCCTGGTGGCCA
CCGCCACCGGCGTGCACAGCGACATCGTGATGACCCAGAGCGCCCTCAG
CGTGGCCGTGACCCCCGGCGAGAGCGTGAGCATCAGCTGCCGCAGCAGC
AAGAGCCTGCTGCACAGCAGCGGCAAGACCTACCTGTACTGGTTCCTGC
AGCGCCCCGGCCAGAGCCCCCAGCTGCTGATCTACCGCATGAGCAACCT
GGCCAGCGGCGTGCCCGACCGCTTCAGCGGCAGCGGCAGCGGCACCGCC
TTCACCCTGAAGATCAGCCGCGTGGAGGCCGAGGACGTGGGCGTGTACT
ACTGCATGCAGCACCTGGAGTACCCCTACACCTTCGGCGGCGGCACCAA
GCTGGAGATCAAGCGTACGGTGGCCGCTCCTTCCGTGTTCATCTTCCCT
CCCTCCGACGAGCAGCTGAAGTCCGGCACCGCCTCCGTGGTGTGTCTGC
TGAACAACTTCTACCCTCGGGAGGCCAAGGTGCAGTGGAAGGTGGACAA
CGCCCTGCAGTCCGGCAACTCCCAGGAGTCCGTCACCGAGCAGGACTCC
```

-continued

AAGGACAGCACCTACTCCCTGTCCTCCACCCTGACCCTGTCCAAGGCCG

ACTACGAGAAGCACAAGGTGTACGCCTGTGAGGTGACCCACCAGGGCCT

GTCCAGCCCTGTGACCAAGTCCTTCAACCGGGGCGAGTGCTGAAGCTT

LC5:
(SEQ ID NO: 19)
MGWSCIILFLVATATGVHSDIVMTQSALSVAVTPGESVSISCRSSKSLL

HSSGKTYLYWFLQRPGQSPQLLIYRLSNLASGVPDRFSGSGSGTAFTLK

ISRVEAEDVGVYYCMQHLEYPYTFGGGTKLEIKRTVAAPSVFIFPPSDE

QLKSGTASVVCLLNNFYPREAKVQWKVDNALQSGNSQESVTEQDSKDST

YSLSSTLTLSKADYEKHKVYACEVTHQGLSSPVTKSFNRGEC (SEQ ID NO: 20)
GCTAGCACCATGGGCTGGAGCTGCATCATCCTGTTCCTGGTGGCCA

CCGCCACCGGCGTGCACAGCGACATCGTGATGACCCAGAGCGCCCTCAG

CGTGGCCGTGACCCCCGGCGAGAGCGTGAGCATCAGCTGCCGCAGCAGC

AAGAGCCTGCTGCACAGCAGCGGCAAGACCTACCTGTACTGGTTCCTGC

AGCGCCCCGGCCAGAGCCCCCAGCTGCTGATCTACCGCCTGAGCAACCT

GGCCAGCGGCGTGCCCGACCGCTTCAGCGGCAGCGGCAGCGGCACCGCC

TTCACCCTGAAGATCAGCCGCGTGGAGGCCGAGGACGTGGGCGTGTACT

ACTGCATGCAGCACCTGGAGTACCCCTACACCTTCGGCGGCGGCACCAA

GCTGGAGATCAAGCGTACGGTGGCCGCTCCTTCCGTGTTCATCTTCCCT

CCCTCCGACGAGCAGCTGAAGTCCGGCACCGCCTCCGTGGTGTGTCTGC

TGAACAACTTCTACCCTCGGGAGGCCAAGGTGCAGTGGAAGGTGGACAA

CGCCCTGCAGTCCGGCAACTCCCAGGAGTCCGTCACCGAGCAGGACTCC

AAGGACAGCACCTACTCCCTGTCCTCCACCCTGACCCTGTCCAAGGCCG

ACTACGAGAAGCACAAGGTGTACGCCTGTGAGGTGACCCACCAGGGCCT

GTCCAGCCCTGTGACCAAGTCCTTCAACCGGGGCGAGTGCTGAAGCTT

LC6:
(SEQ ID NO: 21)
MGWSCIILFLVATATGVHSDIVMTQSALSVAVTPGESVSISCRSSKSLL

HSSGKTYLYWFLQRPGQSPQLLIYRLSSLASGVPDRFSGSGSGTAFTLK

ISRVEAEDVGVYYCMQHLEYPYTFGGGTKLEIKRTVAAPSVFIFPPSDE

QLKSGTASVVCLLNNFYPREAKVQWKVDNALQSGNSQESVTEQDSKDST

YSLSSTLTLSKADYEKHKVYACEVTHQGLSSPVTKSFNRGEC (SEQ ID NO: 22)
GCTAGCACCATGGGCTGGAGCTGCATCATCCTGTTCCTGGTGGCCA

CCGCCACCGGCGTGCACAGCGACATCGTGATGACCCAGAGCGCCCTCAG

CGTGGCCGTGACCCCCGGCGAGAGCGTGAGCATCAGCTGCCGCAGCAGC

AAGAGCCTGCTGCACAGCAGCGGCAAGACCTACCTGTACTGGTTCCTGC

AGCGCCCCGGCCAGAGCCCCCAGCTGCTGATCTACCGCCTGAGCAGCCT

GGCCAGCGGCGTGCCCGACCGCTTCAGCGGCAGCGGCAGCGGCACCGCC

TTCACCCTGAAGATCAGCCGCGTGGAGGCCGAGGACGTGGGCGTGTACT

ACTGCATGCAGCACCTGGAGTACCCCTACACCTTCGGCGGCGGCACCAA

GCTGGAGATCAAGCGTACGGTGGCCGCTCCTTCCGTGTTCATCTTCCCT

CCCTCCGACGAGCAGCTGAAGTCCGGCACCGCCTCCGTGGTGTGTCTGC

TGAACAACTTCTACCCTCGGGAGGCCAAGGTGCAGTGGAAGGTGGACAA

CGCCCTGCAGTCCGGCAACTCCCAGGAGTCCGTCACCGAGCAGGACTCC

AAGGACAGCACCTACTCCCTGTCCTCCACCCTGACCCTGTCCAAGGCCG

ACTACGAGAAGCACAAGGTGTACGCCTGTGAGGTGACCCACCAGGGCCT

GTCCAGCCCTGTGACCAAGTCCTTCAACCGGGGCGAGTGCTGAAGCTT

HC3:
(SEQ ID NO: 23)
MGWSCIILFLVATATGVHSQVQLQESGPGLVAPSESLSITCTVSGFSLI

DYGVNWIRQPPGKGLEWLGVIWGDGTTYYNPSLKSRLSISKDNSKSQVF

LKMNSLTAADTAMYYCARIVYWGQGTLVTVSSASTKGPSVFPLAPCSRS

TSESTAALGCLVKDYFPEPVTVSWNSGALTSGVHTFPAVLQSSGLYSLS

SVVTVPSSSLGTKTYTCNVDHKPSNTKVDKRVESKYGPPCPSCPAPEFL

GGPSVFLFPPKPKDTLMISRTPEVTCVVVDVSQEDPEVQFNWYVDGVEV

HNAKTKPREEQFNSTYRVVSVLTVLHQDWLNGKEYKCKVSNKGLPSSIE

KTISKAKGQPREPQVYTLPPSQEEMTKNQVSLTCLVKGFYPSDIAVEWE

SNGQPENNYKTTPPVLDSDGSFFLYSRLTVDKSRWQEGNVFSCSVMHEA

LHNHYTQKSLSLSLG (SEQ ID NO: 24)
GCTAGCACCATGGGCTGGAGCTGCATCATCCTGTTCCTGGTGGCCA

CCGCCACCGGCGTGCACAGCCAGGTGCAGCTGCAGGAGAGCGGCCCCGG

CCTGGTGGCCCCCAGCGAGAGCCTGAGCATCACCTGCACCGTGAGCGGC

TTCAGCCTGATCGACTACGGCGTGAACTGGATCCGCCAGCCCCCCGGCA

AGGGCCTGGAGTGGCTGGGCGTGATCTGGGGCGACGGCACCACCTACTA

CAACCCCAGCCTGAAGAGCCGCCTGAGCATCTCCAAGGACAACAGCAAG

AGCCAGGTGTTCCTGAAGATGAACAGCCTGACCGCCGCCGACACCGCCA

TGTACTACTGCGCCCGCATCGTGTACTGGGGCCAGGGCACCCTGGTGAC

CGTGAGCAGCGCCAGCACCAAGGGCCCTTCCGTGTTCCCTCTGGCCCCT

TGCTCCCGGTCCACCTCCGAGTCCACCGCCGCTCTGGGCTGCCTGGTGA

AGGACTACTTCCCTGAGCCTGTGACCGTGTCCTGGAACTCTGGCGCCCT

GACCTCCGGCGTGCACACCTTCCCTGCCGTGCTGCAGTCCTCCGGCCTG

TACTCCCTGTCCTCCGTGGTGACCGTGCCTTCCTCCTCCCTGGGCACCA

AGACCTACACCTGTAACGTGGACCACAAGCCTTCCAACACCAAGGTGGA

CAAGCGGGTGGAGTCCAAGTACGGCCCTCCTTGCCCTTCCTGCCCTGCC

CCTGAGTTCCTGGGCGGACCTAGCGTGTTCCTGTTCCCTCCTAAGCCTA

AGGACACCCTGATGATCTCCCGGACCCCTGAGGTGACCTGTGTGGTGGT

GGACGTGTCCCAGGAGGACCCTGAGGTCCAGTTCAACTGGTACGTGGAC

GGCGTGGAGGTGCACAACGCCAAGACCAAGCCTCGGGAGGAGCAGTTCA

ATTCCACCTACCGGGTGGTGTCTGTGCTGACCGTGCTGCACCAGGACTG

GCTGAACGGCAAAGAATACAAGTGTAAGGTCTCCAACAAGGGCCTGCCC

TCCTCCATCGAGAAAACCATCTCCAAGGCCAAGGGCCAGCCTAGGGAGC

CTCAGGTGTACACCCTGCCTCCTAGCCAGGAAGAGATGACCAAGAACCA

```
-continued
GGTGTCCCTGACCTGTCTGGTGAAGGGCTTCTACCCTTCCGACATCGCC

GTGGAGTGGGAGTCCAACGGCCAGCCTGAGAACAACTACAAGACCACCC

CTCCTGTGCTGGACTCCGACGGCTCCTTCTTCCTGTACTCCAGGCTGAC

CGTGGACAAGTCCCGGTGGCAGGAGGGCAACGTCTTTTCCTGCTCCGTG

ATGCACGAGGCCCTGCACAACCACTACACCCAGAAGTCCCTGTCCCTGT

CTCTGGGCTGAAGCTT
```

Example 15

Humanization

The $V_L$ and $V_H$ sequences of 16D7 were blasted and the closest homologues for the variable light chain are 1MH5, 1MJJ and 1MJU (J Mol Biol 332:423-435, 2003), with equivalent similarity scores. 1MJU was retained as a template because of high accuracy of the crystal structure, which had been determined down to 1.22 Å resolution. The closest homologue for the heavy chain was found to be 1FNS (Nat Struct Biol 7:881-884, 2000). The structures, 1MJU and 1FNS, were used to build up a homology model of the variable domains which was subsequently energy minimized using standard procedures. A molecular dynamic (MD) calculation of a 3D homology model of 16D7 was subsequently performed for 1.7 nanoseconds in Generalized Born implicit solvent (see Gallicchio & Levy, J Comput Chem 2004, 25:479-499).

The MD starts by an initialization of the velocities from a Gaussian distribution at 298.15° K, followed by an equilibration period of 300 ps. During the MD, all bonds are constrained using the SHAKE algorithm (see Barth. Et al., J Comp Chem, 1995, 16:1192-1209), the time step was 1 femtosecond (fs), and the simulation, based on the Verlet integration algorithm, was run in the canonical NVT (number of particles, volume and temperature) ensemble at a temperature of 298.15° K. During the production period, 1,700 snapshots were then stored, one every 1 ps. The 1,700 conformations of the murine antibody constitute the ensemble on which the following analysis was performed to identify the most flexible residues. The Scientific Vector Language (SVL), available within the MOE molecular modeling environment, (Molecular Operating Environment (MOE), Chemical Computing Group, Quebec, Canada) was used to code the following analysis. First, each snapshot, N, was optimally superposed onto its predecessor, the snapshot N−1, to control the overall rotational and translational motions which occur during the MD modeling and calculation. The superposition was obtained by minimizing the Root Mean Square Distance (RMSD) between all pairs of corresponding atoms from the two snapshots. Only the heavy atoms of the antibody backbone were considered in the superposition exercise. Using the same superposition method, each snapshot then was superposed onto the medoïd snapshot. The medoïd snapshot is the antibody conformation with the Cartesian coordinates the closest from the average coordinates of all conformations.

For each of the antibody residue i, the RMSD between the heavy atoms of the conformation j and a medoïd reference conformation k were calculated. The RMSD has the following formula:

$$RMSDj = \sqrt{\frac{\sum_{i=1}^{m}(d_{ik})^2}{m}},$$

with $d_{jk}$ defined as the Euclidean distance expressed in Angstroms (Å) between the heavy atom 1 of the residue j and its counterpart of the medoïd reference conformation k. For the pairwise association of heavy atoms 1, the symmetry of the side-chain heavy atoms for the amino acids, Asp, Leu, Val, Glu, Arg, Phe and Tyr, also was considered. The reference conformation k varies from one residue to another, and corresponds to the medoïd conformation k with the closest Euclidean distance to the average coordinates of all conformations of the studied residue i. Then, for each residue i, a distribution of 1,700 RMSD values, which reflects the variation of coordinates of the residue i in the course of the MD, was obtained. By aggregating all the RMSD values of all the residues of the studied antibody, a global distribution of all RMSDs was obtained. The global distribution of all RMSD then was used as a reference distribution. If the residue i is highly flexible, then a statistical test was performed to decide whether the observed mean RMSD of residue i, $m_i$, was significantly higher than the global mean RMSD for all residues, $m_g$. As the sample is large, e.g. 1,700 for the analysis of clone 16D7, a one-tailed Z-test (see Dorofeev & Grant, "Statistics for real-life sample surveys. Non-simple-random samples and weighted data" 2006. Cambridge University Press) with the null-hypothesis $H_0$ being that "the observed $m_i$ is lower than the global $m_g$" was used to calculate the statistic, $Z_i$ according to the formula:

$$Zi = \frac{(m_i - m_{global})}{\sqrt{\frac{sd_i}{n}}},$$

where $m_i$ is the mean RMSD calculated from the RMSD distribution of residue i, $m_g$ is the mean RMSD calculated from the global RMSD distribution, $sd_i$ is the standard deviation calculated from the RMSD distribution of residue i and n is the sample size, i.e. n=1,700 for the analysis of the 16D7 clone. The calculated Zi was then compared to the cumulative probabilities of the standard normal distribution to assess a 99.9% level of significance of the alternative hypothesis, i.e., that "the observed in, is higher than the global $m_g$". That corresponded to a Zi≥3.08. The Zi statistic, which can be viewed as a flexibility score, is not correlated with either the molecular weight or the number of heavy atoms of the antibody residue ($r^2$=0.014 and 0.0009, respectively when analyzing the 16D7 anti-CXCR5 model MD).

The set of flexible residues for the light chain include the following residues (sequential numbering): D1, T14, P15, R16, E17, Q47, D65, S72 R79, R82, E86, K108, E110 and K112; and for the heavy chain include the following residues: Q1, V2, Q3, L11, S15, Q16, S61, A62, K64, S65, R70, D72, Q75, K81, M82, N83, Q86, Q103, 5110, A111, A112 and K113. The flexible portions of 16D7 were compared to the corresponding positions of human antibody sequences in the September 2005 version of the ImMunoGeneTics Database website.

Those residues which display a significantly high flexible score and a few flanking residues that preserve the 3D structures of the flexible residues were retained for the search.

The human antibody variable region with the most identical flexible residues, with special considerations given to positions that come within 5.0 Å of a CDR, was chosen to replace the murine the 16D7 antibody variable region flexible residues. The resulting humanized sequences were blasted for sequence similarity in the UniProtKB/SwissProt database providing confidence that reasonable assumptions had been made. All sequences showed a high degree of similarity to a number of human antibodies. In addition, none of the sequences contains any known B-cell or T-cell epitope listed in the IEDB database.

The best sequence match in the IEDB for the light chain (LC1, LC2 and LC3) was KPGQPPRLLIYDASNRATGIPA (SEQ ID NO:25), which covers CDR2 but has significant residue difference as typified by a 56% sequence identity obtained from a BLAST search within the IEDB database.

The best match in the IEDB for the heavy chain (HC1 and HC2) was TDDTAMYYCAR1 (SEQ ID NO:26) which is located before the start of the CDR3. The sequence exhibits 61% sequence identity with the peptide SEDSALYYCARD (SEQ ID NO:27), making it unlikely to be a potential human T cell epitope (J Exp Med (1995) 181, 1540)

Original sequences of murine 16D7 variable domains are:

```
light chain (CDRs underlined):
                                       (SEQ ID NO: 28)
DIVMTQAAPSVAVTPRESVSISCRSSKSLLHSSGKTYLY

WFLQRPGQSPQLLIYRMSNLASGVPDRFSGSGSGTAFTLRISRVEAEDV

GVYYCMQHLEYPYTFGGGTKLE IK;
and heavy chain (CDRs underlined):
                                       (SEQ ID NO: 29)
QVQLKESGPGLVAPSQSLSITCTVSGFSLIDYGVNWIRQP

PGKGLEWLGVIWGDGTTYYNSALKSRLSIRKDNSQSQVFLKMNSLQTDD

TAMYYCARIVYWGQGTLVTVS A.
```

Two versions for the heavy chain (HC1 & HC2) and three versions were suggested for the light chain (LC1, LC2 and LC3). Both versions of the heavy chain are derived from AF262096/AAF79987 and AB063657/BAC01285.1, respectively. The two sequences exhibit equivalent similarity score, but were kept because the sets of residues to mutate appear relatively different and display different physico-chemical properties. The LC1 sequence is derived from BAC01682/AB064054.1 and there are only two residues to be mutated. LC2 and LC3 are variants of LC1 that are suggested to address potential problematic residues in the light chain: an exposed methionine (M51) mutated to Leu (versions 3 and 4) and one potential deamidation site (version 4) where the asparagine, N53, is changed to a serine residue. Not all combinations were retained but four cover most of the key points to be addressed. Kabat numbering is used.

TABLE 2

| Light Chain (Sequential numbering) | Light Chain (Kabat numbering) | Version 1 (LC1) | Version 2 (LC1) | Version 3 (LC2) | Version 4 (LC3) |
|---|---|---|---|---|---|
| Arg16 | Arg16 | Gly | Gly | Gly | Gly |
| Glu17 | Glu17 | Ala | Ala | Ala | Ala |
| Met56 | Met51 | Met | Met | Leu | Leu |
| Asn58 | Asn53 | Asn | Asn | Asn | Ser |
|  | In total for VL | 2 mutations | 2 mutations | 3 mutations | 4 mutations |
| Heavy Chain | Heavy Chain | (HC1) | (HC2) | (HC1) | (HC1) |
| Gln1 | Gln1 | Gln | Glu | Gln | Gln |
| Ser15 | Ser15 | Ser | Gly | Ser | Ser |
| Gln16 | Gln16 | Glu | Gly | Glu | Glu |
| Ser61 | Ser61 | Pro | Ala | Pro | Pro |
| Ala62 | Ala62 | Ser | Pro | Ser | Ser |
| Ser65 | Ser65 | Ser | Gly | Ser | Ser |
| Arg70 | Arg70 | Ser | Ser | Ser | Ser |
| Gln75 | Gln75 | Lys | Lys | Lys | Lys |
| Lys81 | Lys81 | Lys | Gln | Lys | Lys |
| Met82 | Met82 | Val | Met | Val | Val |
| Asn83 | Asn82A | Thr | Asn | Thr | Thr |
| Gln86 | Gln83 | Thr | Lys | Thr | Thr |
| Ala111 | Ala113 | Ala | Ser | Ala | Ala |
|  | In total for VH | 8 mutations | 11 mutations | 8 mutations | 8 mutations |

Mutations introduced through the humanization of the variable chains are in lowercase and underlined and CDRs are underlined. The constant domains are not included.

```
LC1:
                                       (SEQ ID NO: 30)
DIVMTQAAPSVAVTPqaSVSISCRSSKSLLHSSGKTYLYW

FLQRPGQSPQLLIYRMSNLASGVPDRFSGSGSGTAFTLRISRVEAEDVG

VYYCMQHLEYPYTFGGGTKLE IK

LC2:
                                       (SEQ ID NO: 31)
DIVMTQAAPSVAVTPqaSVS ISCRSSKSLLHSSGKTYLYW

FLQRPGQSPQLLIYR1SNLASGVPDRFSGSGSGTAFTLRISRVEAEDVG

VYYCMQHLEYPYTFGGGTKLEIK

LC3:
                                       (SEQ ID NO: 32)
DIVMTQAAPSVAVTPqaSVSISCRSSKSLLHSSGKTYLYW

FLQRPGQSPQLLIYR1SsLASGVPDRFSGSGSGTAFTLRISRVEAEDVG

VYYCMQHLEYPYTFGGGTKLEIK

HC1:
                                       (SEQ ID NO: 33)
QVQLKESGPGLVAPSeSLSITCTVSGFSLIDYGVNWIRQP

PGKGLEWLGVIWGDGTTYYNpsLKSRLSIsKDNSkSQVFLKvtSLtTDD

TAMYYCARIVYWGQGTLVTVSA

HC2:
                                       (SEQ ID NO: 34)
eVQLKESGPGLVAPggSLSITCTVSGFSLIDYGVNWIRQP

PGKGLEWLGVIWGDGTTYYNapLKgRLSIsKDNSkSQVFLqMNSLkTDD

TAMYYCARIVYWGQGTLVTVSs
```

The sequences of the chimeric constructs are as follows:

```
Chimeric LC Sequence
                                       (SEQ ID NO: 35)
MGWSCIILFLVATATGVHSDIVMTQAAPSVAVTPRESVSISCRSSKSLL

HSSGKTYLYWFLQRPGQSPQLLIYRMSNLASGVPDRFSGSGSGTAFTLR

ISRVEAEDVGVYYCMQHLEYPYTFGGGTKLEIKRTVAAPSVFIFPPSDE
```

-continued

QLKSGTASVVCLLNNFYPREAKVQWKVDNALQSGNSQESVTEQDSKDST

YSLSSTLTLSKADYEKHKVYACEVTHQGLSSPVTKSFNRGEC (SEQ ID NO: 36)
GCTAGCACCATGGGCTGGAGCTGCATCATCCTGTTCCTGGTGGCCA

CCGCCACCGGCGTGCACAGCGACATCGTGATGACCCAGGCCGCCCCCAG

CGTGGCCGTGACCCCCCGCGAGAGCGTGAGCATCAGCTGCCGCAGCAGC

AAGAGCCTGCTGCACAGCAGCGGCAAGACCTACCTGTACTGGTTCCTGC

AGCGCCCCGGCCAGAGCCCCCAGCTGCTGATCTACCGCATGAGCAACCT

GGCCAGCGGCGTGCCCGACCGCTTCAGCGGCAGCGGCAGCGGCACCGCC

TTCACCCTGCGCATCAGCCGCGTGGAGGCCGAGGACGTGGGCGTGTACT

ACTGCATGCAGCACCTGGAGTACCCCTACACCTTCGGCGGCGGCACCAA

GCTGGAGATCAAGCGTACGGTGGCCGCTCCTTCCGTGTTCATCTTCCCT

CCCTCCGACGAGCAGCTGAAGTCCGGCACCGCCTCCGTGGTGTGTCTGC

TGAACAACTTCTACCCTCGGGAGGCCAAGGTGCAGTGGAAGGTGGACAA

CGCCCTGCAGTCCGGCAACTCCCAGGAGTCCGTCACCGAGCAGGACTCC

AAGGACAGCACCTACTCCCTGTCCTCCACCCTGACCCTGTCCAAGGCCG

ACTACGAGAAGCACAAGGTGTACGCCTGTGAGGTGACCCACCAGGGCCT

GTCCAGCCCTGTGACCAAGTCCTTCAACCGGGGCGAGTGCTGAAGCTT

Chimeric HC Sequence (SEQ ID NO: 37)
MGWSCIILFLVATATGVHSQVQLKESGPGLVAPSQSLSITCTVSGFSLI

DYGVNWIRQPPGKGLEWLGVIWGDGTTYYNSALKSRLSIRKDNSQSVF

LKMNSLQTDDTAMYYCARIVYWGQGTLVTVSAASTKGPSVFPLAPCSRS

TSESTAALGCLVKDYFPEPVTVSWNSGALTSGVHTFPAVLQSSGLYSLS

SVVTVPSSSLGTKTYTCNVDHKPSNTKVDKRVESKYGPPCPSCPAPEFL

GGPSVFLFPPKPKDTLMISRTPEVTCVVVDVSQEDPEVQFNWYVDGVEV

HNAKTKPREEQFNSTYRVVSVLTVLHQDWLNGKEYKCKVSNKGLPSSIE

KTISKAKGQPREPQVYTLPPSQEEMTKNQVSLTCLVKGFYPSDIAVEWE

SNGQPENNYKTTPPVLDSDGSFFLYSRLTVDKSRWQEGNVFSCSVMHEA

LHNHYTQKSLSLSLG (SEQ ID NO: 38)
GCTAGCACCATGGGCTGGAGCTGCATCATCCTGTTCCTGGTGGCCA

CCGCCACCGGCGTGCACAGCCAGGTGCAGCTGAAGGAGAGCGGCCCCGG

CCTGGTGGCCCCCAGCCAGAGCCTGAGCATCACCTGCACCGTGAGCGGC

TTCAGCCTGATCGACTACGGCGTGAACTGGATCCGCCAGCCCCCCGGCA

AGGGCCTGGAGTGGCTGGGCGTGATCTGGGGCGACGGCACCACCTACTA

CAACAGCGCCCTGAAGAGCCGCCTGAGCATCCGCAAGGACAACAGCCAG

AGCCAGGTGTTCCTGAAGATGAACAGCCTGCAGACCGACGACACCGCCA

TGTACTACTGCGCCCGCATCGTGTACTGGGGCCAGGGCACCCTGGTGAC

CGTGAGCGCCGCCAGCACCAAGGGCCCTTCCGTGTTCCCTCTGGCCCCT

TGCTCCCGGTCCACCTCCGAGTCCACCGCCGCTCTGGGCTGCCTGGTGA

AGGACTACTTCCCTGAGCCTGTGACCGTGTCCTGGAACTCTGGCGCCCT

GACCTCCGGCGTGCACACCTTCCCTGCCGTGCTGCAGTCCTCCGGCCTG

TACTCCCTGTCCTCCGTGGTGACCGTGCCTTCCTCCTCCCTGGGCACCA

AGACCTACACCTGTAACGTGGACCACAAGCCTTCCAACACCAAGGTGGA

CAAGCGGGTGGAGTCCAAGTACGGCCCTCCTTGCCCTTCCTGCCCTGCC

CCTGAGTTCCTGGGCGGACCTAGCGTGTTCCTGTTCCCTCCTAAGCCTA

AGGACACCCTGATGATCTCCCGGACCCCTGAGGTGACCTGTGTGGTGGT

GGACGTGTCCCAGGAGGACCCTGAGGTCCAGTTCAACTGGTACGTGGAC

GGCGTGGAGGTGCACAACGCCAAGACCAAGCCTCGGGAGGAGCAGTTCA

ATTCCACCTACCGGGTGGTGTCTGTGCTGACCGTGCTGCACCAGGACTG

GCTGAACGGCAAAGAATACAAGTGTAAGGTCTCCAACAAGGGCCTGCCC

TCCTCCATCGAGAAAACCATCTCCAAGGCCAAGGGCCAGCCTAGGGAGC

CTCAGGTGTACACCCTGCCTCCTAGCCAGGAAGAGATGACCAAGAACCA

GGTGTCCCTGACCTGTCTGGTGAAGGGCTTCTACCCTTCCGACATCGCC

GTGGAGTGGGAGTCCAACGGCCAGCCTGAGAACAACTACAAGACCACCC

CTCCTGTGCTGGACTCCGACGGCTCCTTCTTCCTGTACTCCAGGCTGAC

CGTGGACAAGTCCCGGTGGCAGGAGGGCAACGTCTTTTCCTGCTCCGTG

ATGCACGAGGCCCTGCACAACCACTACACCCAGAAGTCCCTGTCCCTGT

CTCTGGGCTGAAGCTT

Humanized VL Sequences

LC1:

(SEQ ID NO: 39)
MGWSCIILFLVATATGVHSDIVMTQAAPSVAVTPGASVSISCRSSKSLL

HSSGKTYLYWFLQRPGQSPQLLIYRMSNLASGVPDRFSGSGSGTAFTLR

ISRVEAEDVGVYYCMQHLEYPYTFGGGTKLEIKRTVAAPSVFIFPPSDE

QLKSGTASVVCLLNNFYPREAKVQWKVDNALQSGNSQESVTEQDSKDST

YSLSSTLTLSKADYEKHKVYACEVTHQGLSSPVTKSFNRGEC (SEQ ID NO: 40)
GCTAGCACCATGGGCTGGAGCTGCATCATCCTGTTCCTGGTGGCCA

CCGCCACCGGCGTGCACAGCGACATCGTGATGACCCAGGCCGCCCCCAG

CGTGGCCGTGACCCCCGGCGCCAGCGTGAGCATCAGCTGCCGCAGCAGC

AAGAGCCTGCTGCACAGCAGCGGCAAGACCTACCTGTACTGGTTCCTGC

AGCGCCCCGGCCAGAGCCCCCAGCTGCTGATCTACCGCATGAGCAACCT

GGCCAGCGGCGTGCCCGACCGCTTCAGCGGCAGCGGCAGCGGCACCGCC

TTCACCCTGCGCATCAGCCGCGTGGAGGCCGAGGACGTGGGCGTGTACT

ACTGCATGCAGCACCTGGAGTACCCCTACACCTTCGGCGGCGGCACCAA

GCTGGAGATCAAGCGTACGGTGGCCGCTCCTTCCGTGTTCATCTTCCCT

CCCTCCGACGAGCAGCTGAAGTCCGGCACCGCCTCCGTGGTGTGTCTGC

TGAACAACTTCTACCCTCGGGAGGCCAAGGTGCAGTGGAAGGTGGACAA

CGCCCTGCAGTCCGGCAACTCCCAGGAGTCCGTCACCGAGCAGGACTCC

AAGGACAGCACCTACTCCCTGTCCTCCACCCTGACCCTGTCCAAGGCCG

ACTACGAGAAGCACAAGGTGTACGCCTGTGAGGTGACCCACCAGGGCCT

GTCCAGCCCTGTGACCAAGTCCTTCAACCGGGGCGAGTGCTGAAGCTT

LC2:
(SEQ ID NO: 41)
MGWSCIILFLVATATGVHSDIVMTQAAPSVAVTPGASVSISCRSSKSLL
HSSGKTYLYWFLQRPGQSPQLLIYRLSNLASGVPDRFSGSGSGTAFTLR
ISRVEAEDVGVYYCMQHLEYPYTFGGGTKLEIKRTVAAPSVFIFPPSDE
QLKSGTASVVCLLNNFYPREAKVQWKVDNALQSGNSQESVTEQDSKDST
YSLSSTLTLSKADYEKHKVYACEVTHQGLSSPVTKSFNRGEC (SEQ ID NO: 42)
GCTAGCACCATGGGCTGGAGCTGCATCATCCTGTTCCTGGTGGCCA
CCGCCACCGGCGTGCACAGCGACATCGTGATGACCCAGGCCGCCCCCAG
CGTGGCCGTGACCCCCGGCGCCAGCGTGAGCATCAGCTGCCGCAGCAGC
AAGAGCCTGCTGCACAGCAGCGGCAAGACCTACCTGTACTGGTTCCTGC
AGCGCCCCGGCCAGAGCCCCCAGCTGCTGATCTACCGCCTGAGCAACCT
GGCCAGCGGCGTGCCCGACCGCTTCAGCGGCAGCGGCAGCGGCACCGCC
TTCACCCTGCGCATCAGCCGCGTGGAGGCCGAGGACGTGGGCGTGTACT
ACTGCATGCAGCACCTGGAGTACCCCTACACCTTCGGCGGCGGCACCAA
GCTGGAGATCAAGCGTACGGTGGCCGCTCCTTCCGTGTTCATCTTCCCT
CCCTCCGACGAGCAGCTGAAGTCCGGCACCGCCTCCGTGGTGTGTCTGC
TGAACAACTTCTACCCTCGGGAGGCCAAGGTGCAGTGGAAGGTGGACAA
CGCCCTGCAGTCCGGCAACTCCCAGGAGTCCGTCACCGAGCAGGACTCC
AAGGACAGCACCTACTCCCTGTCCTCCACCCTGACCCTGTCCAAGGCCG
ACTACGAGAAGCACAAGGTGTACGCCTGTGAGGTGACCCACCAGGGCCT
GTCCAGCCCTGTGACCAAGTCCTTCAACCGGGGCGAGTGCTGAAGCTT

LC3:
(SEQ ID NO: 43)
MGWSCIILFLVATATGVHSDIVMTQAAPSVAVTPGASVSISCRSSKSLL
HSSGKTYLYWFLQRPGQSPQLLIYRLSSLASGVPDRFSGSGSGTAFTLR
ISRVEAEDVGVYYCMQHLEYPYTFGGGTKLEIKRTVAAPSVFIFPPSDE
QLKSGTASVVCLLNNFYPREAKVQWKVDNALQSGNSQESVTEQDSKDST
YSLSSTLTLSKADYEKHKVYACEVTHQGLSSPVTKSFNRGEC (SEQ ID NO: 44)
GCTAGCACCATGGGCTGGAGCTGCATCATCCTGTTCCTGGTGGCCA
CCGCCACCGGCGTGCACAGCGACATCGTGATGACCCAGGCCGCCCCCAG
CGTGGCCGTGACCCCCGGCGCCAGCGTGAGCATCAGCTGCCGCAGCAGC
AAGAGCCTGCTGCACAGCAGCGGCAAGACCTACCTGTACTGGTTCCTGC
AGCGCCCCGGCCAGAGCCCCCAGCTGCTGATCTACCGCCTGAGCAGCCT
GGCCAGCGGCGTGCCCGACCGCTTCAGCGGCAGCGGCAGCGGCACCGCC
TTCACCCTGCGCATCAGCCGCGTGGAGGCCGAGGACGTGGGCGTGTACT
ACTGCATGCAGCACCTGGAGTACCCCTACACCTTCGGCGGCGGCACCAA
GCTGGAGATCAAGCGTACGGTGGCCGCTCCTTCCGTGTTCATCTTCCCT
CCCTCCGACGAGCAGCTGAAGTCCGGCACCGCCTCCGTGGTGTGTCTGC
TGAACAACTTCTACCCTCGGGAGGCCAAGGTGCAGTGGAAGGTGGACAA
CGCCCTGCAGTCCGGCAACTCCCAGGAGTCCGTCACCGAGCAGGACTCC
AAGGACAGCACCTACTCCCTGTCCTCCACCCTGACCCTGTCCAAGGCCG
ACTACGAGAAGCACAAGGTGTACGCCTGTGAGGTGACCCACCAGGGCCT
GTCCAGCCCTGTGACCAAGTCCTTCAACCGGGGCGAGTGCTGAAGCTT

Humanized VH Sequences
HC1:
(SEQ ID NO: 45)
MGWSCIILFLVATATGVHSQVQLKESGPGLVAPSESLSITCTVSGFSLI
DYGVNWIRQPPGKGLEWLGVIWGDGTTYYNPSLKSRLSISKDNSKSQVF
LKVTSLTTDDTAMYYCARIVYWGQGTLVTVSAASTKGPSVFPLAPCSRS
TSESTAALGCLVKDYFPEPVTVSWNSGALTSGVHTFPAVLQSSGLYSLS
SVVTVPSSSLGTKTYTCNVDHKPSNTKVDKRVESKYGPPCPSCPAPEFL
GGPSVFLFPPKPKDTLMISRTPEVTCVVVDVSQEDPEVQFNWYVDGVEV
HNAKTKPREEQFNSTYRVVSVLTVLHQDWLNGKEYKCKVSNKGLPSSIE
KTISKAKGQPREPQVYTLPPSQEEMTKNQVSLTCLVKGFYPSDIAVEWE
SNGQPENNYKTTPPVLDSDGSFFLYSRLTVDKSRWQEGNVFSCSVMHEA
LHNHYTQKSLSLSLG (SEQ ID NO: 46)
GCTAGCACCATGGGCTGGAGCTGCATCATCCTGTTCCTGGTGGCCA
CCGCCACCGGCGTGCACAGCCAGGTGCAGCTGAAGGAGAGCGGCCCCGG
CCTGGTGGCCCCCAGCGAGAGCCTGAGCATCACCTGCACCGTGAGCGGC
TTCAGCCTGATCGACTACGGCGTGAACTGGATCCGCCAGCCCCCCGGCA
AGGGCCTGGAGTGGCTGGGCGTGATCTGGGGCGACGGCACCACCTACTA
CAACCCCAGCCTGAAGAGCCGCCTGAGCATCAGCAAGGACAACAGCAAG
AGCCAGGTGTTCCTGAAGGTGACCAGCCTGACCACCGACGACACCGCCA
TGTACTACTGCGCCCGCATCGTGTACTGGGGCCAGGGCACCCTGGTGAC
CGTGAGCGCCGCCAGCACCAAGGGCCCTTCCGTGTTCCCTCTGGCCCCT
TGCTCCCGGTCCACCTCCGAGTCCACCGCCGCTCTGGGCTGCCTGGTGA
AGGACTACTTCCCTGAGCCTGTGACCGTGTCCTGGAACTCTGGCGCCCT
GACCTCCGGCGTGCACACCTTCCCTGCCGTGCTGCAGTCCTCCGGCCTG
TACTCCCTGTCCTCCGTGGTGACCGTGCCTTCCTCCTCCCTGGGCACCA
AGACCTACACCTGTAACGTGGACCACAAGCCTTCCAACACCAAGGTGGA
CAAGCGGGTGGAGTCCAAGTACGGCCCTCCTTGCCCTTCCTGCCCTGCC
CCTGAGTTCCTGGGCGGACCTAGCGTGTTCCTGTTCCCTCCTAAGCCTA
AGGACACCCTGATGATCTCCCGGACCCCTGAGGTGACCTGTGTGGTGGT
GGACGTGTCCCAGGAGGACCCTGAGGTCCAGTTCAACTGGTACGTGGAC
GGCGTGGAGGTGCACAACGCCAAGACCAAGCCTCGGGAGGAGCAGTTCA
ATTCCACCTACCGGGTGGTGTCTGTGCTGACCGTGCTGCACCAGGACTG
GCTGAACGGCAAAGAATACAAGTGTAAGGTCTCCAACAAGGGCCTGCCC
TCCTCCATCGAGAAAACCATCTCCAAGGCCAAGGGCCAGCCTAGGGAGC
CTCAGGTGTACACCCTGCCTCCTAGCCAGGAAGAGATGACCAAGAACCA
GGTGTCCCTGACCTGTCTGGTGAAGGGCTTCTACCCTTCCGACATCGCC
GTGGAGTGGGAGTCCAACGGCCAGCCTGAGAACAACTACAAGACCACCC
CTCCTGTGCTGGACTCCGACGGCTCCTTCTTCCTGTACTCCAGGCTGAC

CGTGGACAAGTCCCGGTGGCAGGAGGGCAACGTCTTTTCCTGCTCCGTG

ATGCACGAGGCCCTGCACAACCACTACACCCAGAAGTCCCTGTCCCTGT

CTCTGGGCTGAAGCTT

HC2:

(SEQ ID NO: 47)
MGWSCIILFLVATATGVHSEVQLKESGPGLVAPGGSLSITCTVSGFSLI

DYGVNWIRQPPGKGLEWLGVIWGDGTTYYNAPLKGRLSISKDNSKSQVF

LQMNSLKTDDTAMYYCARIVYWGQGTLVTVSSASTKGPSVFPLAPCSRS

TSESTAALGCLVKDYFPEPVTVSWNSGALTSGVHTFPAVLQSSGLYSLS

SVVTVPSSSLGTKTYTCNVDHKPSNTKVDKRVESKYGPPCPSCPAPEFL

GGPSVFLFPPKPKDTLMISRTPEVTCVVVDVSQEDPEVQFNWYVDGVEV

HNAKTKPREEQFNSTYRVVSVLTVLHQDWLNGKEYKCKVSNKGLPSSIE

KTISKAKGQPREPQVYTLPPSQEEMTKNQVSLTCLVKGFYPSDIAVEWE

SNGQPENNYKTTPPVLDSDGSFFLYSRLTVDKSRWQEGNVFSCSVMHEA

LHNHYTQKSLSLSLG (SEQ ID NO: 48)
GCTAGCACCATGGGCTGGAGCTGCATCATCCTGTTCCTGGTGGCCA

CCGCCACCGGCGTGCACAGCGAGGTGCAGCTGAAGGAGAGCGGCCCCGG

CCTGGTGGCCCCCGGCGGCAGCCTGAGCATCACCTGCACCGTGAGCGGC

TTCAGCCTGATCGACTACGGCGTGAACTGGATCCGCCAGCCCCCCGGCA

AGGGCCTGGAGTGGCTGGGCGTGATCTGGGGCGACGGCACCACCTACTA

CAACGCCCCCCTGAAGGGCCGCCTGAGCATCAGCAAGGACAACAGCAAG

AGCCAGGTGTTCCTGCAGATGAACAGCCTGAAGACCGACGACACCGCA

TGTACTACTGCGCCCGCATCGTGTACTGGGGCCAGGGCACCCTGGTGAC

CGTGAGCAGCGCCAGCACCAAGGGCCCTTCCGTGTTCCCTCTGGCCCCT

TGCTCCCGGTCCACCTCCGAGTCCACCGCCGCTCTGGGCTGCCTGGTGA

AGGACTACTTCCCTGAGCCTGTGACCGTGTCCTGGAACTCTGGCGCCCT

GACCTCCGGCGTGCACACCTTCCCTGCCGTGCTGCAGTCCTCCGGCCTG

TACTCCCTGTCCTCCGTGGTGACCGTGCCTTCCTCCTCCCTGGGCACCA

AGACCTACACCTGTAACGTGGACCACAAGCCTTCCAACACCAAGGTGGA

CAAGCGGGTGGAGTCCAAGTACGGCCCTCCTTGCCCTTCCTGCCCTGCC

CCTGAGTTCCTGGGCGGACCTAGCGTGTTCCTGTTCCCTCCTAAGCCTA

AGGACACCCTGATGATCTCCCGGACCCCTGAGGTGACCTGTGTGGTGGT

GGACGTGTCCCAGGAGGACCCTGAGGTCCAGTTCAACTGGTACGTGGAC

GGCGTGGAGGTGCACAACGCCAAGACCAAGCCTCGGGAGGAGCAGTTCA

ATTCCACCTACCGGGTGGTGTCTGTGCTGACCGTGCTGCACCAGGACTG

GCTGAACGGCAAAGAATACAAGTGTAAGGTCTCCAACAAGGGCCTGCCC

TCCTCCATCGAGAAAACCATCTCCAAGGCCAAGGGCCAGCCTAGGGAGC

CTCAGGTGTACACCCTGCCTCCTAGCCAGGAAGAGATGACCAAGAACCA

GGTGTCCCTGACCTGTCTGGTGAAGGGCTTCTACCCTTCCGACATCGCC

GTGGAGTGGGAGTCCAACGGCCAGCCTGAGAACAACTACAAGACCACCC

CTCCTGTGCTGGACTCCGACGGCTCCTTCTTCCTGTACTCCAGGCTGAC

CGTGGACAAGTCCCGGTGGCAGGAGGGCAACGTCTTTTCCTGCTCCGTG

ATGCACGAGGCCCTGCACAACCACTACACCCAGAAGTCCCTGTCCCTGT

CTCTGGGCTGAAGCTT

Example 16

Humanization Based on Molecular Dynamic Trajectories

The $V_L$ and $V_H$ sequences of 16D7 were blasted in the protein data base (PDB) (Berman et al., Nucleic Acids Research, 2000, 28:235-242) and the closest homologues for the variable light chain are 1MH5, 1MJJ and 1MJU (J Mol Biol 332:423-435, 2003), with equivalent similarity scores. 1MJU was retained as a template because of high accuracy of the crystal structure, which had been determined up to 1.22 Å resolution. The closest homologue for the heavy chain was found to be 1FNS (Nat Struct Biol 7:881-884, 2000). The structures, 1MJU and 1FNS, were used to build up a homology model of the variable domains which was subsequently energy minimized using standard procedures.

A molecular dynamic (MD) simulation of the 3D homology model of 16D7 was subsequently performed for 1.1 nanosecond (ns) in Generalized Born implicit solvent (see Gallicchio & Levy, J Comput Chem 2004, 25:479-499). The MD simulation starts by an initialization of the velocities from a Gaussian distribution at 500 K, followed by an equilibration period of 200 picoseconds (ps). During the MD simulation, all bonds are constrained using the SHAKE algorithm (see Barth. et al., J Comp Chem, 1995, 16:1192-1209), the time step was 1 femtosecond (fs), and the simulation, based on the Veda integration algorithm, was run in the canonical NVT (number of particles, volume and temperature) ensemble at a temperature of 500 K. This simulation is done with harmonic constraints applied to the backbone atoms. Ten diverse conformations are extracted, one every 100 ps, during the last 1 ns of this first simulation.

These 10 diverse conformations are then used as 10 diverse starting points to run 10 molecular dynamic simulations, without constraints on the backbone, at a 300 K temperature for 2.3 ns in Generalized Born implicit solvent. Each MD simulation starts by an initialization of the velocities from a Gaussian distribution at 298.15 K, followed by an equilibration period of 300 ps. All bonds are constrained using the SHAKE algorithm (see Barth. et al., J Comp Chem, 1995, 16:1192-1209), the time step was 1 fs, and the simulation, based on the Verlet integration algorithm, was run in the canonical NVT (number of particles, volume and temperature) ensemble at a temperature of 298.15 K. During the production period, 2,000 snapshots were then stored, one every 1 ps. The Scientific Vector Language (SVL), available within the MOE molecular modeling environment, (Molecular Operating Environment (MOE), Chemical Computing Group, Quebec, Canada) was used to code the following post-treatment protocol.

First, each snapshot, N, was optimally superposed onto its predecessor, the snapshot N−1, to discard the overall rotational and translational motions which occur during the MD modeling and calculation. The superposition was obtained by minimizing the Root Mean Square Distance (RMSD) between all pairs of corresponding atoms from the two snapshots. Only the heavy atoms of the antibody backbone were considered in the superposition operation. Using the same superposition method, each snapshot then was superposed onto the medoïd snapshot. The medoïd snapshot is the antibody conformation with the Cartesian coordinates the closest from the average coordinates of all conformations. For each of the 10 MD simulations, the last 2,000 conformations are used to quantify, for each amino acid of the murine antibody, the deviation of the atomic positions with respect to a medoïd conformation of the amino-acid. For each of the antibody residue i, the RMSD between the heavy atoms of the conformation j and a medoïd reference conformation k were calculated. The RMSD has the following formula:

$$RMSDj = \sqrt{\frac{\sum_{l=1}^{m}(d_{lk})^2}{m}},$$

with $d_{lk}$ defined as the Euclidean distance expressed in Angstroms (Å) between the heavy atom l of the residue j and its counterpart of the medoïd reference conformation k. For the pair wise association of heavy atoms l, the symmetry of the side chain heavy atoms for the amino acids, Asp, Leu, Val, Glu, Arg, Phe and Tyr, also was considered. The reference conformation k varies from one residue to another, and corresponds to the medoïd conformation k with the closest Euclidean distance to the average coordinates of all conformations of the studied residue i.

The humanizing mutations are found by determining which human antibody germ line is the most similar to the murine antibody in terms of their most flexible amino acids. To do so, the motions of the 60 most flexible amino acids of the murine antibody, during the 20 ns (10×2 ns) of molecular dynamic simulation, are compared to the motions of the corresponding amino acids of 49 homology models of human antibody germ lines, for each of which 10 molecular dynamic simulations have been run using the same protocol. The 49 3D homology models of human antibody germ lines were built by systematically combining the 7 most frequent human light chain (vκ1, vκ2, vκ3, vκ4, vλ1, vλ2, vλ3) and the 7 most frequent heavy chains (vh1a, vh1b, vh2, vh3, vh4, vh5, vh6) (Nucleic Acids Research, 2005, Vol. 33, Database issue D593-D597).

The 60 most flexible amino acids exclude any amino acid in the CDR, and its immediate vicinity, i.e. amino acid with an α carbon at a distance of less than 5 Å to any α carbon of CDR amino acids as seen in the 3D homology model.

The flexibility is quantified by comparing the RMSD (Fi) of a given amino acid (i) to its medoïd conformation as defined previously, averaged over 10 molecular dynamic simulations, to the RMSD (Fm) of all amino acids of the murine antibody, averaged over the same 10 molecular dynamic simulations. An amino acid is considered flexible enough to potentially interact with the T-cell receptors, and trigger an immune-response, if the flexibility score Zi, defined as Zi=(Fi–Fm)/Fm, is above 0.15.

Using this molecular dynamic averaged flexibility estimation protocol, 23 amino acids have been considered as flexible in the variable region of the murine 16D7 antibody, excluding the CDR region and its immediate vicinity thereof.

The set of flexible residues for the light chain include the following residues (sequential numbering): R16, E17, R44, G46, Q47, S48, R79, R82, E84, E86, and E110; and for the heavy chain include the following residues: K5, P41, G42, K43, K64, R70, D72, N73, S74, Q75, Q86, and Q103.

The quadridimensional similarity of the murine antibody to the 49 human germ line homology models is quantified by sampling the positions of specific atoms of the 60 flexible amino acids, using all picosecond snapshots of the 10 molecular dynamic simulations, by means of a unique tridimensional cubic grid. This grid has a 1 Å resolution. The tridimensional grid is made of 445740 points and has been initialized using the tridimensional structure of a human antibody crystallographic model based on antibody, 8FAB (Biochem 30:3739-3748, 1991). The 8FAB model is also used to position all picosecond snapshot conformations of an antibody which are sampled in the tridimensional grid. For this purpose, the medoïd conformation of the molecular dynamic of the antibody is superposed onto the 8FAB model. This superposition consists of aligning the moments of inertia of the 2 models, followed by the minimization of the scalar distances between the α carbons of both models. All the remaining conformations of the molecular dynamic simulation are superposed onto the medoïd conformation using the same method.

Two types of sampling are done which result in two similarities (electrostatic similarity and lipophilic similarity), for a pair of antibodies being compared. These two similarities are then added to obtain the total similarity. The electrostatic sampling considers all atoms of the amino acid side chain. The value in one point, x, of the grid is obtained by applying a tridimensional Gaussian function f(x) weighted with the atomic partial charge as described in the Amber99 force field (Cieplak et al.; J. Comp. Chem. 2001, 22:1048-1057). The f(x) function is applied on the 3 Cartesian coordinate axis using the following formula:

$$f(x) = \left(s\sqrt{2\pi}\right)^{-3} \times \exp\left(\frac{-(x-u)^2}{2s^2}\right),$$

x and u being, respectively, the Cartesian coordinates of a grid point and a sampled amino-acid atom, and s=r/1.6 (r=covalence radius of the atom). The sampling is repeated for all conformations of the amino acid and the obtained results are averaged at all points of the tridimensional grid. The lipophilic sampling considers only the lipophilic atoms of the amino acid side-chain. The value at one point of the grid is calculated with the same Gaussian function f(x) without weighting. As a result, the two ensembles of picosecond snapshot conformations from the molecular dynamic simulations, of the two antibodies being compared are sampled by the same tridimensional grid. The electrostatic similarity (sim-elec), between antibody a and antibody b, can be calculated with the following formula:

$$sim-elec = \frac{\sum_{i=1}^{445740}(|x_i^a + x_i^b| - |x_i^a - x_i^b|)}{\sum_{i=1}^{445740}(|x_i^a + x_i^b|)}.$$

The lipophilic similarity is calculated with the same formula applied to the data generated by the lipophilic sampling previously described.

The human germ line model vλ2-vh4 displays the highest quadridimensional similarity (total similarity=50%) of its 60 most flexible amino acids with respect to the 60 most flexible amino acids of the murine antibody 16D7. The human germ line model vλ2-vh4 has thus been used to replace the murine antibody 16D7 flexible residues. Beforehand, the amino acids of the two sequences were aligned according to the optimal superposition of the α carbons of the corresponding 3D homology models. Unwanted motifs were searched for in the resulting humanized sequences using a blast search, as previously described in paragraph 41 above. In addition, known B-cell or T-cell epitopes were searched for in the resulting humanized sequences using the IEDB database as described in paragraph 44, supra.

The best sequence match in the IEDB for the light chain (LC7) was PGKAPQLLIYRMSNL (SEQ ID NO:52), which covers CDR2. The sequence exhibits 73% sequence identity with the peptide PGKAPKLLIYAASSL (SEQ ID NO:53) which shows binding to HLA-DRB1 0404* but has not been demonstrated to be immunogenic in man (J Immunol (1995) 155, 5655).

The best match in the IEDB for the heavy chain (HC4 and HC5) was SLIDYGVNWIRQPPG (SEQ ID NO:54) which covers CDR1 but has significant residue difference as typified by a 40% sequence identity obtained from a BLAST search within the IEDB database.

Two versions for the heavy chain (HC4 & HC5) and one version for the light chain (LC7) were obtained. Both versions of the heavy chain are derived from the human germ line model vλ2-vh4. HC5 is a variant of HC4 with an additional mutation to address a potential problematic residue: one potential deamidation site where the asparagine, N60, is changed into a proline residue.

Mutations introduced through the humanization of the variable chains are in lowercase and underlined and CDR's are underlined. The constant domains are not included.

LC7:
(SEQ ID NO: 55)
DIVMTQAAPSVAVTPqqSVSISCRSSKSLLHSSGKTYLYWFLQhPGkaP

QLLIYRMSNLASGVPDRFSGSGSGTAFTLtISqVqAEDVGVYYCMQHLE

YPYTFGGGTKLEIK

HC4:
(SEQ ID NO: 56)
QVQLqESGPGLVAPSQSLSITCTVSGFSLIDYGVNWIRQP

PGKGLEWLGVIWGDGTTYYNSALKSRLSIsKDtSkSQVFLKMNSLtTDD

TAMYYCARIVYWGQGTLVTVSAAK

HC5:
(SEQ ID NO: 57)
QVQLqESGPGLVAPSQSLSITCTVSGFSLIDYGVNWIRQP

PGKGLEWLGVIWGDGTTYYpSALKSRLSIsKDtSkSQVFLKMNSLtTD

DTAMYYCARIVYWGQGTLVTVSAAK

| Light Chain (Sequential numbering) | (LC7) |
|---|---|
| ARG16 | GLY |
| GLU17 | GLN |
| ARG44 | HIS |
| GLN47 | LYS |
| SER48 | ALA |
| ARG79 | THR |
| ARG82 | GLY |
| GLU84 | GLN |
| In total for VL | 8 mutations |

| Heavy Chain | (HC4) | (HC5) |
|---|---|---|
| LYS5 | GLN | GLN |
| ASN60 | ASN | PRO |
| ARG70 | SER | SER |
| ASN73 | THR | THR |
| GLN75 | LYS | LYS |
| GLN86 | THR | THR |
| In total for VH | 5 mutations | 6 mutations |

Example 17

Pharmacokinetics

The study is conducted with a suitable number of animals, (for example, 4 in a study; 2 for single dose and 2 for repeat dose, 5 doses weekly) healthy, purpose-bred male Cynomolgus monkeys weighing between 2.0 and 5.4 kg and ranging from 2 to 7 years of age. The animals can be allocated to two treatment groups, one receiving control IgG4 antibodies and one group receiving humanized 16D7. Monkeys in each group are administered a single intravenous bolus dose for example, 2.5-10 mg/kg in a dose volume of 2-3 mL/kg, or 5 weekly doses, i.v. Blood samples are collected at various time points after each dose administration and processed to plasma. The plasma samples are analyzed for concentration of total IgG4 and CXCR5 mAbs using an ELISA.

Example 18

Comparative Studies

Some of the instant antibodies were compared to commercially available antibodies in side-by-side experiments. MAB 190, available from R & D Systems, is a mouse mAb. RF82B is a rat anti-human CXCR5 available from BD. Clone 2C1 is a mouse mAb with a GST tag available from Abnova. The various humanized antibodies described herein were isotyped using reagents and methods known in the art. For example, those taught herein have a κ light chain, many are IgG1, while 46C9, 68D3 and H28 IgG2a. Most of the antibodies bind to the amino terminal end of CXCR5, and several of the antibodies compete with each other for binding to the same epitope or region.

The BD antibody binds poorly to human PBMCs.

While the antibodies generally did not bind to cynomolgus cells, 14C9, 19H5, H28, 54G6, 56H6 and 79B7 of the instant invention did.

16D7 was found to be of higher affinity, at least 10-fold, than the commercial antibodies, and has an off rate 100 times better than the other antibodies.

Example 19

Scale-Up

Each monoclonal antibody variant was produced in suspension-cultivated HEK293 FS™ cells by transient transfection of two expression plasmids encoding the heavy or the light chain complexed with 293Fectin™ (Invitrogen).

Secreted proteins were harvested eight days post-transfection and centrifuged. Proteins were purified by affinity chromatography on Protein A (ProSepvA, Millipore) after elution from the column with 25 mM citrate pH 3, 0.15 M NaCl buffer. The monoclonal antibodies were formulated in PBS and 0.22 μm filtered. Protein concentration was determined by measurement of absorbance at 280 nm. Each batch was analyzed by SDS-PAGE (Nupage Bistris/MES-SDS 10%) under reducing and non-reducing conditions to determine the purity and the molecular weight of each subunit and of the monomer. Each protein lot was also analyzed by gel filtration (Tricorn 10/300 GL Superdex 200) to determine the homogeneity of the monomer and the presence of high molecular weight species.

From 240 mL cultures, a total of 30 to 40 mg of eight 16D7 variant monoclonal antibodies was available and of appropriate quality for subsequent in vitro and in vivo tests.

Those skilled in the art will recognize, or be able to ascertain using no more than routine experimentation, many equivalents to the specific embodiments of the invention described herein. Such equivalents are intended to be encompassed by the following claims.

What is claimed:

1. A method of making a humanized antibody or fragment thereof, comprising:
   (a) identifying a human variable region homologous to a variable region of a non-human antibody;
   (b) building a homology model of the variable region of the non-human antibody using human variable region identified in step (a) and running molecular dynamic simulations to obtain molecular dynamic trajectory of the variable region of the non-human antibody;
   (c) analyzing the molecular dynamic trajectory of the variable region of the non-human antibody and determining amino acid flexibility scores to identify amino acids in the variable region of the non-human antibody which are flexible and amino acids that flank the flexible residue;
   (d) building homology models of human antibody germ lines and running molecular dynamic simulations to obtain molecular dynamic trajectories of the variable region of the human antibody germ lines;
   (e) analyzing the molecular dynamic trajectories of the variable region of the human antibody germ lines and determining amino acid flexibility scores to identify amino acids in the variable region of the human antibody germ lines which are flexible and amino acids that flank the flexible residue;
   (f) identifying the human variable region of the human antibody germ lines that displays molecular dynamic trajectory most similar to the molecular dynamic trajectory of the variable region of the non-human antibody and identifying humanizing mutations by comparing the flexibility scores for the most flexible amino acids of steps (c) and (e);
   (g) replacing the identified amino acids of step (c) with the identified amino acids of step (f) to produce a humanized variable region;
   (h) confirming that the humanized variable region of step (g) resembles a human antibody by comparing the humanized variable region molecular dynamic trajectory with the molecular dynamic trajectory of the variable region of the human antibody germ lines; and
   (i) recombinantly constructing a humanized variable region by joining the humanized variable region of step (g) with a human sequence to yield a humanized antibody or fragment thereof.

2. The method of claim 1, wherein step (g) comprises not replacing amino acids more than 5 Å from a complementarity determining region.

3. The method of claim 1, further comprising confirming that the humanized variable region of step (g) resembles a human antibody by comparing the humanized variable region sequence with the sequences of a collection of human antibody sequences.

4. The method of claim 1, wherein the humanized variable region of step (g) does not comprise a B cell epitope or a T cell epitope.

5. A method of making a humanized antibody or fragment thereof that specifically binds to the extracellular domain of human CXCR5, comprising:
   (a) identifying a human variable region homologous to a variable region of a non-human CXCR5 antibody;
   (b) building a homology model of the variable region of the non-human CXCR5 antibody using human variable region identified in step (a) and running molecular dynamic simulations to obtain molecular dynamic trajectory of the variable region of the non-human antibody;
   (c) analyzing the molecular dynamic trajectory of the variable region of the non-human antibody and determining amino acid flexibility scores to identify amino acids in the variable region of the non-human antibody which are flexible and amino acids that flank the flexible residue;
   (d) building homology models of human antibody germ lines and running molecular dynamic simulations to obtain molecular dynamic trajectories of the variable region of the human antibody germ lines;
   (e) analyzing the molecular dynamic trajectories of the variable region of the human antibody germ lines and determining amino acid flexibility scores to identify amino acids in the variable region of the human antibody germ lines which are flexible and amino acids that flank the flexible residue;
   (f) identifying the human variable region of the human antibody germ lines that displays molecular dynamic trajectory most similar to the molecular dynamic trajectory of the variable region of the non-human antibody and identifying humanizing mutations by comparing the flexibility scores for the most flexible amino acids of steps (c) and (e);
   (g) replacing the identified amino acids of step (c) with the identified amino acids of step (f) to produce a humanized variable region;
   h) confirming that the humanized variable region of step (g) resembles a human antibody by comparing the humanized variable region molecular dynamic trajectory with the molecular dynamic trajectory of the variable region of the human antibody germ lines; and
   (i) recombinantly constructing a humanized variable region by joining the humanized variable region of step (g) with a human sequence to yield a humanized antibody or fragment thereof that specifically binds to the extracellular domain of human CXCR5.

6. The method of claim 5, wherein step (g) comprises not replacing amino acids more than 5 Å from a complementarity determining region.

7. The method of claim 5, further comprising confirming that the humanized variable region of step (g) resembles a human antibody by comparing the humanized variable region sequence with the sequences of a collection of human antibody sequences.

8. The method of claim 5, wherein the humanized variable region of step (g) does not comprise a B cell epitope or a T cell epitope.

9. The method of claim 5, wherein the humanized antibody or fragment thereof comprises:
   (a) the amino acid sequences of RSSKSLLHSSGKTYLY (SEQ ID NO: 58), RMSNLAS (SEQ ID NO: 59), MQHLEYPYT (SEQ ID NO: 60), GFSLIDYGVN (SEQ ID NO: 61), VIWGDGTTY (SEQ ID NO: 62), and IVY (SEQ ID NO: 63);
   (b) a light chain variable domain comprising the amino acid sequence of SEQ ID NO: 13, SEQ ID NO: 14, or SEQ ID NO: 15, and a heavy chain variable domain comprising the amino acid sequence of SEQ ID NO: 16;
   (c) the amino acid sequences of RSSKSLLHSSGKTYLY (SEQ ID NO: 58), RLSNLAS (SEQ ID NO: 64), MQHLEYPYT (SEQ ID NO: 60), GFSLIDYGVN (SEQ ID NO: 61), VIWGDGTTY (SEQ ID NO: 62), and IVY (SEQ ID NO: 63);
   (d) the amino acid sequences of RSSKSLLHSSGKTYLY (SEQ ID NO: 58), RLSSNLAS (SEQ ID NO: 65), MQHLEYPYT (SEQ ID NO: 60), GFSLIDYGVN (SEQ ID NO: 61), VIWGDGTTY (SEQ ID NO: 62), and IVY (SEQ ID NO: 63);
   (e) a variable light chain (VL) comprising the amino acid sequence of SEQ ID NO: 17, SEQ ID NO: 19, or SEQ ID NO: 21, and a variable heavy chain (VH) comprising the amino acid sequence of SEQ ID NO: 23;
   (f) a variable light chain comprising the amino acid sequence of SEQ ID NO: 30, SEQ ID NO: 31, or SEQ ID NO: 32, and a variable heavy chain comprising the amino acid sequence of SEQ ID NO: 33 or SEQ ID NO: 34;
   (g) the amino acid sequences of RSSKSLLHSSGKTYLY (SEQ ID NO: 58), RMSNLA (SEQ ID NO: 66), MQHLEYPYT (SEQ ID NO: 60), GFSLIDYGVN (SEQ ID NO: 61), VIWGDGTTY (SEQ ID NO: 62), and IVY (SEQ ID NO: 63);
   (h) the amino acid sequences of RSSKSLLHSSGKTYLY (SEQ ID NO: 58), RLSNLA (SEQ ID NO: 67), MQHLEYPYT (SEQ ID NO: 60), GFSLIDYGVN (SEQ ID NO: 61), VIWGDGTTY (SEQ ID NO: 62), and IVY (SEQ ID NO: 63);
   (i) the amino acid sequences of RSSKSLLHSSGKTYLY (SEQ ID NO: 58), RLSSLA (SEQ ID NO: 68), MQHLEYPYT (SEQ ID NO: 60), GFSLIDYGVN (SEQ ID NO: 61), VIWGDGTTY (SEQ ID NO: 62), and IVY (SEQ ID NO: 63);
   (j) a variable light chain comprising the amino acid sequence of SEQ ID NO: 35, and a variable heavy chain comprising the amino acid sequence of SEQ ID NO: 37;
   (k) a variable light chain comprising the amino acid sequence of SEQ ID NO: 39, SEQ ID NO: 41, or SEQ ID NO: 43, and a variable heavy chain comprising the amino acid sequence of SEQ ID NO: 45 or SEQ ID NO: 47;
   (l) a variable light chain comprising the amino acid sequence of SEQ ID NO: 55, and a variable heavy chain comprising the amino acid sequence of SEQ ID NO: 56 or SEQ ID NO: 57; or
   (m) the amino acid sequences of RSSKSLLHSSGKTYLYW (SEQ ID NO: 69), RMSNLA (SEQ ID NO: 66), MQHLEYPYT (SEQ ID NO: 60), GFSLIDYGVN (SEQ ID NO: 61), VIWGDGTTY (SEQ ID NO: 62), and IVY (SEQ ID NO: 63).

10. The method of claim 5, wherein the humanized antibody or fragment thereof comprises a variable light chain comprising the amino acid sequence of SEQ ID NO: 32, and a variable heavy chain comprising the amino acid sequence of SEQ ID NO: 33.

11. The method of claim 5, wherein the humanized antibody or fragment thereof comprises the amino acid sequences of RSSKSLLHSSGKTYLY (SEQ ID NO: 58), RLSSLA (SEQ ID NO: 68), MQHLEYPYT (SEQ ID NO: 60), GFSLIDYGVN (SEQ ID NO: 61), VIWGDGTTY (SEQ ID NO: 62), and IVY (SEQ ID NO: 63).

* * * * *

UNITED STATES PATENT AND TRADEMARK OFFICE
CERTIFICATE OF CORRECTION

PATENT NO. : 9,175,087 B2
APPLICATION NO. : 13/794281
DATED : November 3, 2015
INVENTOR(S) : Renata Lee et al.

It is certified that error appears in the above-identified patent and that said Letters Patent is hereby corrected as shown below:

In the specification,

In column 3, line 59, delete "scF$_V$" and insert -- scF$_v$ --, therefor.

In column 9, line 28, delete "Chromatog" and insert -- (J Chromatog --, therefor.

In column 13, line 2, delete "an other" and insert -- another --, therefor.

In column 15, line 13, delete "reactionwith" and insert -- reaction with --, therefor.

In column 16, line 29, delete "No." and insert -- Nos. --, therefor.

In column 26, line 48, delete "F$_{(ac')2}$-SH" and insert -- F$_{(ab')2}$-SH --, therefor.

In column 27, line 15, delete "Ricchmann" and insert -- Riechmann --, therefor.

In column 29, line 57, delete "F$_v$" and insert -- F$_c$ --, therefor.

In column 29, line 61, delete "(Cuss" and insert -- (Guss --, therefor.

In column 36, line 23, delete "(Tnvitrogen," and insert -- (Invitrogen, --, therefor.

In column 39, line 48, delete "sacchardc" and insert -- saccharide --, therefor.

In column 46, line 6, delete "(TWEEN-20°, TWEEN-80°" and insert -- (TWEEN-20®, TWEEN-80® --, therefor.

In column 48, line 28, delete "sulthydryl" and insert -- sulfhydryl --, therefor.

In column 49, line 41, delete "pharmaceutics" and insert -- pharmaceutic --, therefor.

In column 55, line 20, delete "pcDNA3." and insert -- pCDNA3. --, therefor.

In column 55, line 34-35, delete "MAB 190" and insert -- MAB190 --, therefor.

In column 55, line 38, delete "scrum" and insert -- serum --, therefor.

In column 56, line 42, delete "Mabs" and insert -- mAbs --, therefor.

In column 58, line 47, delete "pcDNA3." and insert -- pCDNA3. --, therefor.

In column 58, line 50, delete "cDNA3." and insert -- CDNA3. --, therefor.

In column 58, line 53, delete "pcDNA3." and insert -- pCDNA3. --, therefor.

Signed and Sealed this
Fourteenth Day of June, 2016

Michelle K. Lee
*Director of the United States Patent and Trademark Office*

CERTIFICATE OF CORRECTION (continued)
U.S. Pat. No. 9,175,087 B2

In the specification,

In column 59, line 34, delete "MAB 190" and insert -- MAB190 --, therefor.

In column 62, line 64, delete "MAB 190)" and insert -- MAB190) --, therefor.

In column 65, line 10, delete "huCXCL 13" and insert -- huCXCL13 --, therefor.

In column 67, line 11, delete "137," and insert -- I37, --, therefor.

In column 72, line 11, delete "Lcu," and insert -- Leu, --, therefor.

In column 72, line 49, delete "in," and insert -- $m_i$ --, therefor.

In column 72, line 60, delete "5110," and insert -- S110, --, therefor.

In column 73, line 18, delete "TDDTAMYYCAR1" and insert -- TDDTAMYYCARI --, therefor.

In column 73, line 50, delete "Lcu" and insert -- Leu --, therefor.

In column 80, line 36, delete "Veda" and insert -- Verlet --, therefor.

In column 81, line 20, delete "l" and insert -- 1 --, therefor.

In column 81, line 22, delete "I," and insert -- 1, --, therefor.

In column 84, line 38-39, delete "MAB 190," and insert -- MAB190, --, therefor.

In column 84, line 67, delete "293Fectin™" and insert -- 293fectin™ --, therefor.

In column 85, line 8, delete "(Nupagc" and insert -- (Nupage --, therefor.

SEQUENCE LISTING

```
<160> NUMBER OF SEQ ID NOS: 69

<210> SEQ ID NO 1
<211> LENGTH: 36
<212> TYPE: PRT
<213> ORGANISM: Homo sapiens

<400> SEQUENCE: 1

Met Asn Tyr Pro Thr Leu Glu Met Asp Leu Glu Asn Leu Glu Asp Leu
1               5                   10                  15

Phe Trp Glu Leu Asp Arg Leu Asp Asn Tyr Asn Thr Ser Leu Val Glu
            20                  25                  30

Asn His Leu Cys
        35

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (18)..(18)
<223> OTHER INFORMATION: a, c, g or t
<220> FEATURE:
<221> NAME/KEY: misc_feature
<222> LOCATION: (18)..(18)
<223> OTHER INFORMATION: n is a, c, g, or t

<400> SEQUENCE: 2
cttccggaat tcsargtnma gctgsagsag tc                                   32

<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (18)..(18)
<223> OTHER INFORMATION: a, c, g or t
<220> FEATURE:
<221> NAME/KEY: misc_feature
<222> LOCATION: (18)..(18)
<223> OTHER INFORMATION: n is a, c, g, or t

<400> SEQUENCE: 3
cttccggaat tcsargtnma gctgsagsag tcwgg                                35

<210> SEQ ID NO 4
<211> LENGTH: 36
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggaggatcca tagacagatg ggggtgtcgt tttggc                                36

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggagctcgay attgtgmtsa cmcarwctmc a                                    31

<210> SEQ ID NO 6
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tatagagctc aagcttggat ggtgggaaga tggatacagt tggtgc                    46

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ccaagctgtg tcctrtcc                                                   18

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cgacaagtcg actagcccctt gaccaggcat cc                                  32

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
wtctctrgag tcagtggg                                                   18

<210> SEQ ID NO 10
<211> LENGTH: 32
<212> TYPE: DNA
```

<210> SEQ ID NO 11
<211> LENGTH: 112
<212> TYPE: PRT
<213> ORGANISM: Mus sp.

<400> SEQUENCE: 11

```
Asp Ile Val Met Thr Gln Ala Ala Pro Ser Val Ala Val Thr Pro Arg
1               5                   10                  15
Glu Ser Val Ser Ile Ser Cys Arg Ser Ser Lys Ser Leu Leu His Ser
            20                  25                  30
Ser Gly Lys Thr Tyr Leu Tyr Trp Phe Leu Gln Arg Pro Gly Gln Ser
        35                  40                  45
Pro Gln Leu Leu Ile Tyr Arg Met Ser Asn Leu Ala Ser Gly Val Pro
    50                  55                  60
Asp Arg Phe Ser Gly Ser Gly Ser Gly Thr Ala Phe Thr Leu Arg Ile
65                  70                  75                  80
Ser Arg Val Glu Ala Glu Asp Val Gly Val Tyr Tyr Cys Met Gln His
                85                  90                  95
Leu Glu Tyr Pro Tyr Thr Phe Gly Gly Gly Thr Lys Leu Glu Ile Lys
            100                 105                 110
```

<210> SEQ ID NO 12
<211> LENGTH: 111
<212> TYPE: PRT
<213> ORGANISM: Mus sp.

<400> SEQUENCE: 12

```
Gln Val Gln Leu Lys Glu Ser Gly Pro Gly Leu Val Ala Pro Ser Gln
1               5                   10                  15
Ser Leu Ser Ile Thr Cys Thr Val Ser Gly Phe Ser Leu Ile Asp Tyr
            20                  25                  30
Gly Val Asn Trp Ile Arg Gln Pro Pro Gly Lys Gly Leu Glu Trp Leu
        35                  40                  45
Gly Val Ile Trp Gly Asp Gly Thr Thr Tyr Tyr Asn Ser Ala Leu Lys
    50                  55                  60
Ser Arg Leu Ser Ile Arg Lys Asp Asn Ser Gln Ser Gln Val Phe Leu
65                  70                  75                  80
Lys Met Asn Ser Leu Gln Thr Asp Asp Thr Ala Met Tyr Tyr Cys Ala
                85                  90                  95
Arg Ile Val Tyr Trp Gly Gln Gly Thr Leu Val Thr Val Ser Ala
            100                 105                 110
```

<210> SEQ ID NO 13
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 13

```
Asp Ile Val Met Thr Gln Ser Ala Leu Ser Val Ala Val Thr Pro Gly
```

```
  1               5                  10                 15
Glu Ser Val Ser Ile Ser Cys Arg Ser Ser Lys Ser Leu Leu His Ser
                20                  25                 30

Ser Gly Lys Thr Tyr Leu Tyr Trp Phe Leu Gln Arg Pro Gly Gln Ser
            35                  40                  45

Pro Gln Leu Leu Ile Tyr Arg Met Ser Asn Leu Ala Ser Gly Val Pro
        50                  55                  60

Asp Arg Phe Ser Gly Ser Gly Ser Gly Thr Ala Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Lys Leu Glu Ile Lys
                100                 105                 110
```

<210> SEQ ID NO 14
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Asp Ile Val Met Thr Gln Ser Ala Leu Ser Val Ala Val Thr Pro Gly
1               5                  10                  15

Glu Ser Val Ser Ile Ser Cys Arg Ser Ser Lys Ser Leu Leu His Ser
                20                  25                  30

Ser Gly Lys Thr Tyr Leu Tyr Trp Phe Leu Gln Arg Pro Gly Gln Ser
            35                  40                  45

Pro Gln Leu Leu Ile Tyr Arg Leu Ser Asn Leu Ala Ser Gly Val Pro
        50                  55                  60

Asp Arg Phe Ser Gly Ser Gly Ser Gly Thr Ala Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Lys Leu Glu Ile Lys
                100                 105                 110
```

<210> SEQ ID NO 15
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

```
Asp Ile Val Met Thr Gln Ser Ala Leu Ser Val Ala Val Thr Pro Gly
1               5                  10                  15

Glu Ser Val Ser Ile Ser Cys Arg Ser Ser Lys Ser Leu Leu His Ser
                20                  25                  30

Ser Gly Lys Thr Tyr Leu Tyr Trp Phe Leu Gln Arg Pro Gly Gln Ser
            35                  40                  45

Pro Gln Leu Leu Ile Tyr Arg Leu Ser Ser Asn Leu Ala Ser Gly Val
        50                  55                  60

Pro Asp Arg Phe Ser Gly Ser Gly Ser Gly Thr Ala Phe Thr Leu Lys
65                  70                  75                  80

Ile Ser Arg Val Glu Ala Glu Asp Val Gly Val Tyr Tyr Cys Met Gln
```

His Leu Glu Tyr Pro Tyr Thr Phe Gly Gly Gly Thr Lys Leu Glu Ile
                 100                 105                 110

Lys

<210> SEQ ID NO 16
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Gln Leu Gln Glu Ser Gly Pro Gly Leu Val Ala Pro Ser Glu
1               5                   10                  15

Ser Leu Ser Ile Thr Cys Thr Val Ser Gly Phe Ser Leu Ile Asp Tyr
            20                  25                  30

Gly Val Asn Trp Ile Arg Gln Pro Pro Gly Lys Gly Leu Glu Trp Leu
        35                  40                  45

Gly Val Ile Trp Gly Asp Gly Thr Thr Tyr Tyr Asn Pro Ser Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Thr Ala Ala Asp Thr Ala Met Tyr Tyr Cys Ala
                85                  90                  95

Arg Ile Val Tyr Trp Gly Gln Gly Thr Leu Val Thr Val Ser Ser
            100                 105                 110

<210> SEQ ID NO 17
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Gly Trp Ser Cys Ile Ile Leu Phe Leu Val Ala Thr Ala Thr Gly
1               5                   10                  15

Val His Ser Asp Ile Val Met Thr Gln Ser Ala Leu Ser Val Ala Val
            20                  25                  30

Thr Pro Gly Glu Ser Val Ser Ile Ser Cys Arg Ser Ser Lys Ser Leu
        35                  40                  45

Leu His Ser Ser Gly Lys Thr Tyr Leu Tyr Trp Phe Leu Gln Arg Pro
    50                  55                  60

Gly Gln Ser Pro Gln Leu Leu Ile Tyr Arg Met Ser Asn Leu Ala Ser
65                  70                  75                  80

Gly Val Pro Asp Arg Phe Ser Gly Ser Gly Ser Gly Thr Ala Phe Thr
                85                  90                  95

Leu Lys Ile Ser Arg Val Glu Ala Glu Asp Val Gly Val Tyr Tyr Cys
            100                 105                 110

Met Gln His Leu Glu Tyr Pro Tyr Thr Phe Gly Gly Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 18
<211> LENGTH: 731
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
gctagcacca tgggctggag ctgcatcatc ctgttcctgg tggccaccgc caccggcgtg    60
cacagcgaca tcgtgatgac ccagagcgcc ctcagcgtgg ccgtgacccc cggcgagagc   120
gtgagcatca gctgccgcag cagcaagagc ctgctgcaca gcagcggcaa gacctacctg   180
tactggttcc tgcagcgccc cggccagagc ccccagctgc tgatctaccg catgagcaac   240
ctggccagcg gcgtgcccga ccgcttcagc ggcagcggca gcggcaccgc cttcaccctg   300
aagatcagcc gcgtggaggc cgaggacgtg ggcgtgtact actgcatgca gcacctggag   360 taccccctaca ccttcggcgg cggcaccaag ctggagatca gcgtacggt ggccgctcct   420 tccgtgttca tcttccctcc ctccgacgag cagctgaagt ccggcaccgc ctccgtggtg   480
tgtctgctga caacttcta ccctcgggag gccaaggtgc agtggaaggt ggacaacgcc   540
ctgcagtccg gcaactccca ggagtccgtc accgagcagg actccaagga cagcacctac   600
tccctgtcct ccaccctgac cctgtccaag gccgactacg agaagcacaa ggtgtacgcc   660
tgtgaggtga cccaccaggg cctgtccagc cctgtgacca gtccttcaa ccggggcgag   720 tgctgaagct t                                                        731

<210> SEQ ID NO 19
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Gly Trp Ser Cys Ile Ile Leu Phe Leu Val Ala Thr Ala Thr Gly
1               5                   10                  15

Val His Ser Asp Ile Val Met Thr Gln Ser Ala Leu Ser Val Ala Val
            20                  25                  30

Thr Pro Gly Glu Ser Val Ser Ile Ser Cys Arg Ser Ser Lys Ser Leu
        35                  40                  45

Leu His Ser Ser Gly Lys Thr Tyr Leu Tyr Trp Phe Leu Gln Arg Pro
    50                  55                  60

Gly Gln Ser Pro Gln Leu Leu Ile Tyr Arg Leu Ser Asn Leu Ala Ser
65                  70                  75                  80

Gly Val Pro Asp Arg Phe Ser Gly Ser Ser Gly Thr Ala Phe Thr
                85                  90                  95

Leu Lys Ile Ser Arg Val Glu Ala Glu Asp Val Gly Val Tyr Tyr Cys
            100                 105                 110

Met Gln His Leu Glu Tyr Pro Tyr Thr Phe Gly Gly Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 20
<211> LENGTH: 731
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
gctagcacca tgggctggag ctgcatcatc ctgttcctgg tggccaccgc caccggcgtg    60
cacagcgaca tcgtgatgac ccagagcgcc ctcagcgtgg ccgtgacccc cggcgagagc   120
gtgagcatca gctgccgcag cagcaagagc ctgctgcaca gcagcggcaa gacctacctg   180
tactggttcc tgcagcgccc cggccagagc ccccagctgc tgatctaccg cctgagcaac   240
ctggccagcg gcgtgcccga ccgcttcagc ggcagcggca gcggcaccgc cttcaccctg   300
aagatcagcc gcgtggaggc cgaggacgtg ggcgtgtact actgcatgca gcacctggag   360 taccccctaca ccttcggcgg cggcaccaag ctggagatca gcgtacggt ggccgctcct   420 tccgtgttca tcttccctcc ctccgacgag cagctgaagt ccggcaccgc ctccgtggtg   480
tgtctgctga caacttcta ccctcgggag gccaaggtgc agtggaaggt ggacaacgcc   540
ctgcagtccg gcaactccca ggagtccgtc accgagcagg actccaagga cagcacctac   600
tccctgtcct ccaccctgac cctgtccaag gccgactacg agaagcacaa ggtgtacgcc   660
tgtgaggtga cccaccaggg cctgtccagc cctgtgacca gtccttcaa ccggggcgag   720 tgctgaagct t                                                         731

<210> SEQ ID NO 21
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Gly Trp Ser Cys Ile Ile Leu Phe Leu Val Ala Thr Ala Thr Gly

```
            1               5                  10                 15
Val His Ser Asp Ile Val Met Thr Gln Ser Ala Leu Ser Val Ala Val
                20                  25                 30
Thr Pro Gly Glu Ser Val Ser Ile Ser Cys Arg Ser Ser Lys Ser Leu
                35                  40                 45
Leu His Ser Ser Gly Lys Thr Tyr Leu Tyr Trp Phe Leu Gln Arg Pro
                50                  55                 60
Gly Gln Ser Pro Gln Leu Leu Ile Tyr Arg Leu Ser Ser Leu Ala Ser
 65                 70                  75                 80
Gly Val Pro Asp Arg Phe Ser Gly Ser Gly Ser Gly Thr Ala Phe Thr
                85                  90                 95
Leu Lys Ile Ser Arg Val Glu Ala Glu Asp Val Gly Val Tyr Tyr Cys
                100                 105                110
Met Gln His Leu Glu Tyr Pro Tyr Thr Phe Gly Gly Gly Thr Lys Leu
                115                 120                125
Glu Ile Lys Arg Thr Val Ala Ala Pro Ser Val Phe Ile Phe Pro Pro
                130                 135                140
Ser Asp Glu Gln Leu Lys Ser Gly Thr Ala Ser Val Val Cys Leu Leu
145                 150                 155                160
Asn Asn Phe Tyr Pro Arg Glu Ala Lys Val Gln Trp Lys Val Asp Asn
                165                 170                175
Ala Leu Gln Ser Gly Asn Ser Gln Glu Ser Val Thr Glu Gln Asp Ser
                180                 185                190
Lys Asp Ser Thr Tyr Ser Leu Ser Ser Thr Leu Thr Leu Ser Lys Ala
                195                 200                205
Asp Tyr Glu Lys His Lys Val Tyr Ala Cys Glu Val Thr His Gln Gly
                210                 215                220
Leu Ser Ser Pro Val Thr Lys Ser Phe Asn Arg Gly Glu Cys
225                 230                 235

<210> SEQ ID NO 22
<211> LENGTH: 731
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
gctagcacca tgggctggag ctgcatcatc ctgttcctgg tggccaccgc caccggcgtg    60
cacagcgaca tcgtgatgac ccagagcgcc ctcagcgtgg ccgtgacccc cggcgagagc   120
gtgagcatca gctgccgcag cagcaagagc ctgctgcaca gcagcggcaa gacctacctg   180
tactggttcc tgcagcgccc cggccagagc ccccagctgc tgatctaccg cctgagcagc   240
ctggccagcg gcgtgcccga ccgcttcagc ggcagcggca gcggcaccgc cttcaccctg   300
aagatcagcc gcgtggaggc cgaggacgtg ggcgtgtact actgcatgca gcacctggag   360 taccccctaca ccttcggcgg cggcaccaag ctggagatca agcgtacggt ggccgctcct   420
tccgtgttca tcttccctcc ctccgacgag cagctgaagt ccggcaccgc ctccgtggtg   480
tgtctgctga acaacttcta ccctcgggag gccaaggtgc agtggaaggt ggacaacgcc   540
ctgcagtccg gcaactccca ggagtccgtc accgagcagg actccaagga cagcacctac   600
tccctgtcct ccaccctgac cctgtccaag gccgactacg agaagcacaa ggtgtacgcc   660
```

-continued

```
tgtgaggtga cccaccaggg cctgtccagc cctgtgacca agtccttcaa ccggggcgag    720
tgctgaagct t                                                         731
```

<210> SEQ ID NO 23
<211> LENGTH: 456
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

```
Met Gly Trp Ser Cys Ile Ile Leu Phe Leu Val Ala Thr Ala Thr Gly
1               5                   10                  15

Val His Ser Gln Val Gln Leu Gln Glu Ser Gly Pro Gly Leu Val Ala
            20                  25                  30

Pro Ser Glu Ser Leu Ser Ile Thr Cys Thr Val Ser Gly Phe Ser Leu
        35                  40                  45

Ile Asp Tyr Gly Val Asn Trp Ile Arg Gln Pro Pro Gly Lys Gly Leu
    50                  55                  60

Glu Trp Leu Gly Val Ile Trp Gly Asp Gly Thr Thr Tyr Tyr Asn Pro
65                  70                  75                  80

Ser Leu Lys Ser Arg Leu Ser Ile Ser Lys Asp Asn Ser Lys Ser Gln
                85                  90                  95

Val Phe Leu Lys Met Asn Ser Leu Thr Ala Ala Asp Thr Ala Met Tyr
            100                 105                 110

Tyr Cys Ala Arg Ile Val Tyr Trp Gly Gln Gly Thr Leu Val Thr Val
        115                 120                 125

Ser Ser Ala Ser Thr Lys Gly Pro Ser Val Phe Pro Leu Ala Pro Cys
    130                 135                 140

Ser Arg Ser Thr Ser Glu Ser Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Lys Thr Tyr Thr Cys Asn Val Asp His Lys Pro Ser Asn Thr Lys Val
    210                 215                 220

Asp Lys Arg Val Glu Ser Lys Tyr Gly Pro Pro Cys Pro Ser Cys Pro
225                 230                 235                 240

Ala Pro Glu Phe Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser Gln Glu Asp Pro Glu Val Gln Phe Asn Trp Tyr
        275                 280                 285

Val Asp Gly Val Glu Val His Asn Ala Lys Thr Lys Pro Arg Glu Glu
    290                 295                 300

Gln Phe Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Gly Leu Pro Ser Ser Ile Glu Lys Thr Ile Ser Lys Ala Lys Gly Gln
```

340                 345                 350
Pro Arg Glu Pro Gln Val Tyr Thr Leu Pro Pro Ser Gln Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Arg Leu Thr Val Asp Lys Ser Arg Trp Gln Glu Gly Asn Val
            420                 425                 430

Phe Ser Cys Ser Val Met His Glu Ala Leu His Asn His Tyr Thr Gln
        435                 440                 445

Lys Ser Leu Ser Leu Ser Leu Gly
    450                 455

<210> SEQ ID NO 24
<211> LENGTH: 1385
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
gctagcacca tgggctggag ctgcatcatc ctgttcctgg tggccaccgc caccggcgtg      60
cacagccagg tgcagctgca ggagagcggc cccggcctgg tgcccccag cgagagcctg     120 agcatcacct gcaccgtgag cggcttcagc ctgatcgact acggcgtgaa ctggatccgc     180
cagccccccg gcaagggcct ggagtggctg gcgtgatct ggggcgacgg caccacctac     240
tacaacccca gcctgaagag ccgcctgagc atctccaagg acaacagcaa gagccaggtg     300
ttcctgaaga tgaacagcct gaccgccgcc gacaccgcca tgtactactg cgcccgcatc     360
gtgtactggg gccagggcac cctggtgacc gtgagcagcg ccagcaccaa gggcccttcc     420
gtgttccctc tggccccttg ctcccggtcc acctccgagt ccaccgccgc tctgggctgc     480
ctggtgaagg actacttccc tgagcctgtg accgtgtcct ggaactctgg cgccctgacc     540
tccggcgtgc acaccttccc tgccgtgctg cagtcctccg gcctgtactc cctgtcctcc     600
gtggtgaccg tgccttcctc ctccctgggc accaagacct acacctgtaa cgtggaccac     660
aagccttcca acaccaaggt ggacaagcgg gtggagtcca agtacggccc tccttgccct     720
tcctgccctg cccctgagtt cctgggcgga cctagcgtgt tcctgttccc tcctaagcct     780
aaggacaccc tgatgatctc ccggacccct gaggtgacct gtgtggtggt ggacgtgtcc     840
caggaggacc ctgaggtcca gttcaactgg tacgtggacg gcgtggaggt gcacaacgcc     900
aagaccaagc ctcgggagga gcagttcaat tccacctacc gggtggtgtc tgtgctgacc     960
gtgctgcacc aggactggct gaacggcaaa gaatacaagt gtaaggtctc caacaagggc    1020
ctgccctcct ccatcgagaa aaccatctcc aaggccaagg gccagcctag ggagcctcag    1080
gtgtacaccc tgcctcctag ccaggaagag atgaccaaga accaggtgtc cctgacctgt    1140
ctggtgaagg gcttctaccc ttccgacatc gccgtggagt gggagtccaa cggccagcct    1200
gagaacaact acaagaccac ccctcctgtg ctggactccg acggctcctt cttcctgtac    1260
tccaggctga ccgtggacaa gtcccggtgg caggagggca acgtcttttc ctgctccgtg    1320

```
atgcacgagg ccctgcacaa ccactacacc cagaagtccc tgtccctgtc tctgggctga    1380
agctt                                                                 1385
```

<210> SEQ ID NO 25
<211> LENGTH: 22
<212> TYPE: PRT
<213> ORGANISM: Homo sapiens

<400> SEQUENCE: 25

```
Lys Pro Gly Gln Pro Pro Arg Leu Leu Ile Tyr Asp Ala Ser Asn Arg
1               5                   10                  15

Ala Thr Gly Ile Pro Ala
            20
```

<210> SEQ ID NO 26
<211> LENGTH: 12
<212> TYPE: PRT
<213> ORGANISM: Mus musculus

<400> SEQUENCE: 26

```
Thr Asp Asp Thr Ala Met Tyr Tyr Cys Ala Arg Ile
1               5                   10
```

<210> SEQ ID NO 27
<211> LENGTH: 12
<212> TYPE: PRT
<213> ORGANISM: Homo sapiens

<400> SEQUENCE: 27

```
Ser Glu Asp Ser Ala Leu Tyr Tyr Cys Ala Arg Asp
1               5                   10
```

<210> SEQ ID NO 28
<211> LENGTH: 112
<212> TYPE: PRT
<213> ORGANISM: Mus musculus

<400> SEQUENCE: 28

```
Asp Ile Val Met Thr Gln Ala Ala Pro Ser Val Ala Val Thr Pro Arg
1               5                   10                  15

Glu Ser Val Ser Ile Ser Cys Arg Ser Ser Lys Ser Leu Leu His Ser
            20                  25                  30

Ser Gly Lys Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Lys Leu Glu Ile Lys
            100                 105                 110
```

<210> SEQ ID NO 29
<211> LENGTH: 111
<212> TYPE: PRT
<213> ORGANISM: Mus musculus

<400> SEQUENCE: 29

```
Gln Val Gln Leu Lys Glu Ser Gly Pro Gly Leu Val Ala Pro Ser Gln
1               5                   10                  15
```

```
Ser Leu Ser Ile Thr Cys Thr Val Ser Gly Phe Ser Leu Ile Asp Tyr
            20                  25                  30

Gly Val Asn Trp Ile Arg Gln Pro Gly Lys Gly Leu Glu Trp Leu
        35                  40                  45

Gly Val Ile Trp Gly Asp Gly Thr Thr Tyr Tyr Asn Ser Ala Leu Lys
 50                  55                  60

Ser Arg Leu Ser Ile Arg Lys Asp Asn Ser Gln Ser Gln Val Phe Leu
 65                  70                  75                  80

Lys Met Asn Ser Leu Gln Thr Asp Asp Thr Ala Met Tyr Tyr Cys Ala
                 85                  90                  95

Arg Ile Val Tyr Trp Gly Gln Gly Thr Leu Val Thr Val Ser Ala
            100                 105                 110
```

<210> SEQ ID NO 30
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

```
Asp Ile Val Met Thr Gln Ala Ala Pro Ser Val Ala Val Thr Pro Gly
 1               5                   10                  15

Ala Ser Val Ser Ile Ser Cys Arg Ser Ser Lys Ser Leu Leu His Ser
            20                  25                  30

Ser Gly Lys Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
 50                  55                  60

Asp Arg Phe Ser Gly Ser Gly Ser Gly Thr Ala Phe Thr Leu Arg Ile
 65                  70                  75                  80

Ser Arg Val Glu Ala Glu Asp Val Gly Val Tyr Tyr Cys Met Gln His
                 85                  90                  95

Leu Glu Tyr Pro Tyr Thr Phe Gly Gly Gly Thr Lys Leu Glu Ile Lys
            100                 105                 110
```

<210> SEQ ID NO 31
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

```
Asp Ile Val Met Thr Gln Ala Ala Pro Ser Val Ala Val Thr Pro Gly
 1               5                   10                  15

Ala Ser Val Ser Ile Ser Cys Arg Ser Ser Lys Ser Leu Leu His Ser
            20                  25                  30

Ser Gly Lys Thr Tyr Leu Tyr Trp Phe Leu Gln Arg Pro Gly Gln Ser
        35                  40                  45

Pro Gln Leu Leu Ile Tyr Arg Leu Ser Asn Leu Ala Ser Gly Val Pro
 50                  55                  60

Asp Arg Phe Ser Gly Ser Gly Ser Gly Thr Ala Phe Thr Leu Arg Ile
 65                  70                  75                  80

Ser Arg Val Glu Ala Glu Asp Val Gly Val Tyr Tyr Cys Met Gln His
                 85                  90                  95
```

```
Leu Glu Tyr Pro Tyr Thr Phe Gly Gly Gly Thr Lys Leu Glu Ile Lys
            100                 105                 110
```

<210> SEQ ID NO 32
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

```
Asp Ile Val Met Thr Gln Ala Ala Pro Ser Val Ala Val Thr Pro Gly
1               5                   10                  15

Ala Ser Val Ser Ile Ser Cys Arg Ser Ser Lys Ser Leu Leu His Ser
            20                  25                  30

Ser Gly Lys Thr Tyr Leu Tyr Trp Phe Leu Gln Arg Pro Gly Gln Ser
        35                  40                  45

Pro Gln Leu Leu Ile Tyr Arg Leu Ser Ser Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Lys Leu Glu Ile Lys
            100                 105                 110
```

<210> SEQ ID NO 33
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

```
Gln Val Gln Leu Lys Glu Ser Gly Pro Gly Leu Val Ala Pro Ser Glu
1               5                   10                  15

Ser Leu Ser Ile Thr Cys Thr Val Ser Gly Phe Ser Leu Ile Asp Tyr
            20                  25                  30

Gly Val Asn Trp Ile Arg Gln Pro Pro Gly Lys Gly Leu Glu Trp Leu
        35                  40                  45

Gly Val Ile Trp Gly Asp Gly Thr Thr Tyr Tyr Asn Pro Ser Leu Lys
    50                  55                  60

Ser Arg Leu Ser Ile Ser Lys Asp Asn Ser Lys Ser Gln Val Phe Leu
65                  70                  75                  80

Lys Val Thr Ser Leu Thr Thr Asp Thr Ala Met Tyr Tyr Cys Ala
                85                  90                  95

Arg Ile Val Tyr Trp Gly Gln Gly Thr Leu Val Thr Val Ser Ala
            100                 105                 110
```

<210> SEQ ID NO 34
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

```
Glu Val Gln Leu Lys Glu Ser Gly Pro Gly Leu Val Ala Pro Gly Gly
1               5                   10                  15

Ser Leu Ser Ile Thr Cys Thr Val Ser Gly Phe Ser Leu Ile Asp Tyr
            20                  25                  30

Gly Val Asn Trp Ile Arg Gln Pro Pro Gly Lys Gly Leu Glu Trp Leu
            35                  40                  45

Gly Val Ile Trp Gly Asp Gly Thr Thr Tyr Tyr Asn Ala Pro Leu Lys
    50                  55                  60

Gly Arg Leu Ser Ile Ser Lys Asp Asn Ser Lys Ser Gln Val Phe Leu
65                  70                  75                  80

Gln Met Asn Ser Leu Lys Thr Asp Asp Thr Ala Met Tyr Tyr Cys Ala
                85                  90                  95

Arg Ile Val Tyr Trp Gly Gln Gly Thr Leu Val Thr Val Ser Ser
            100                 105                 110
```

<210> SEQ ID NO 35
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

```
Met Gly Trp Ser Cys Ile Ile Leu Phe Leu Val Ala Thr Ala Thr Gly
1               5                   10                  15

Val His Ser Asp Ile Val Met Thr Gln Ala Ala Pro Ser Val Ala Val
            20                  25                  30

Thr Pro Arg Glu Ser Val Ser Ile Ser Cys Arg Ser Ser Lys Ser Leu
            35                  40                  45

Leu His Ser Ser Gly Lys Thr Tyr Leu Tyr Trp Phe Leu Gln Arg Pro
            50                  55                  60

Gly Gln Ser Pro Gln Leu Leu Ile Tyr Arg Met Ser Asn Leu Ala Ser
65                  70                  75                  80

Gly Val Pro Asp Arg Phe Ser Gly Ser Gly Ser Gly Thr Ala Phe Thr
                85                  90                  95

Leu Arg Ile Ser Arg Val Glu Ala Glu Asp Val Gly Val Tyr Tyr Cys
            100                 105                 110

Met Gln His Leu Glu Tyr Pro Tyr Thr Phe Gly Gly Gly Thr Lys Leu
            115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
            195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

<210> SEQ ID NO 36

-continued

```
<211> LENGTH: 731
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
gctagcacca tgggctggag ctgcatcatc ctgttcctgg tggccaccgc caccggcgtg     60
cacagcgaca tcgtgatgac ccaggccgcc cccagcgtgg ccgtgacccc cgcgagagc    120 gtgagcatca gctgccgcag cagcaagagc ctgctgcaca gcagcggcaa gacctacctg    180
tactggttcc tgcagcgccc cggccagagc ccccagctgc tgatctaccg catgagcaac    240
ctggccagcg gcgtgcccga ccgcttcagc ggcagcggca gcggcaccgc cttcaccctg    300
cgcatcagcc gcgtggaggc cgaggacgtg ggcgtgtact actgcatgca gcacctggag    360
tacccctaca ccttcggcgg cggcaccaag ctggagatca gcgtacggt ggccgctcct    420 tccgtgttca tcttccctcc ctccgacgag cagctgaagt ccggcaccgc ctccgtggtg    480
tgtctgctga caacttcta ccctcgggag gccaaggtgc agtggaaggt ggacaacgcc    540
ctgcagtccg gcaactccca ggagtccgtc accgagcagg actccaagga cagcacctac    600
tccctgtcct ccaccctgac cctgtccaag gccgactacg agaagcacaa ggtgtacgcc    660
tgtgaggtga cccaccaggg cctgtccagc cctgtgacca gtccttcaa ccggggcgag    720 tgctgaagct t                                                          731

<210> SEQ ID NO 37
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Met Gly Trp Ser Cys Ile Ile Leu Phe Leu Val Ala Thr Ala Thr Gly
1               5                   10                  15

Val His Ser Gln Val Gln Leu Lys Glu Ser Gly Pro Gly Leu Val Ala
            20                  25                  30

Pro Ser Gln Ser Leu Ser Ile Thr Cys Thr Val Ser Gly Phe Ser Leu
        35                  40                  45

Ile Asp Tyr Gly Val Asn Trp Ile Arg Gln Pro Pro Gly Lys Gly Leu
    50                  55                  60

Glu Trp Leu Gly Val Ile Trp Gly Asp Gly Thr Thr Tyr Tyr Asn Ser
65                  70                  75                  80

Ala Leu Lys Ser Arg Leu Ser Ile Arg Lys Asp Asn Ser Gln Ser Gln
                85                  90                  95

Val Phe Leu Lys Met Asn Ser Leu Gln Thr Asp Asp Thr Ala Met Tyr
            100                 105                 110

Tyr Cys Ala Arg Ile Val Tyr Trp Gly Gln Gly Thr Leu Val Thr Val
        115                 120                 125

Ser Ala Ala Ser Thr Lys Gly Pro Ser Val Phe Pro Leu Ala Pro Cys
    130                 135                 140

Ser Arg Ser Thr Ser Glu Ser Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175
```

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Leu Gly Thr
        195                 200                 205

Lys Thr Tyr Thr Cys Asn Val Asp His Lys Pro Ser Asn Thr Lys Val
        210                 215                 220

Asp Lys Arg Val Glu Ser Lys Tyr Gly Pro Pro Cys Pro Ser Cys Pro
225                 230                 235                 240

Ala Pro Glu Phe Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser Gln Glu Asp Pro Glu Val Gln Phe Asn Trp Tyr
        275                 280                 285

Val Asp Gly Val Glu Val His Asn Ala Lys Thr Lys Pro Arg Glu Glu
    290                 295                 300

Gln Phe Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Gly Leu Pro Ser Ser Ile Glu Lys Thr Ile Ser Lys Ala Lys Gly Gln
            340                 345                 350

Pro Arg Glu Pro Gln Val Tyr Thr Leu Pro Pro Ser Gln Glu Glu Met
        355                 360                 365

Thr Lys Asn Gln Val Ser Leu Thr Cys Leu Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Arg Leu Thr Val Asp Lys Ser Arg Trp Gln Glu Gly Asn Val
            420                 425                 430

Phe Ser Cys Ser Val Met His Glu Ala Leu His Asn His Tyr Thr Gln
        435                 440                 445

Lys Ser Leu Ser Leu Ser Leu Gly
450                 455

<210> SEQ ID NO 38
<211> LENGTH: 1385
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
gctagcacca tgggctggag ctgcatcatc ctgttcctgg tggccaccgc caccggcgtg      60
cacagccagg tgcagctgaa ggagagcggc cccggcctgg tggcccccag ccagagcctg     120
agcatcacct gcaccgtgag cggcttcagc ctgatcgact acggcgtgaa ctggatccgc     180
cagccccccg gcaagggcct ggagtggctg ggcgtgatct ggggcgacgg caccacctac     240
tacaacagcg ccctgaagag ccgcctgagc atccgcaagg acaacagcca gagccaggtg     300
ttcctgaaga tgaacagcct gcagaccgac gacaccgcca tgtactactg cgcccgcatc     360
gtgtactggg gccagggcac cctggtgacc gtgagcgccg ccagcaccaa gggcccttcc     420

```
gtgttccctc tggcccttg ctcccggtcc acctccgagt ccaccgccgc tctgggctgc    480
ctggtgaagg actacttccc tgagcctgtg accgtgtcct ggaactctgg cgccctgacc    540
tccggcgtgc acaccttccc tgccgtgctg cagtcctccg gcctgtactc cctgtcctcc    600
gtggtgaccg tgccttcctc ctccctgggc accaagacct acacctgtaa cgtggaccac    660
aagccttcca acaccaaggt ggacaagcgg gtggagtcca agtacggccc tccttgccct    720
tcctgccctg cccctgagtt cctgggcgga cctagcgtgt tcctgttccc tcctaagcct    780
aaggacaccc tgatgatctc ccggacccct gaggtgacct gtgtggtggt ggacgtgtcc    840
caggaggacc ctgaggtcca gttcaactgg tacgtggacg gcgtggaggt gcacaacgcc    900
aagaccaagc ctcgggagga gcagttcaat tccacctacc gggtggtgtc tgtgctgacc    960
gtgctgcacc aggactggct gaacggcaaa gaatacaagt gtaaggtctc caacaagggc   1020
ctgcccctcct ccatcgagaa aaccatctcc aaggccaagg ccagcctag ggagcctcag   1080
gtgtacaccc tgcctcctag ccaggaagag atgaccaaga accaggtgtc cctgacctgt   1140
ctggtgaagg gcttctaccc ttccgacatc gccgtggagt gggagtccaa cggccagcct   1200
gagaacaact acaagaccac ccctcctgtg ctggactccg acggctcctt cttcctgtac   1260
tccaggctga ccgtggacaa gtcccggtgg caggagggca acgtcttttc ctgctccgtg   1320
atgcacgagg ccctgcacaa ccactacacc cagaagtccc tgtccctgtc tctgggctga   1380
agctt                                                              1385
```

<210> SEQ ID NO 39
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met Gly Trp Ser Cys Ile Ile Leu Phe Leu Val Ala Thr Ala Thr Gly
1               5                   10                  15

Val His Ser Asp Ile Val Met Thr Gln Ala Ala Pro Ser Val Ala Val
                20                  25                  30

Thr Pro Gly Ala Ser Val Ser Ile Ser Cys Arg Ser Ser Lys Ser Leu
            35                  40                  45

Leu His Ser Ser Gly Lys Thr Tyr Leu Tyr Trp Phe Leu Gln Arg Pro
        50                  55                  60

Gly Gln Ser Pro Gln Leu Leu Ile Tyr Arg Met Ser Asn Leu Ala Ser
65                  70                  75                  80

Gly Val Pro Asp Arg Phe Ser Gly Ser Gly Ser Gly Thr Ala Phe Thr
                85                  90                  95

Leu Arg Ile Ser Arg Val Glu Ala Glu Asp Val Gly Val Tyr Tyr Cys
                100                 105                 110

Met Gln His Leu Glu Tyr Pro Tyr Thr Phe Gly Gly Gly Thr Lys Leu
            115                 120                 125

Glu Ile Lys Arg Thr Val Ala Ala Pro Ser Val Phe Ile Phe Pro Pro
        130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser 180                 185                 190
Lys Asp Ser Thr Tyr Ser Leu Ser Ser Thr Leu Thr Leu Ser Lys Ala
            195                 200                 205

Asp Tyr Glu Lys His Lys Val Tyr Ala Cys Glu Val Thr His Gln Gly
        210                 215                 220

Leu Ser Ser Pro Val Thr Lys Ser Phe Asn Arg Gly Glu Cys
225                 230                 235

<210> SEQ ID NO 40
<211> LENGTH: 731
<212> TYPE: DNA
<213> ORGANISM: Artificial Sequence
<220> FEATURE:
<223> OTHER INFORMATION: Description of Artificial Sequence: Synthetic
      polypeptide

<400> SEQUENCE: 40

```
gctagcacca tgggctggag ctgcatcatc ctgttcctgg tggccaccgc caccggcgtg     60
cacagcgaca tcgtgatgac ccaggccgcc cccagcgtgg ccgtgacccc cggcgccagc    120
gtgagcatca gctgccgcag cagcaagagc ctgctgcaca gcagcggcaa gacctacctg    180
tactggttcc tgcagcgccc cggccagagc ccccagctgc tgatctaccg catgagcaac    240
ctggccagcg gcgtgcccga ccgcttcagc ggcagcggca gcggcaccgc cttcaccctg    300
cgcatcagcc gcgtggaggc cgaggacgtg ggcgtgtact actgcatgca gcacctggag    360
tacccctaca ccttcggcgg cggcaccaag ctggagatca gcgtacggt ggccgctcct    420
tccgtgttca tcttccctcc ctccgacgag cagctgaagt ccggcaccgc ctccgtggtg    480
tgtctgctga acaacttcta ccctcgggag gccaaggtgc agtggaaggt ggacaacgcc    540
ctgcagtccg gcaactccca ggagtccgtc accgagcagg actccaagga cagcacctac    600
tccctgtcct ccaccctgac cctgtccaag gccgactacg agaagcacaa ggtgtacgcc    660
tgtgaggtga cccaccaggg cctgtccagc cctgtgacca gtccttcaa ccggggcgag    720
tgctgaagct t                                                         731
```

<210> SEQ ID NO 41
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Met Gly Trp Ser Cys Ile Ile Leu Phe Leu Val Ala Thr Ala Thr Gly
1               5                   10                  15

Val His Ser Asp Ile Val Met Thr Gln Ala Ala Pro Ser Val Ala Val
            20                  25                  30

Thr Pro Gly Ala Ser Val Ser Ile Ser Cys Arg Ser Ser Lys Ser Leu
        35                  40                  45

Leu His Ser Ser Gly Lys Thr Tyr Leu Tyr Trp Phe Leu Gln Arg Pro
    50                  55                  60

Gly Gln Ser Pro Gln Leu Leu Ile Tyr Arg Leu Ser Asn Leu Ala Ser
65                  70                  75                  80

Gly Val Pro Asp Arg Phe Ser Gly Ser Gly Ser Gly Thr Ala Phe Thr
                85                  90                  95

Leu Arg Ile Ser Arg Val Glu Ala Glu Asp Val Gly Val Tyr Tyr Cys
            100                 105                 110

```
Met Gln His Leu Glu Tyr Pro Tyr Thr Phe Gly Gly Thr Lys Leu
        115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
                180                 185                 190

Lys Asp Ser Thr Tyr Ser Leu Ser Thr Leu Thr Leu Ser Lys Ala
                195                 200                 205

Asp Tyr Glu Lys His Lys Val Tyr Ala Cys Glu Val Thr His Gln Gly
            210                 215                 220

Leu Ser Ser Pro Val Thr Lys Ser Phe Asn Arg Gly Glu Cys
225                 230                 235
```

```
<210> SEQ ID NO 42
<211> LENGTH: 731
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
gctagcacca tgggctggag ctgcatcatc ctgttcctgg tggccaccgc caccggcgtg      60
cacagcgaca tcgtgatgac ccaggccgcc cccagcgtgg ccgtgacccc cggcgccagc     120
gtgagcatca gctgccgcag cagcaagagc ctgctgcaca gcagcggcaa gacctacctg     180
tactggttcc tgcagcgccc cggccagagc ccccagctgc tgatctaccg cctgagcaac     240
ctggccagcg gcgtgcccga ccgcttcagc ggcagcggca gcggcaccgc cttcaccctg     300
cgcatcagcc gcgtggaggc cgaggacgtg ggcgtgtact actgcatgca gcacctggag     360
taccccacat ccttcggcgg cggcaccaag ctggagatca gcgtacggt ggccgctcct      420 tccgtgttca tcttccctcc ctccgacgag cagctgaagt ccggcaccgc ctccgtggtg     480
tgtctgctga caacttcta ccctcgggag gccaaggtgc agtggaaggt ggacaacgcc      540
ctgcagtccg gcaactccca ggagtccgtc accgagcagg actccaagga cagcacctac     600
tccctgtcct ccaccctgac cctgtccaag gccgactacg agaagcacaa ggtgtacgcc     660
tgtgaggtga cccaccaggg cctgtccagc cctgtgacca gtccttcaa ccggggcgag     720 tgctgaagct t                                                         731
```

```
<210> SEQ ID NO 43
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Gly Trp Ser Cys Ile Ile Leu Phe Leu Val Ala Thr Ala Thr Gly
1               5                   10                  15

Val His Ser Asp Ile Val Met Thr Gln Ala Ala Pro Ser Val Ala Val
            20                  25                  30
```

Thr Pro Gly Ala Ser Val Ser Ile Ser Cys Arg Ser Ser Lys Ser Leu
             35                  40                  45

Leu His Ser Ser Gly Lys Thr Tyr Leu Tyr Trp Phe Leu Gln Arg Pro
 50                  55                  60

Gly Gln Ser Pro Gln Leu Leu Ile Tyr Arg Leu Ser Ser Leu Ala Ser
 65                  70                  75                  80

Gly Val Pro Asp Arg Phe Ser Gly Ser Gly Ser Gly Thr Ala Phe Thr
                 85                  90                  95

Leu Arg Ile Ser Arg Val Glu Ala Glu Asp Val Gly Val Tyr Tyr Cys
                100                 105                 110

Met Gln His Leu Glu Tyr Pro Tyr Thr Phe Gly Gly Gly Thr Lys Leu
                115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
                180                 185                 190

Lys Asp Ser Thr Tyr Ser Leu Ser Ser Thr Leu Thr Leu Ser Lys Ala
                195                 200                 205

Asp Tyr Glu Lys His Lys Val Tyr Ala Cys Glu Val Thr His Gln Gly
                210                 215                 220

Leu Ser Ser Pro Val Thr Lys Ser Phe Asn Arg Gly Glu Cys
225                 230                 235

<210> SEQ ID NO 44
<211> LENGTH: 731
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
gctagcacca tgggctggag ctgcatcatc ctgttcctgg tggccaccgc caccggcgtg     60
cacagcgaca tcgtgatgac ccaggccgcc cccagcgtgg ccgtgacccc cggcgccagc    120
gtgagcatca gctgccgcag cagcaagagc ctgctgcaca gcagcggcaa gacctacctg    180
tactggttcc tgcagcgccc cggccagagc ccccagctgc tgatctaccg cctgagcagc    240
ctggccagcg gcgtgcccga ccgcttcagc ggcagcggca gcggcaccgc cttcaccctg    300
cgcatcagcc gcgtggaggc cgaggacgtg ggcgtgtact actgcatgca gcacctggag    360
tacccctaca ccttcggcgg cggcaccaag ctggagatca agcgtacggt ggccgctcct    420
tccgtgttca tcttccctcc ctccgacgag cagctgaagt ccggcaccgc ctccgtggtg    480
tgtctgctga caacttcta ccctcgggag gccaaggtgc agtggaaggt ggacaacgcc    540
ctgcagtccg gcaactccca ggagtccgtc accgagcagg actccaagga cagcacctac    600
tccctgtcct ccaccctgac cctgtccaag gccgactacg agaagcacaa ggtgtacgcc    660
tgtgaggtga cccaccaggg cctgtccagc cctgtgacca gtccttcaa ccggggcgag    720 tgctgaagct t                                                          731

<210> SEQ ID NO 45
<211> LENGTH: 456

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Met Gly Trp Ser Cys Ile Ile Leu Phe Leu Val Ala Thr Ala Thr Gly
1               5                   10                  15

Val His Ser Gln Val Gln Leu Lys Glu Ser Gly Pro Gly Leu Val Ala
            20                  25                  30

Pro Ser Glu Ser Leu Ser Ile Thr Cys Thr Val Ser Gly Phe Ser Leu
        35                  40                  45

Ile Asp Tyr Gly Val Asn Trp Ile Arg Gln Pro Pro Gly Lys Gly Leu
    50                  55                  60

Glu Trp Leu Gly Val Ile Trp Gly Asp Gly Thr Thr Tyr Tyr Asn Pro
65                  70                  75                  80

Ser Leu Lys Ser Arg Leu Ser Ile Ser Lys Asp Asn Ser Lys Ser Gln
                85                  90                  95

Val Phe Leu Lys Val Thr Ser Leu Thr Thr Asp Asp Thr Ala Met Tyr
            100                 105                 110

Tyr Cys Ala Arg Ile Val Tyr Trp Gly Gln Gly Thr Leu Val Thr Val
        115                 120                 125

Ser Ala Ala Ser Thr Lys Gly Pro Ser Val Phe Pro Leu Ala Pro Cys
    130                 135                 140

Ser Arg Ser Thr Ser Glu Ser Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Lys Thr Tyr Thr Cys Asn Val Asp His Lys Pro Ser Asn Thr Lys Val
    210                 215                 220

Asp Lys Arg Val Glu Ser Lys Tyr Gly Pro Pro Cys Pro Ser Cys Pro
225                 230                 235                 240

Ala Pro Glu Phe Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser Gln Glu Asp Pro Glu Val Gln Phe Asn Trp Tyr
        275                 280                 285

Val Asp Gly Val Glu Val His Asn Ala Lys Thr Lys Pro Arg Glu Glu
    290                 295                 300

Gln Phe Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Gly Leu Pro Ser Ser Ile Glu Lys Thr Ile Ser Lys Ala Lys Gly Gln
            340                 345                 350

Pro Arg Glu Pro Gln Val Tyr Thr Leu Pro Pro Ser Gln Glu Glu Met
        355                 360                 365

Thr Lys Asn Gln Val Ser Leu Thr Cys Leu Val Lys Gly Phe Tyr Pro
    370                 375                 380
```

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
            405                 410                 415

Tyr Ser Arg Leu Thr Val Asp Lys Ser Arg Trp Gln Glu Gly Asn Val
        420                 425                 430

Phe Ser Cys Ser Val Met His Glu Ala Leu His Asn His Tyr Thr Gln
        435                 440                 445

Lys Ser Leu Ser Leu Ser Leu Gly
    450                 455

<210> SEQ ID NO 46
<211> LENGTH: 1385
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46

| | | | | | |
|---|---|---|---|---|---|
| gctagcacca | tgggctggag | ctgcatcatc | ctgttcctgg | tggccaccgc | caccggcgtg | 60 |
| cacagccagg | tgcagctgaa | ggagagcggc | cccggcctgg | tgcccccag | cgagagcctg | 120 |
| agcatcacct | gcaccgtgag | cggcttcagc | ctgatcgact | acggcgtgaa | ctggatccgc | 180 |
| cagccccccg | gcaagggcct | ggagtggctg | ggcgtgatct | ggggcgacgg | caccacctac | 240 |
| tacaacccca | gcctgaagag | ccgcctgagc | atcagcaagg | acaacagcaa | gagccaggtg | 300 |
| ttcctgaagg | tgaccagcct | gaccaccgac | gacaccgcca | tgtactactg | cgcccgcatc | 360 |
| gtgtactggg | gccagggcac | cctggtgacc | gtgagcgccg | ccagcaccaa | gggccttcc | 420 |
| gtgttccctc | tggccccttg | ctcccggtcc | acctccgagt | ccaccgccgc | tctgggctgc | 480 |
| ctggtgaagg | actacttccc | tgagcctgtg | accgtgtcct | ggaactctgg | cgccctgacc | 540 |
| tccggcgtgc | acaccttccc | tgccgtgctg | cagtcctccg | gcctgtactc | cctgtcctcc | 600 |
| gtggtgaccg | tgccttcctc | ctccctgggc | accaagacct | acacctgtaa | cgtggaccac | 660 |
| aagccttcca | caccaaggt | ggacaagcgg | gtggagtcca | agtacggccc | ctcttgccct | 720 |
| tcctgccctg | cccctgagtt | cctgggcgga | cctagcgtgt | tcctgttccc | tcctaagcct | 780 |
| aaggacaccc | tgatgatctc | ccggacccct | gaggtgacct | gtgtggtggt | ggacgtgtcc | 840 |
| caggaggacc | ctgaggtcca | gttcaactgg | tacgtggacg | gcgtggaggt | gcacaacgcc | 900 |
| aagaccaagc | ctcgggagga | gcagttcaat | tccacctacc | gggtggtgtc | tgtgctgacc | 960 |
| gtgctgcacc | aggactggct | gaacggcaaa | gaatacaagt | gtaaggtctc | caacaagggc | 1020 |
| ctgcccteet | ccatcgagaa | aaccatctcc | aaggccaagg | gccagcctag | ggagcctcag | 1080 |
| gtgtacaccc | tgcctcctag | ccaggaagag | atgaccaaga | accaggtgtc | cctgacctgt | 1140 |
| ctggtgaagg | gcttctaccc | ttccgacatc | gccgtggagt | gggagtccaa | cggccagcct | 1200 |
| gagaacaact | acaagaccac | ccctcctgtg | ctggactccg | acggctcctt | cttcctgtac | 1260 |
| tccaggctga | ccgtggacaa | gtcccggtgg | caggagggca | acgtcttttc | ctgctccgtg | 1320 |
| atgcacgagg | ccctgcacaa | ccactacacc | cagaagtccc | tgtccctgtc | tctgggctga | 1380 |
| agctt | | | | | | 1385 |

<210> SEQ ID NO 47
<211> LENGTH: 456
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 47

```
Met Gly Trp Ser Cys Ile Ile Leu Phe Leu Val Ala Thr Ala Thr Gly
1               5                   10                  15

Val His Ser Glu Val Gln Leu Lys Glu Ser Gly Pro Gly Leu Val Ala
            20                  25                  30

Pro Gly Gly Ser Leu Ser Ile Thr Cys Thr Val Ser Gly Phe Ser Leu
        35                  40                  45

Ile Asp Tyr Gly Val Asn Trp Ile Arg Gln Pro Pro Gly Lys Gly Leu
    50                  55                  60

Glu Trp Leu Gly Val Ile Trp Gly Asp Gly Thr Thr Tyr Tyr Asn Ala
65                  70                  75                  80

Pro Leu Lys Gly Arg Leu Ser Ile Ser Lys Asp Asn Ser Lys Ser Gln
                85                  90                  95

Val Phe Leu Gln Met Asn Ser Leu Lys Thr Asp Asp Thr Ala Met Tyr
            100                 105                 110

Tyr Cys Ala Arg Ile Val Tyr Trp Gly Gln Gly Thr Leu Val Thr Val
        115                 120                 125

Ser Ser Ala Ser Thr Lys Gly Pro Ser Val Phe Pro Leu Ala Pro Cys
130                 135                 140

Ser Arg Ser Thr Ser Glu Ser Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Lys Thr Tyr Thr Cys Asn Val Asp His Lys Pro Ser Asn Thr Lys Val
210                 215                 220

Asp Lys Arg Val Glu Ser Lys Tyr Gly Pro Pro Cys Pro Ser Cys Pro
225                 230                 235                 240

Ala Pro Glu Phe Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser Gln Glu Asp Pro Glu Val Gln Phe Asn Trp Tyr
        275                 280                 285

Val Asp Gly Val Glu Val His Asn Ala Lys Thr Lys Pro Arg Glu Glu
290                 295                 300

Gln Phe Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Gly Leu Pro Ser Ser Ile Glu Lys Thr Ile Ser Lys Ala Lys Gly Gln
            340                 345                 350

Pro Arg Glu Pro Gln Val Tyr Thr Leu Pro Pro Ser Gln Glu Glu Met
        355                 360                 365

Thr Lys Asn Gln Val Ser Leu Thr Cys Leu Val Lys Gly Phe Tyr Pro
370                 375                 380
```

```
Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Arg Leu Thr Val Asp Lys Ser Arg Trp Gln Glu Gly Asn Val
            420                 425                 430

Phe Ser Cys Ser Val Met His Glu Ala Leu His Asn His Tyr Thr Gln
        435                 440                 445

Lys Ser Leu Ser Leu Ser Leu Gly
    450                 455
```

<210> SEQ ID NO 48
<211> LENGTH: 1385
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 48

```
gctagcacca tgggctggag ctgcatcatc ctgttcctgg tggccaccgc caccggcgtg      60
cacagcgagg tgcagctgaa ggagagcggc cccggcctgg tgcccccgg cggcagcctg     120
agcatcacct gcaccgtgag cggcttcagc ctgatcgact acggcgtgaa ctggatccgc     180
cagcccccg gcaagggcct ggagtggctg ggcgtgatct ggggcgacgg caccacctac     240
tacaacgccc ccctgaaggg ccgcctgagc atcagcaagg acaacagcaa gagccaggtg     300
ttcctgcaga tgaacagcct gaagaccgac gacaccgcca tgtactactg cgcccgcatc     360
gtgtactggg gccagggcac cctggtgacc gtgagcagcg ccagcaccaa gggcccttcc     420
gtgttccctc tggccccttg ctcccggtcc acctccgagt ccaccgccgc tctgggctgc     480
ctggtgaagg actacttccc tgagcctgtg accgtgtcct ggaactctgg cgccctgacc     540
tccggcgtgc acaccttccc tgccgtgctg cagtcctccg gcctgtactc cctgtcctcc     600
gtggtgaccg tgccttcctc ctccctgggc accaagacct acacctgtaa cgtggaccac     660
aagccttcca acaccaaggt ggacaagcgg gtggagtcca agtacggccc tccttgccct     720
tcctgccctg cccctgagtt cctgggcgga cctagcgtgt tcctgttccc tcctaagcct     780
aaggacaccc tgatgatctc ccggacccct gaggtgacct gtgtggtggt ggacgtgtcc     840
caggaggacc ctgaggtcca gttcaactgg tacgtggacg gcgtggaggt gcacaacgcc     900
aagaccaagc ctcgggagga gcagttcaat tccacctacc gggtggtgtc tgtgctgacc     960
gtgctgcacc aggactggct gaacggcaaa gaatacaagt gtaaggtctc caacaagggc    1020
ctgcccctcct ccatcgagaa aaccatctcc aaggccaagg ccagcctag ggagcctcag    1080
gtgtacaccc tgcctcctag ccaggaagag atgaccaaga accaggtgtc cctgacctgt    1140
ctggtgaagg cttctaccc ttccgacatc gccgtggagt gggagtccaa cggccagcct    1200
gagaacaact acaagaccac ccctcctgtg ctggactccg acggctcctt cttcctgtac    1260
tccaggctga ccgtggacaa gtccggtgg caggagggca cgtctttc ctgctccgtg    1320
atgcacgagg ccctgcacaa ccactacacc cagaagtccc tgtccctgtc tctgggctga    1380
agctt                                                                1385
```

<210> SEQ ID NO 49
<211> LENGTH: 5
<212> TYPE: PRT
<213> ORGANISM: Homo sapiens

```
<400> SEQUENCE: 49

Glu Leu Leu Gly Gly
1               5

<210> SEQ ID NO 50
<211> LENGTH: 5
<212> TYPE: PRT
<213> ORGANISM: Homo sapiens

<400> SEQUENCE: 50

Met Ile Ser Arg Thr
1               5

<210> SEQ ID NO 51
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag

<400> SEQUENCE: 51

His His His His His His
1               5

<210> SEQ ID NO 52
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Pro Gly Lys Ala Pro Gln Leu Leu Ile Tyr Arg Met Ser Asn Leu
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Pro Gly Lys Ala Pro Lys Leu Leu Ile Tyr Ala Ala Ser Ser Leu
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ser Leu Ile Asp Tyr Gly Val Asn Trp Ile Arg Gln Pro Pro Gly
1               5                   10                  15

<210> SEQ ID NO 55
<211> LENGTH: 112
<212> TYPE: PRT
<213> ORGANISM: Artificial Sequence
<220> FEATURE:
```

<223> OTHER INFORMATION: Description of Artificial Sequence: Synthetic
    polypeptide

<400> SEQUENCE: 55

```
Asp Ile Val Met Thr Gln Ala Ala Pro Ser Val Ala Val Thr Pro Gly
1               5                   10                  15

Gln Ser Val Ser Ile Ser Cys Arg Ser Ser Lys Ser Leu Leu His Ser
            20                  25                  30

Ser Gly Lys Thr Tyr Leu Tyr Trp Phe Leu Gln His Pro Gly Lys Ala
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Thr Ile
65                  70                  75                  80

Ser Gly Val Gln Ala Glu Asp Val Gly Val Tyr Tyr Cys Met Gln His
                85                  90                  95

Leu Glu Tyr Pro Tyr Thr Phe Gly Gly Gly Thr Lys Leu Glu Ile Lys
            100                 105                 110
```

<210> SEQ ID NO 56
<211> LENGTH: 113
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 56

```
Gln Val Gln Leu Gln Glu Ser Gly Pro Gly Leu Val Ala Pro Ser Gln
1               5                   10                  15

Ser Leu Ser Ile Thr Cys Thr Val Ser Gly Phe Ser Leu Ile Asp Tyr
            20                  25                  30

Gly Val Asn Trp Ile Arg Gln Pro Pro Gly Lys Gly Leu Glu Trp Leu
        35                  40                  45

Gly Val Ile Trp Gly Asp Gly Thr Thr Tyr Tyr Asn Ser Ala Leu Lys
    50                  55                  60

Ser Arg Leu Ser Ile Ser Lys Asp Thr Ser Lys Ser Gln Val Phe Leu
65                  70                  75                  80

Lys Met Asn Ser Leu Thr Thr Asp Asp Thr Ala Met Tyr Tyr Cys Ala
                85                  90                  95

Arg Ile Val Tyr Trp Gly Gln Gly Thr Leu Val Thr Val Ser Ala Ala
            100                 105                 110

Lys
```

<210> SEQ ID NO 57
<211> LENGTH: 113
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 57

```
Gln Val Gln Leu Gln Glu Ser Gly Pro Gly Leu Val Ala Pro Ser Gln
1               5                   10                  15

Ser Leu Ser Ile Thr Cys Thr Val Ser Gly Phe Ser Leu Ile Asp Tyr
            20                  25                  30

Gly Val Asn Trp Ile Arg Gln Pro Pro Gly Lys Gly Leu Glu Trp Leu
        35                  40                  45
```

```
Gly Val Ile Trp Gly Asp Gly Thr Thr Tyr Tyr Pro Ser Ala Leu Lys
 50                  55                  60

Ser Arg Leu Ser Ile Ser Lys Asp Thr Ser Lys Ser Gln Val Phe Leu
 65                  70                  75                  80

Lys Met Asn Ser Leu Thr Thr Asp Asp Thr Ala Met Tyr Tyr Cys Ala
                 85                  90                  95

Arg Ile Val Tyr Trp Gly Gln Gly Thr Leu Val Thr Val Ser Ala Ala
                100                 105                 110

Lys
```

```
<210> SEQ ID NO 58
<211> LENGTH: 16
<212> TYPE: PRT
<213> ORGANISM: Artificial Sequence
<220> FEATURE:
<223> OTHER INFORMATION: Synthetic peptide

<400> SEQUENCE: 58

Arg Ser Ser Lys Ser Leu Leu His Ser Ser Gly Lys Thr Tyr Leu Tyr
  1               5                  10                  15

<210> SEQ ID NO 59
<211> LENGTH: 7
<212> TYPE: PRT
<213> ORGANISM: Artificial Sequence
<220> FEATURE:
<223> OTHER INFORMATION: Synthetic peptide

<400> SEQUENCE: 59

Arg Met Ser Asn Leu Ala Ser
  1               5

<210> SEQ ID NO 60
<211> LENGTH: 9
<212> TYPE: PRT
<213> ORGANISM: Artificial Sequence
<220> FEATURE:
<223> OTHER INFORMATION: Synthetic peptide

<400> SEQUENCE: 60

Met Gln His Leu Glu Tyr Pro Tyr Thr
  1               5

<210> SEQ ID NO 61
<211> LENGTH: 10
<212> TYPE: PRT
<213> ORGANISM: Artificial Sequence
<220> FEATURE:
<223> OTHER INFORMATION: Synthetic peptide

<400> SEQUENCE: 61

Gly Phe Ser Leu Ile Asp Tyr Gly Val Asn
  1               5                  10

<210> SEQ ID NO 62
<211> LENGTH: 9
<212> TYPE: PRT
<213> ORGANISM: Artificial Sequence
<220> FEATURE:
<223> OTHER INFORMATION: Synthetic peptide

<400> SEQUENCE: 62

Val Ile Trp Gly Asp Gly Thr Thr Tyr
  1               5
```

<210> SEQ ID NO 63
<211> LENGTH: 3
<212> TYPE: PRT
<213> ORGANISM: Artificial Sequence
<220> FEATURE:
<223> OTHER INFORMATION: Synthetic peptide

<400> SEQUENCE: 63

Ile Val Tyr
1

<210> SEQ ID NO 64
<211> LENGTH: 7
<212> TYPE: PRT
<213> ORGANISM: Artificial Sequence
<220> FEATURE:
<223> OTHER INFORMATION: Synthetic peptide

<400> SEQUENCE: 64

Arg Leu Ser Asn Leu Ala Ser
1               5

<210> SEQ ID NO 65
<211> LENGTH: 8
<212> TYPE: PRT
<213> ORGANISM: Artificial Sequence
<220> FEATURE:
<223> OTHER INFORMATION: Synthetic peptide

<400> SEQUENCE: 65

Arg Leu Ser Ser Asn Leu Ala Ser
1               5

<210> SEQ ID NO 66
<211> LENGTH: 6
<212> TYPE: PRT
<213> ORGANISM: Artificial Sequence
<220> FEATURE:
<223> OTHER INFORMATION: Synthetic peptide

<400> SEQUENCE: 66

Arg Met Ser Asn Leu Ala
1               5

<210> SEQ ID NO 67
<211> LENGTH: 6
<212> TYPE: PRT
<213> ORGANISM: Artificial Sequence
<220> FEATURE:
<223> OTHER INFORMATION: Synthetic peptide

<400> SEQUENCE: 67

Arg Leu Ser Asn Leu Ala
1               5

<210> SEQ ID NO 68
<211> LENGTH: 6
<212> TYPE: PRT
<213> ORGANISM: Artificial Sequence
<220> FEATURE:
<223> OTHER INFORMATION: Synthetic peptide

<400> SEQUENCE: 68

Arg Leu Ser Ser Leu Ala
1               5

```
<210> SEQ ID NO 69
<211> LENGTH: 17
<212> TYPE: PRT
<213> ORGANISM: Artificial Sequence
<220> FEATURE:
<223> OTHER INFORMATION: Synthetic peptide

<400> SEQUENCE: 69

Arg Ser Ser Lys Ser Leu Leu His Ser Ser Gly Lys Thr Tyr Leu Tyr
1               5                   10                  15

Trp
```